United States Patent
Kohtz

(10) Patent No.: US 10,702,589 B2
(45) Date of Patent: Jul. 7, 2020

(54) COMPOSITIONS AND METHODS OF TREATING NEUROLOGICAL DISORDER AND STRESS-INDUCED CONDITIONS

(71) Applicant: Ann and Robert H. Lurie Children's Hospital of Chicago, Chicago, IL (US)

(72) Inventor: Jhumku D. Kohtz, Chicago, IL (US)

(73) Assignee: ANN AND ROBERT H. LURIE CHILDREN'S HOSPITAL OF CHICAGO, Chicago, IL (US)

( * ) Notice: Subject to any disclaimer, the term of this patent is extended or adjusted under 35 U.S.C. 154(b) by 0 days.

(21) Appl. No.: 15/724,921

(22) Filed: Oct. 4, 2017

(65) Prior Publication Data
US 2018/0104313 A1    Apr. 19, 2018

Related U.S. Application Data

(60) Provisional application No. 62/404,035, filed on Oct. 4, 2016.

(51) Int. Cl.
*A61K 38/44* (2006.01)
*A61K 38/00* (2006.01)
*A61P 25/00* (2006.01)

(52) U.S. Cl.
CPC .......... *A61K 38/443* (2013.01); *A61K 38/005* (2013.01); *A61P 25/00* (2018.01); *C12Y 101/01* (2013.01)

(58) Field of Classification Search
None
See application file for complete search history.

(56) References Cited

U.S. PATENT DOCUMENTS

| | | | |
|---|---|---|---|
| 5,004,697 A | 4/1991 | Pardridge | |
| 7,902,156 B2 | 3/2011 | Beliveau | |
| 2003/0078274 A1* | 4/2003 | Lipton | A61K 31/00 514/256 |
| 2005/0003998 A1* | 1/2005 | Bertilsson | A61K 31/00 514/1 |
| 2008/0019984 A1 | 1/2008 | Shusta | |
| 2015/0196663 A1 | 7/2015 | Shusta | |
| 2017/0174778 A1 | 6/2017 | Shusta | |

FOREIGN PATENT DOCUMENTS

| | | | |
|---|---|---|---|
| WO | 2003009815 | 2/2003 | |
| WO | WO-03046165 A1 * | 6/2003 | ........... C12N 9/0006 |
| WO | 2007143711 | 12/2007 | |
| WO | 2012075037 | 6/2012 | |
| WO | 2014033074 | 3/2014 | |
| WO | 2014076655 | 5/2014 | |
| WO | 2015101586 | 7/2015 | |
| WO | 2016094566 | 6/2016 | |
| WO | 2016097315 | 6/2016 | |

OTHER PUBLICATIONS

Scannevin (Fumarates Promote Cytoprotection of Central Nervous System Cells against Oxidative Stress via the Nuclear (Factor Erythroid-Derived 2)-Like 2 Pathway, 2012). (Year: 2012).*
Bouayed (Oxidative Stress and Anxiety, 2009) (Year: 2009).*
Pi, et al., (2013). Cortical interneurons that specialize in disinhibitory control. Nature 503, 521-524.
Price, et al., (1991). A mouse gene related to Distal-less shows a restricted expression in the developing forebrain. Nature 351, 748-751.
Quinlan, et al., 2010. BEDTools: a flexible suite of utilities for comparing genomic features. Bioinformatics 26: 841-842.
Redrup, et al., (2009). The long noncoding RNA Kcnq1ot1 organises a lineage-specific nuclear domain for epigenetic gene silencing. Development 136, 525-530.
Rudy, et al., (2011). Three groups of interneurons account for nearly 100% of neocortical GABAergic neurons. Developmental neurobiology 71, 45-61.
Sanyal, et al., (2012). The long-range interaction landscape of gene promoters. Nature 489, 109-113.
Soriano, 1999. Generalized lacZ expression with the ROSA26 Cre reporter strain. Nature genetics 21: 70-71.
Stevens, et al., (2017). 3D structures of individual mammalian genomes studied by single-cell Hi-C. Nature 544, 59-64.
Takahashi, et al., Induction of pluripotent stem cells from mouse embryonic and adult fibroblast cultures by defined factors. Cell, 2006. 126(4): p. 663-76.
Talge, et al., Antenatal maternal stress and long-term effects on child neurodevelopment: how and why? J Child Psychol Psychiatry. 2007;48(3-4)245-61).
van de Werken HJ et al., 2012. 4C technology: protocols and data analysis. Methods Enzymol 513: 89-112.
Waclaw, et al., (2010). Developmental origin of the neuronal subtypes that comprise the amygdalar fear circuit in the mouse. The Journal of neuroscience : the official journal of the Society for Neuroscience 30, 6944-6953.
Wand, 1994. Fast Computation of Multivariate Kernel Estimators. Journal of Computational and Graphical Statistics 3: 433-445.
Wang, et al., (2010). Dlx5 and Dlx6 regulate the development of parvalbumin-expressing cortical interneurons. J Neurosci 30, 5334-5345.
Westra et al., 2008. Aneuploid mosaicism in the developing and adult cerebellar cortex. J Comp Neurol 507: 1944-1951.
Wichterle, et al., (2001). In utero fate mapping reveals distinct migratory pathways and fates of neurons born in the mammalian basal forebrain. Development 128, 3759-3771.
Williamson, et al., (2016). Shh and ZRS enhancer colocalisation is specific to the zone of polarising activity. Development 143, 2994-3001.

(Continued)

*Primary Examiner* — Nghi V Nguyen
(74) *Attorney, Agent, or Firm* — Quarles & Brady LLP

(57) ABSTRACT

The present disclosure provides the use of Akr1b8, an agonist of Akr1b8, Akr1B10, or an agonist of Akr1B10 in methods and compositions for the treatment of neurological disorders and stress-induced conditions. Methods of increasing the levels of 5Thr3a on neuronal cells is also provided by contacting the neuronal cells with Akr1b8, an agonist of Akr1b8, Akr1B10, or an agonist of Akr1B10.

6 Claims, 34 Drawing Sheets

Specification includes a Sequence Listing.

(56) References Cited

OTHER PUBLICATIONS

Won et al., 2016. Chromosome conformation elucidates regulatory relationships in developing human brain. Nature 538: 523-527.
Xu, et al., (2010). Sonic hedgehog signaling confers ventral telencephalic progenitors with distinct cortical interneuron fates. Neuron 65, 328-340.
Zerucha, et al., (2000). A highly conserved enhancer in the Dlx5/Dlx6 intergenic region is the site of cross-regulatory Interactions between Dlx genes in the embryonic forebrain. The Journal of neuroscience : the official journal of the Society for Neuroscience 20, 709-721.
Zhou, et al., 2011. The Human Epigenome Browser at Washington University. Nat Methods 8: 989-990.
Abranches, et al., (2009) Neural Differentiation of Embryonic Stem Cells In Vitro: A Road Map to Neurogenesis in the Embryo. PLoS ONE 4(7): e6286. doi:10.1371/journal.pone.0006286.
Anderson, et al., (1997). Interneuron migration from basal forebrain to neocortex: dependence on Dlx genes. Science 278, 474-476.
Anderson, et al., (2014). Mapping the Shh long-range regulatory domain. Development 141, 3934-3943.
Andrey, et al., (2013). A switch between topological domains underlies HoxD genes collinearity in mouse limbs. Science 340, 1234167.
Berghoff, et al., Evf2 (Dlx6as) lncRNA regulates ultraconserved enhancer methylation and the differential transcriptional control of adjacent genes. Development 140: 4407-4416.
Bond, et al., 2009. Balanced gene regulation by an embryonic brain ncRNA is critical for adult hippocampal GABA circuitry. Nat Neurosci 12: 1020-1027.
Brind'Amour, et al., 2015. An ultra-low-input native ChIP-seq protocol for genome-wide profiling of rare cell populations. Nature communications 6: 6033.
Brockdorff, (2011). Chromosome silencing mechanisms in X-chromosome inactivation: unknown unknowns. Development 138, 5057-5065.
Cajigas, et al., 2015. Evf2 lncRNA/BRG1/DLX1 interactions reveal RNA-dependent inhibition of chromatin remodeling. Development 142: 2641-2652.
Cho et al. (2015). Gamma rhythms link prefrontal interneuron dysfunction with cognitive inflexibility in Dlx5/6(+/−) mice. Neuron 85, 1332-1343.
Cobos, et al., (2005). Mice lacking Dlx1 show subtype-specific loss of interneurons, reduced inhibition and epilepsy. Nature neuroscience 8, 1059-1068. de Laat, W., and Duboule, D. (2013). Topology of mammalian developmental enhancers and their regulatory landscapes. Nature 502, 499-506.
De Marco Garcia, et al., (2011). Neuronal activity is required for the development of specific cortical interneuron subtypes. Nature 472, 351-355.
DeFelipe, et al., (2013). New insights into the classification and nomenclature of cortical GABAergic interneurons. Nature reviews Neuroscience 14, 202-216.
Dekker, (2016). Mapping the 3D genome: Aiming for consilience. Nat Rev Mol Cell Biol 17, 741-742.
Ebert, et al., EZ spheres: a stable and expandable culture system for the generation of pre-rosette multipotent stem cells from human ESCs and iPSCs. Stem Cell Res, 2013. 10(3): p. 417-27.
Endo, et al., (2011). Roles of rat and human aldo-keto reductases in metabolism of farnesol and geranylgeraniol. Chem Biol Interact 191, 261-268.
Feng, et al., 2006. The Evf-2 noncoding RNA is transcribed from the Dlx-5/6 ultraconserved region and functions as a Dlx-2 transcriptional coactivator Genes Dev 20: 1470-1484.
Feng, et al., 2011. Using MACS to identify peaks from ChIP-Seq data. Current protocols in bioinformatics / editoral board, Andreas D Baxevanis [et al] Chapter 2: Unit 2 14.
Flandin, et al., 2011. Lhx6 and Lhx8 coordinately induce neuronal expression of Shh that controls the generation of interneuron progenitors. Neuron 70: 939-950.

Gallego, et al., (2007). Structural basis for the high all-trans-retinaldehyde reductase activity of the tumor marker AKR1B10. Proceedings of the National Academy of Sciences of the United States of America 104, 20764-20769.
Gelman, et al., 2010. Generation of interneuron diversity in the mouse cerebral cortex. The European journal of neuroscience 31: 2136-2141.
Gene Ontology C. 2015. Gene Ontology Consortium: going forward. Nucleic Acids Res 43: D1049-1056.
Giorgetti, et al., (2016). Structural organization of the inactive X chromosome in the mouse. Nature 535, 575-579.
Huang, et al. Aldo-Keto Reductase Family 1 Member B10 Inhibitors: Potential Drugs for Cancer Treatment, Recent Patents on Anti-Cancer Drug Discovery 2016, 11, 184-196.
Hug, et al., (2017). Chromatin Architecture Emerges during Zygotic Genome Activation Independent of Transcription. Cell 169, 216-228 e219.
Hunsberger, et al., Induced Pluripotent Stem Cell Models to Enable In Vitro Models for Screening in the Central Nervous System, Stem Cells Dev. Aug. 15, 2015;24(16):1852-64.
Kent, et al., 2002. The human genome browser at UCSC. Genome Res 12: 996-1006.
Kharchenko, et al., 2008. Design and analysis of ChIP-seq experiments for DNA-binding proteins. Nature biotechnology 26: 1351-1359.
Kmita, et al., (2003). Organizing axes in time and space; 25 years of colinear tinkering. Science 301, 331-333.
Kohtz, et al., (1998). Regionalization within the mammalian telencephalon is mediated by changes in responsiveness to Sonic Hedgehog. Development 125, 5079-5089.
Krzywinski, et al., 2009. Circos: an information aesthetic for comparative genomics. Genome Res 19: 1639-1645.
Landt, et al., 2012. ChIP-seq guidelines and practices of the ENCODE and modENCODE consortia. Genome research 22: 1813-1831.
Langmead, et al., 2012. Fast gapped-read alignment with Bowtie 2. Nat Methods 9: 357-359.
Lee et al., (2013). A disinhibitory circuit mediates motor integration in the somatosensory cortex. Nature neuroscience 16, 1662-1670.
Lettice, et al., (2003). A long-range Shh enhancer regulates expression in the developing limb and fin and is associated with preaxial polydactyly. Hum Mol Genet 12, 1725-1735.
Letzkus, et al., (2011). A disinhibitory microcircuit for associative fear learning in the auditory cortex. Nature 480, 331-335.
Li, 2009. Fast and accurate short read alignment with Burrows-Wheeler transform. Bioinformatics 25: 1754-1760.
Liu et al., 2003. A highly efficient recombineering-based method for generating conditional knockout mutations. Genome research 13: 476-484.
Liu, et al., (2016). Single-cell analysis of long non-coding RNAs in the developing human neocortex. Genome biology 17, 67.
Long, et al., (2007). Dlx-dependent and -independent regulation of olfactory bulb interneuron differentiation. The Journal of neuroscience : the official journal of the Society for Neuroscience 27, 3230-3243.
Love, et al., 2014. Moderated estimation of fold change and dispersion for RNA-seq data with DESeq2. Genome Biol 15: 550.
Marinov, et al., 2014. Large-scale quality analysis of published ChIP-seq data. G3 4: 209-223.
Merlo, et al., 2002. Mouse model of split hand/foot malformation type I. Genesis 33: 97-101.
Nagano, et al., (2017). Cell-cycle dynamics of chromosomal organization at single-cell resolution. Nature 547, 61-67.
Nery, et al., (2002). The caudal ganglionic eminence is a source of distinct cortical and subcortical cell populations. Nature neuroscience 5, 1279-1287.
Noordermeer, et al., (2011). The dynamic architecture of Hox gene clusters. Science 334, 222-225.
Nora, et al., (2012). Spatial partitioning of the regulatory landscape of the X-inactivation centre. Nature 485, 381-385.
O'Connor, et al., Maternal antenatal anxiety and behavioural/emotional problems in children: a test of a programming hypothesis, Child Psychol Psychiatry. Oct. 2003; 44(7):1025-36).

(56) References Cited

OTHER PUBLICATIONS

Penning, (2015). The aldo-keto reductases (AKRs): Overview. Chemico-biological interactions 234, 236-246.

Phillips-Cremins, et al., (2013). Architectural protein subclasses shape 3D organization of genomes during lineage commmitment. Cell 153, 1281-1295.

\* cited by examiner

FIGS. 1A-1K CONTINUED
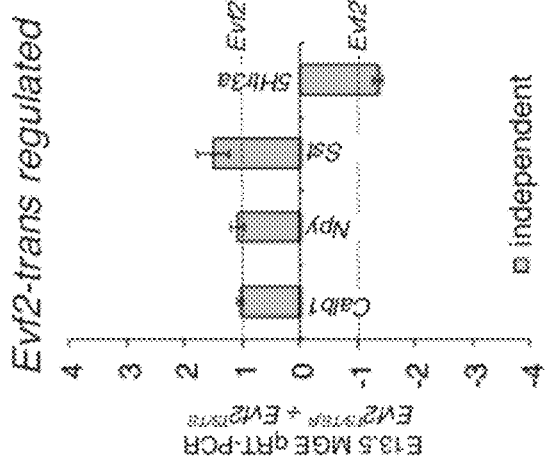
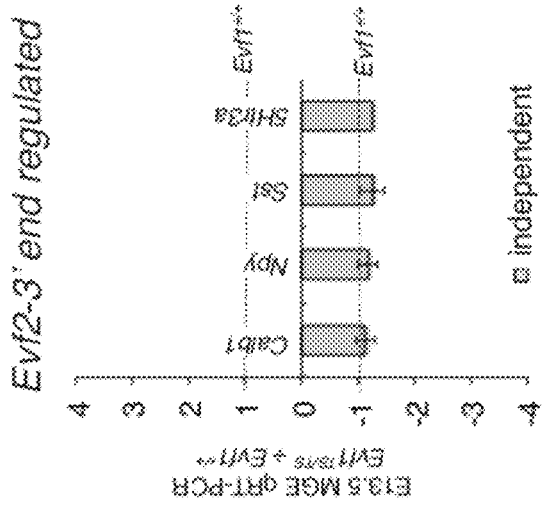
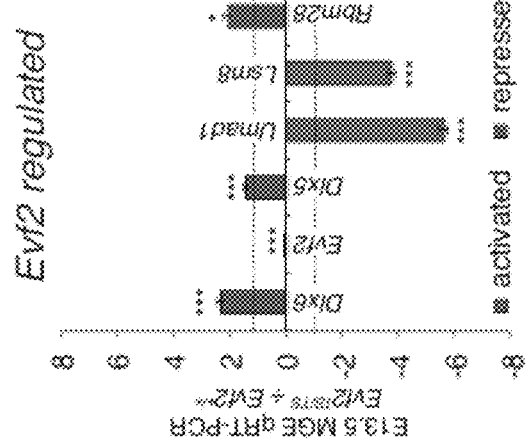

FIGS. 1A-1K CONTINUED
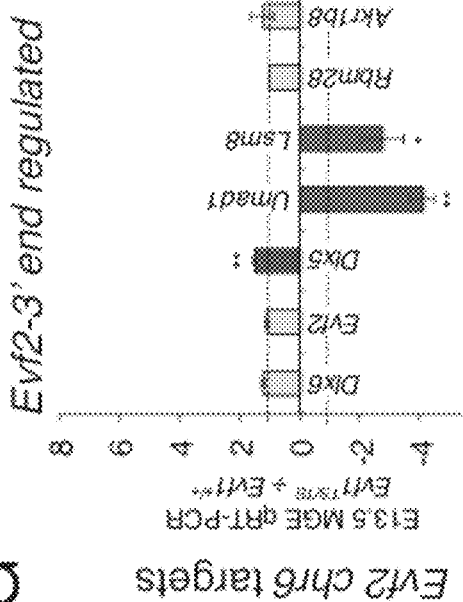
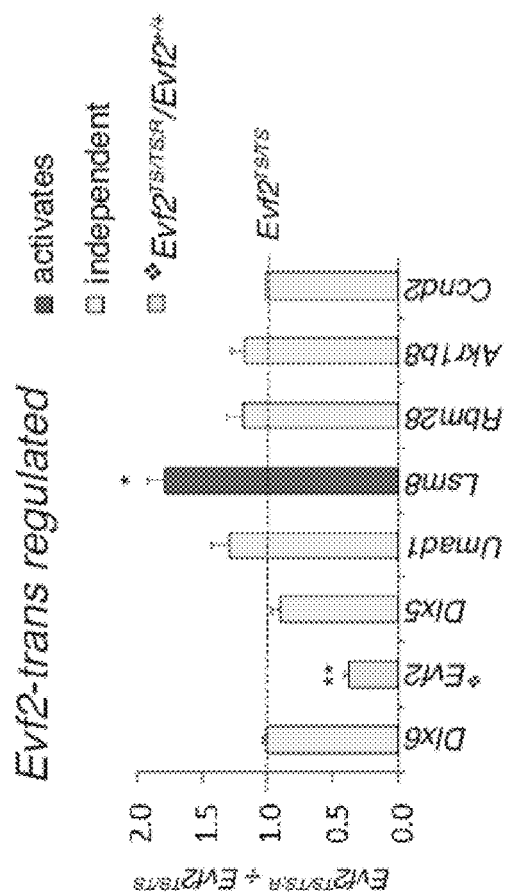

FIGS. 1A-1K CONTINUED
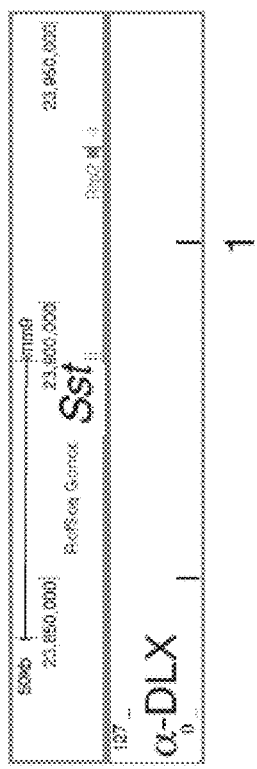
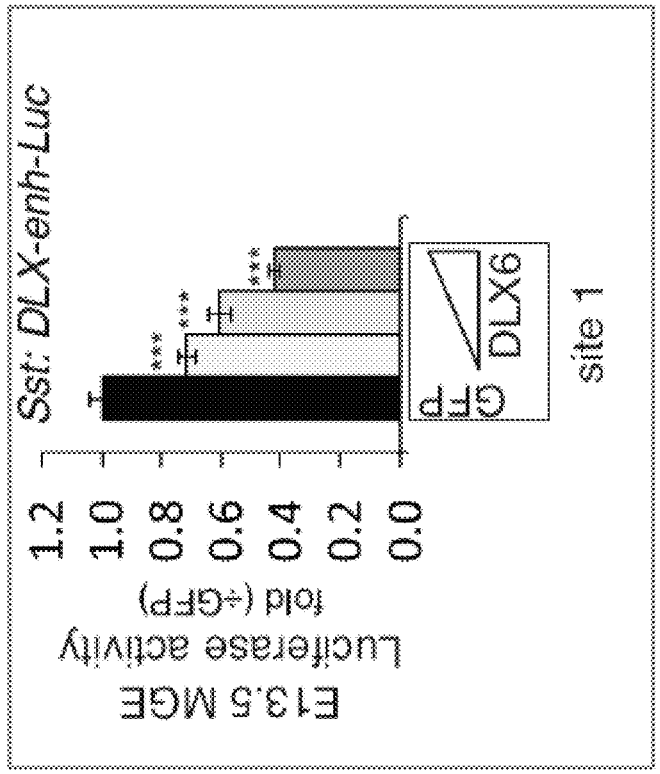
K
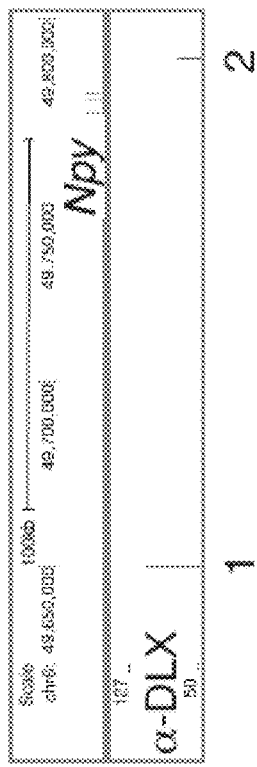
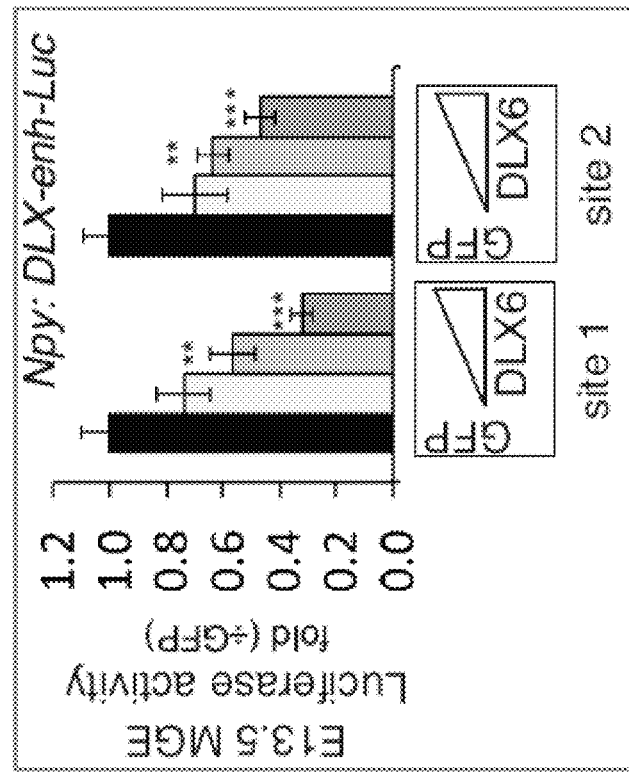
J

FIGS. 2A-2J
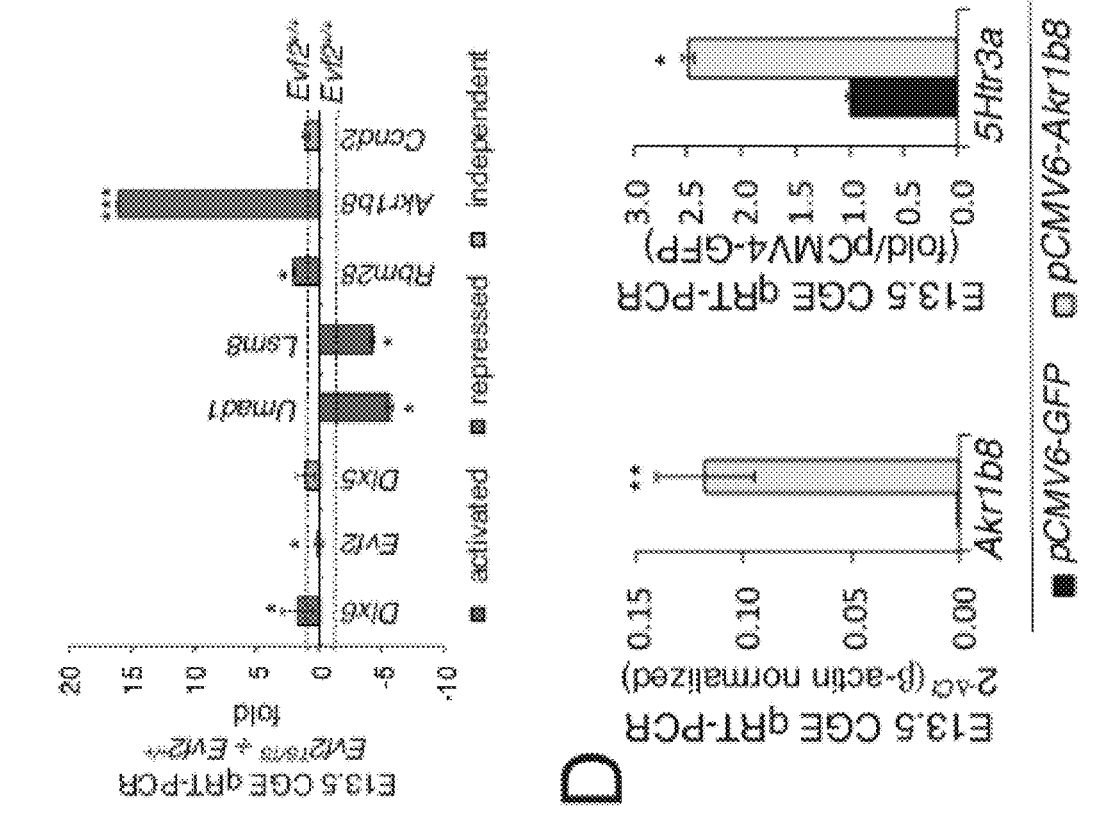
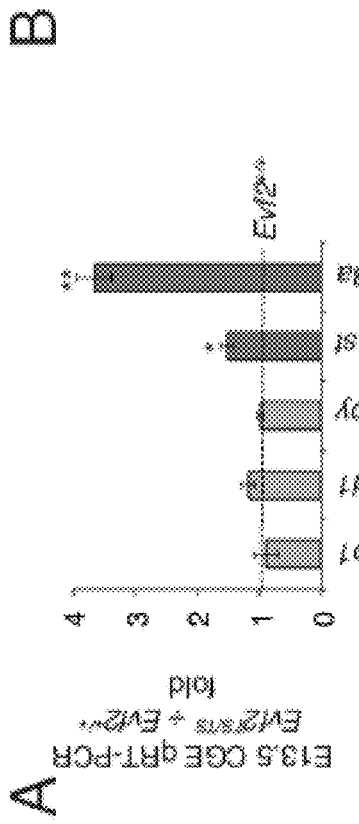
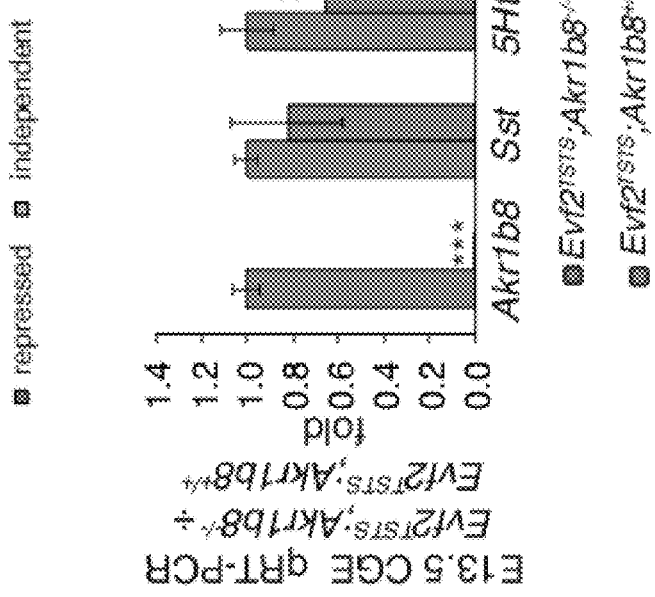

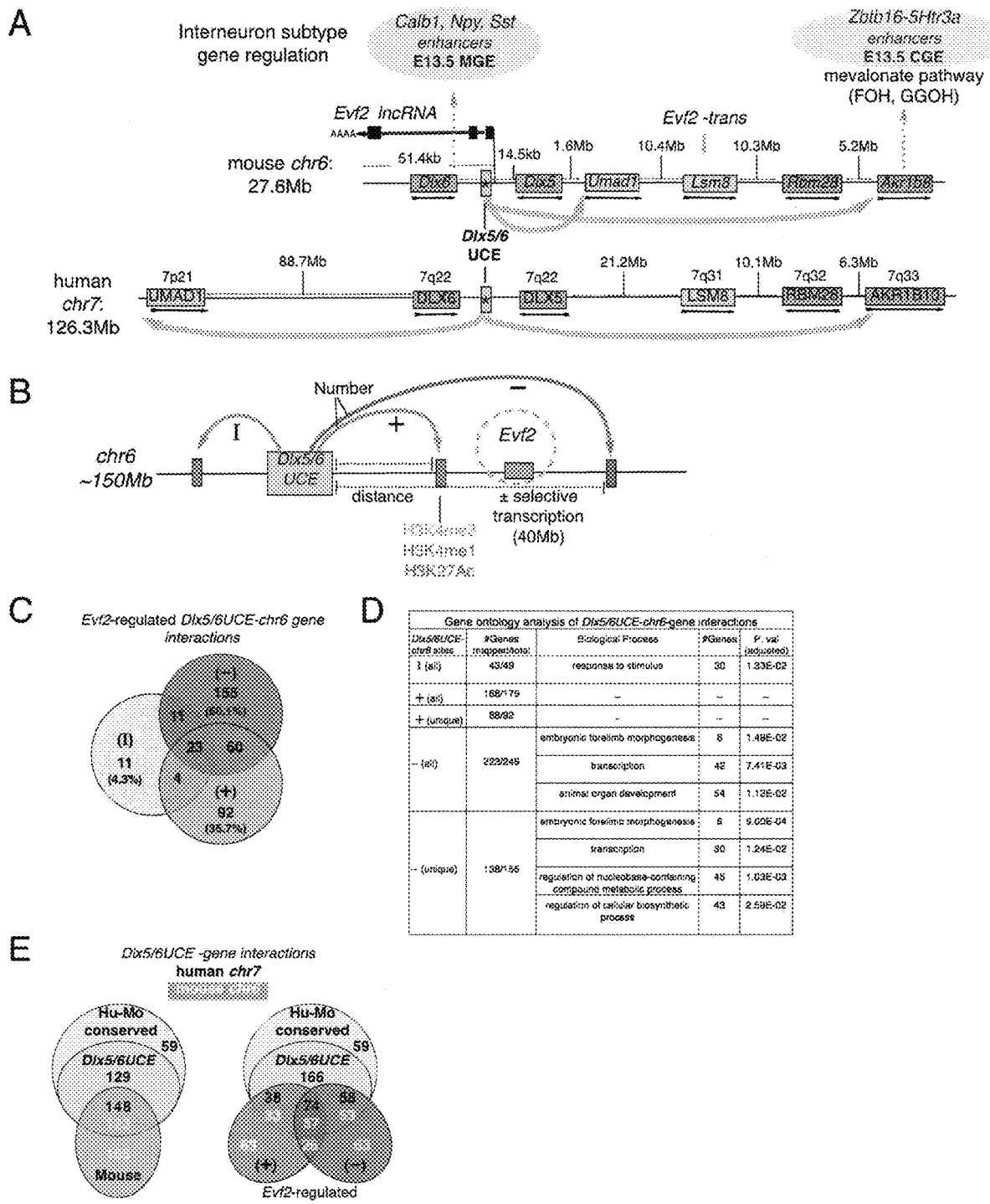
Fig. 5A-E

FIGS. 6A-6D CONTINUED
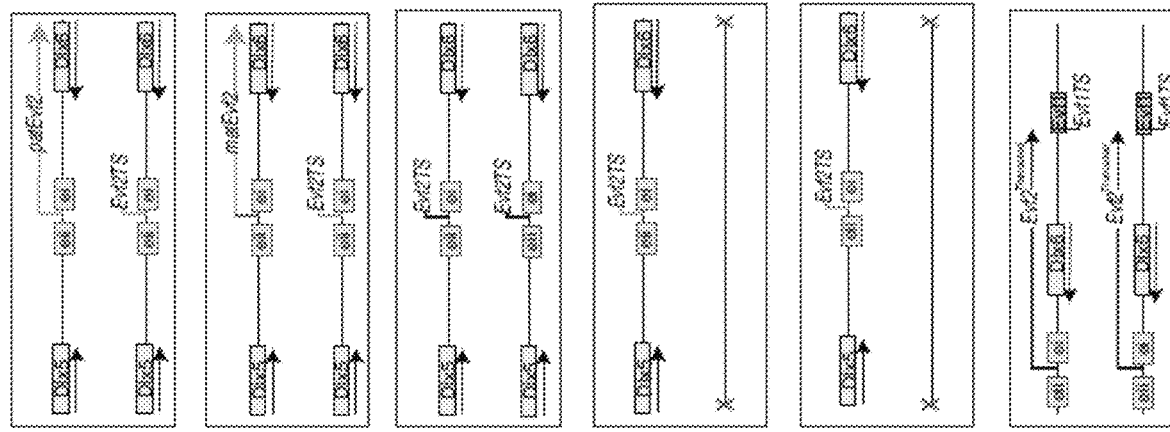
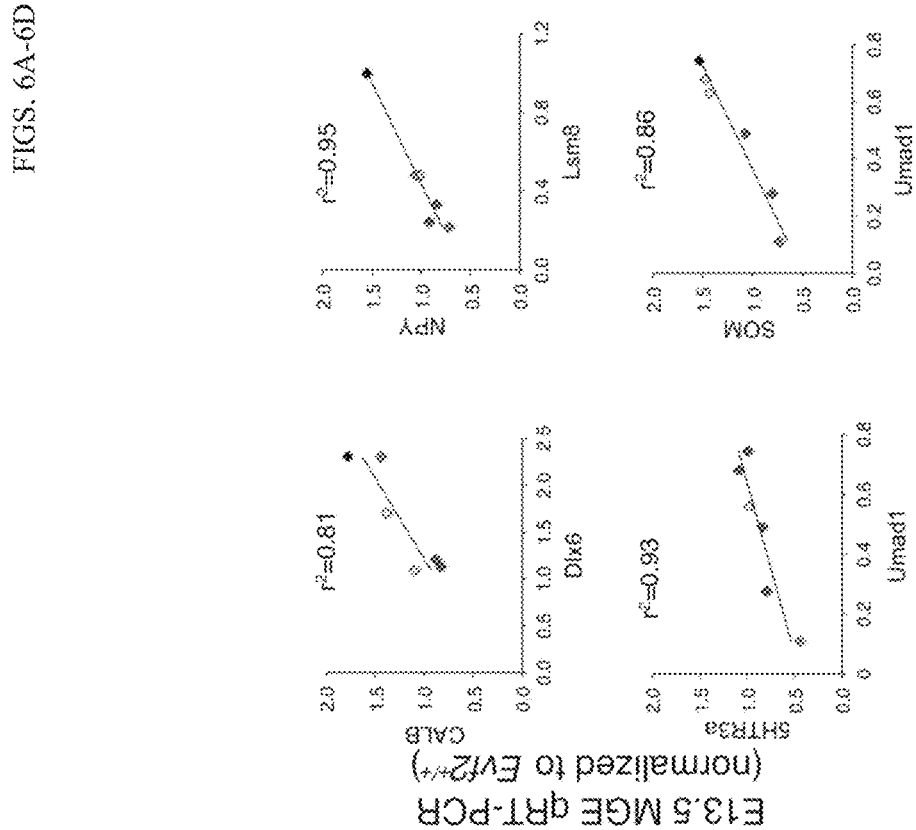

B. Distances between Dlx5/6UCE:Umad1
C. Distances between Dlx5/6UCE:Akr1b8
D. Distances between Umad1:Akr1b8.

A     *Evf2+/+*

FIGS. 9A-9G CONTINUED
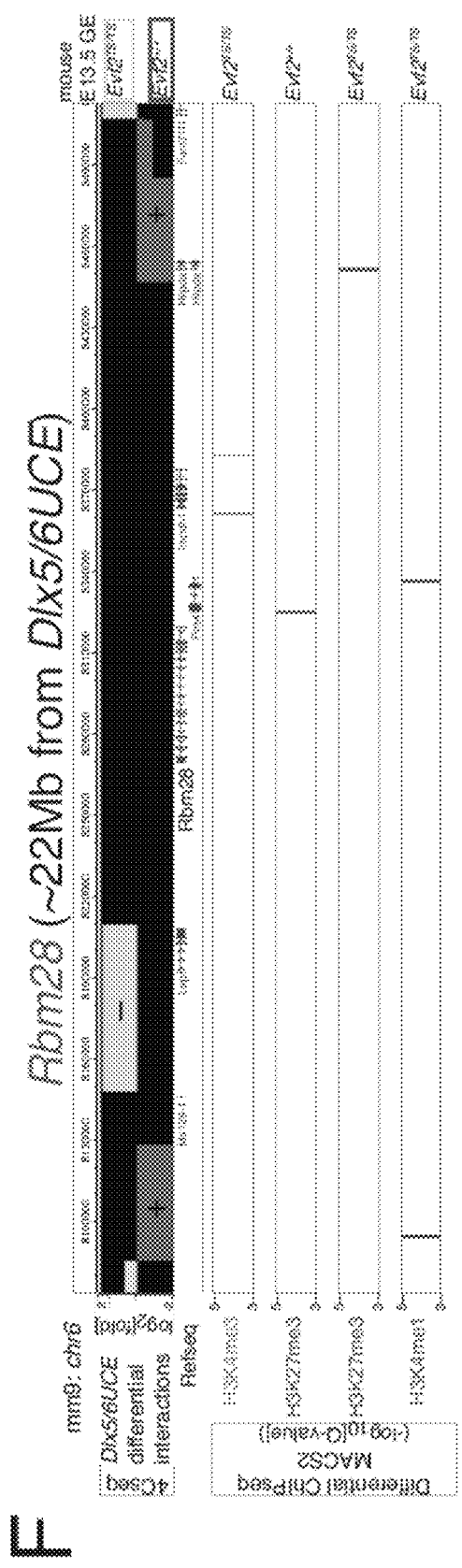
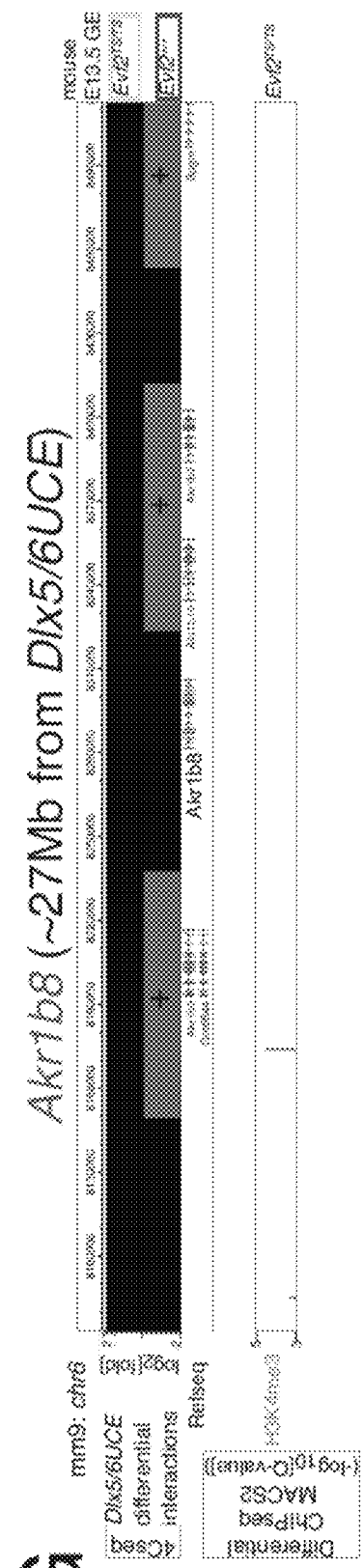

Fig. 10 Microarray of E13.5 MGE: $Evf2^{TS/TS} \div Evf2^{+/+}$
(validated list)

| Affymetrix.GeneChip.Mouse430_2 E13.5 mouse medial ganglionic eminence (E13.5 MGE) n=6 arrays/genotype fold change ≥2.0, Student's t-test p≤0.05 | | | | | |
|---|---|---|---|---|---|
| $Evf2TS/TS \div Evf2+/+$ | | | $Evf2TS/TS \div Evf2+/+$ | n=6 each genotype | |
| Gene Symbol | Fold change | Gene Ontology Biological Process | VAL | | Student's t-test, two-tailed |
| chr6 | | | Fold change | SEM | p value |
| Dlx6* | 2.22 | regulation of transcription, DNA-dependent | 2.3 | 0.14 | 1.11E-06 |
| Umad1* | -3.40 | | -5.63 | 0.16 | 4.22E-05 |
| Lsm8* | -6.65 | mRNA processing | -3.76 | 0.16 | 0.0011 |
| Rbm28* | 2.07 | mRNA processing | 2.03 | 0.17 | 0.044 |
| Akr1b8* | 4.83 | oxidation reduction | 7.27 | 0.27 | 0.023 |
| Ccnd2 | 3.04 | G1/S transition of mitotic cell cycle | 1.08 | 0.12 | 0.59 |

* validated changes by qPCR

Affymetrix.GeneChip.Mouse430_2
E13.5 mouse medial ganglionic eminence (E13.5 MGE)
n=6 arrays/genotype: Evf2TS/TS ÷ Evf2+/+
fold change ≥2.0, Student's t-test p≤0.05
Evf2TS/TS ÷ Evf2+/+
VAL: 2/23 validated by qPCR

| Gene Symbol | Fold | Gene Ontology Biological Process | VAL | Gene Symbol | Fold | Gene Ontology Biological Process | VAL |
|---|---|---|---|---|---|---|---|
| chr1 | | | | chr13 | | | |
| Ildr2 | 9.73 | response to glucose stimulus | -1.10 | Ssbp2 | 16.02 | transcription | 1.42 |
| chr3 | | | | Skiv2l2 | 11.64 | ATP catabolic process | -1.64 |
| Acad9 | -2.01 | metabolic process | -1.06 | 4833420G17Rik* | -6.05 | | -7.17 |
| chr4 | | | | Paip1 | 4.70 | regulation of translation | 1.26 |
| B3galt6 | -4.88 | glycosaminoglycan biosynthetic process | -1.05 | Gm7120 | -8.16 | | 1.40 |
| Prdm16 | -4.84 | negative regulation of transcription | 1.38 | chr14 | | | |
| chr5 | | | | Mapk8 | -4.21 | regulation of transcription, DNA-dependent | -1.35 |
| Pisd /// Pisd-ps3 | -3.41 | phospholipid biosynthetic process | 1.01 | chr17 | | | |
| chr8 | | | | Eme2 | -4.28 | DNA metabolic process | -1.01 |
| Sfrp1 | -3.53 | ureteric bud development | -1.17 | chr18 | | | |
| Prdx2 | -2.37 | activation of MAPK activity | 1.17 | Acaa2 | 2.12 | acetyl-CoA/lipid metabolic process | 1.26 |
| chr10 | | | | chr19 | | | |
| Gns | 2.03 | metabolic process | -1.07 | Pten | 2.20 | angiogenesis | -1.22 |
| chr11 | | | | chrX | | | |
| C330019G07Rik* | -3.01 | phospholipid biosynthetic process | -9.19 | Chic1 | -7.99 | | -1.04 |
| Nik | 2.59 | transcription | -1.50 | Atp7a | -2.61 | blood vessel development | -1.37 |
| chr12 | | | | Dcx | -3.35 | neuron migration | 0.91 |
| Galc | -14.02 | carbohydrate metabolic process | -1.48 | | | | |

Fig. 11 Microarray of E13.5 MGE: $Evf2^{TS/TS} \div Evf2^{+/+}$
Complete list (validated changes in yellow)

Fig. 12 In vivo dosage relationships between interneuron subtype genes and *Evf2-chr6* target genes

| RSQ: qRT-PCR E13.5 MGE (*6 genotypes) | | | | | |
|---|---|---|---|---|---|
| | CALB | GAD1 | NPY | SOM | 5HTR3a |
| Dlx6 | 0.81 | 0.18 | 0.12 | 0.00 | 0.20 |
| Evf2 | 0.01 | 0.23 | 0.09 | 0.00 | 0.02 |
| Dlx5 | 0.33 | 0.35 | 0.04 | 0.02 | 0.08 |
| Umad1 | 0.07 | 0.04 | 0.68 | 0.93 | 0.86 |
| Lsm8 | 0.52 | 0.35 | 0.95 | 0.56 | 0.34 |
| Rbm28 | 0.22 | 0.21 | 0.07 | 0.00 | 0.00 |
| Akr1b8 | 0.19 | 0.63 | 0.29 | 0.14 | 0.17 |

RSQ >0.80

*Evf2TSm/+p, Evf2TSp/+m, Evf2TS/TS, Dlx5/6KOm/TSp, Dlx5/6KOp/TSm, Evf1TS/TS pooled (n=3-7 each genotype)

E13.5 mouse ganglionic eminences

COMPOSITIONS AND METHODS OF TREATING NEUROLOGICAL DISORDER AND STRESS-INDUCED CONDITIONS

CROSS-REFERENCE TO RELATED APPLICATIONS

This application is related to, claims priority to, and incorporates by reference herein for all purposes U.S. Provisional Patent Application 62/404,035, filed Oct. 4, 2016.

STATEMENT REGARDING FEDERALLY SPONSORED RESEARCH

This invention was made with government support under R01 MH0904653 awarded by the National Institutes of Health. The government has certain rights in the invention.

BACKGROUND OF THE INVENTION

The field of the invention is the treatment of neurological diseases and stress-induced conditions, including developmental neurological disorder and mood disorders.

Early life stress and trauma is a prominent risk factor for several psychiatric illnesses, including mood and anxiety disorders (Holmes et al., 2005). Further, in utero maternal stress has been shown in clinical studies (pregnant women's exposure to a range of traumatic, as well as chronic and common life stressors (i.e., bereavement, daily hassles, and earthquake)) to result in significant alterations in children's neurodevelopment, including increased risk for mixed handedness, autism, affective disorders, and reduced cognitive ability. (Talge N M, Neal C, Glover V. Antenatal maternal stress and long-term effects on child neurodevelopment: how and why? J Child Psychol Psychiatry. 2007; 48(3-4): 245-61). More recently, maternal antenatal anxiety and/or depression have been shown to predict increased risk for neurodevelopmental disorders in children, and to confer risk for future mental illness. (O'Connor et al., Maternal antenatal anxiety and behavioural/emotional problems in children: a test of a programming hypothesis, Child Psychol Psychiatry. 2003 October; 44(7):1025-36). While early-life stress effects and in utero effects on adult psychopathology may depend upon genetic risk, the nature of gene and environment interaction is thought to play a role in the outcome.

Mood disorders are presently treated by a number of antidepressant medications. Most of these drugs are either tricyclic antidepressants (TCAs) or selective serotonin reuptake inhibitors (SSRIs). The efficacy of these drugs differs substantially among patients. These therapies can also have significant side effects. For example, more than a third of patients taking SSRIs experience sexual dysfunction. Other problematic side effects include gastrointestinal disturbances, often manifested as nausea and occasional vomiting, agitation, insomnia, weight gain, and onset of diabetes.

Present drugs directly bind serotonin receptors to affect neuronal activity, affecting all neurons expressing serotonin receptors to increase the levels of serotonin in the central nervous system (CNS).

Therefore, there is need for additional treatment options for mood disorders by targeting novel pathways that can directly affect serotonin receptor expression in subsets of neuronal populations. The present invention is directed to meeting this and other needs.

SUMMARY OF THE INVENTION

Certain embodiments of the present disclosure substantially overcome the aforementioned drawbacks by providing a novel pathway to directly increase the level of serotonin receptor gene expression in neurons, providing a novel agent for treating neurological disorders and stress-induced conditions. Applicant has found that Evf2 long non-coding RNA modulates serotonin receptor expression by decreasing the expression of a specific enzyme, Akr1b8, in developing interneurons. Mice lacking Evf2 exhibit changes in behavior, including behavioral despair, learning and seizure susceptibility. This disclosure provides compositions and methods of treating neurological disorders and stress-induced conditions by treating a subject with Akr1b8/B10 or an agonist thereof. Further, the disclosure provides methods and compositions for treating neurological disorders and stress-induced conditions by treating a subject with small molecule effectors or metabolites of the mevalonate pathway.

In one aspect, the disclosure provides a method of treating a neurological disorder or stress-induced condition in a subject, the method comprising the steps of: administering an effective amount of at least one aldo-keto reductase family 1, member b10 (Akr1b10), aldo-keto reductase family 1, member B8 (Akr1b8), an agonist of Akr1b10, or an agonist of Akr1b8 in order to alleviate, reduce or inhibit one or more symptoms of the neurological disorder or stress induced condition in the subject.

In another aspect, the present disclosure provides a method of increasing expression of 5-hydroxytryptamine receptor 3A (5Htr3a) in at least one neuron, the method comprising contacting the at least one neuron with at least one selected from the group consisting of Akr1b8, an agonist of Akr1b8, Akr1b10 and an agonist of Akr1b10, wherein the at least one neuron exhibits an increase in expression of 5Htr3a.

In another aspect, the present disclosure provides a method of increasing the serotonin level in a subject, the method comprising administering to the subject Akr1b8, an agonist of Akr1b8, Akr1b10, an agonist of Akr1b10, or a combination thereof, in an effective amount to increase the serotonin level in the subject.

In yet another aspect, the disclosure provides a method of inducing a pluripotent stem cell to differentiate into a neuron comprising culturing the pluripotent stem cell with Akr1b8, an agonist of Akr1b8, Akr1b10, an agonist of Akr1B10, or a combination thereof wherein the pluripotent stem cell differentiates into a neuron that expresses 5Htr3a.

In another aspect, the disclosure provides a method of treating a neurological disorder or stress-induced disorder, the method comprising administering in an effective amount a small molecule effector or metabolite of the mevalonate pathway, wherein administration of the small molecule effector or metabolite alleviate, reduce or inhibit at least one or more symptoms of the neurological disorder or stress-induced disorder.

The foregoing and other aspects and advantages of the invention will appear from the following description. In the description, reference is made to the accompanying drawings which form a part hereof, and in which there is shown by way of illustration at least one preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A-E. Biological significance of Evf2-Dlx5/6UCE-chr6 interactions. A. A schematic showing Evf2 regulation of genes located across a 27 Mb region of mouse chr6. Evf2 is transcribed from the Dlx5/6UCE (yellow, *), and also transcribed antisense to Dlx6. Evf2 represses Dlx6, Rbm28 and Akr1b8 (red boxes) through Evf2-5' Dlx5/6UCE-containing region. Dlx6 dosage regulates enhancers in interneuron subtype genes (Calb1, Npy, Sst), contributing to interneuron diversity. Akr1b8, an aldoketoreductase and mevalonate pathway metabolites (FOH and GGOH) regulate enhancers at the promoter of Zbtb16, downstream of the interneuron subtype gene (5Htr3a). Evf2 activates Umad1 and Lsm8 (green boxes), activating Lsm8 through trans-mechanisms (green arrow). Umad1 and Lsm8 dosage are genetically linked to interneuron subtype gene dosage (Umad1:5Htr3a, Umad1: Sst, Lsm8:Npy), through unknown mechanisms. Evf2 regulation of interneuron subtype genes depends on embryonic brain region (MGE vs. CGE). Evf2-chr6 target gene organization is conserved with human chr7, except UMAD1 is located 88 Mb 3' of Dlx5/6UCE (7p21). Despite this inversion, Dlx5/6UCE-Umad1 and Dlx5/6UCE-Akr1b8/10 interactions are conserved in mouse E13.5GE and developing human brain (orange arrows). B. The Evf2 RNA cloud (dashed green circle) localizes to both activated and repressed target genes in the instructive 27 Mb region (orange box). Along chr6, Dlx5/6UCE interaction sites are divided into Evf2 positively (+, green arrow), negatively (−, red arrow), and independent (I, grey arrow), indicating that Evf2 regulates both the number and position of (+) and (−) sites. Histone modifications distinguish between (+) and (−), where active marks H3K4me3/1 and H3K27ac are enriched at (+) compared to (−) sites. C. Venn diagram showing the relationship between genes near Evf2-regulated (+ green circle, − red circle) and independent (I, grey circle) Dlx5/6-chr6 sites. D. Gene ontology (GO) analysis of Dlx5/6UCE-chr6 interactions in mouse E13.5GE, indicating specific biological processes at genes near (I) and (−) sites, but not (+) sites. E. Venn diagram showing Dlx5/6UCE-gene interactions that are conserved between human chr7 (developing brain) and mouse chr6 (E13.5GE) (black numbers, human, Hu, white numbers, mouse, Mo). ~44% of Dlx5/6UCE-chr7 gene interactions are conserved with mice (orange circle overlap with deep yellow), while ~51% are Evf2-regulated (green and red overlap with deep yellow).

FIG. 10. Table of microarray analysis of gene expression in E13.5 MGE Evf2$^{+/+}$÷Evf2$^{TS/TS}$: Taqman qPCR validations.

FIG. 11. Table of microarray analysis of gene expression in E13.5 MGE Evf2$^{+/+}$÷Evf2$^{TS/TE}$: complete list FIG. 12: RSQ Table of in vivo dosage relationships between interneuron subtype genes and Evf2-chr6 target genes FIG. 13 is a schematic of a model summarizing spatial dependence of the Evf2-Akr1b8-5Htr3a pathway in E13.5 mouse brain ganglionic eminences, (MGE and CGE), beginning with Shh activation of Dlx1/2 and Evf1/2 (Kohtz et al. 1998; Feng et al. 2006), and ending with differential regulation of 5Htr3a.

DETAILED DESCRIPTION OF THE INVENTION

Figures 1A, 1B, 1C, 1D, 1E, 1F, 1G, 1H, 1I, 1J, 1K:
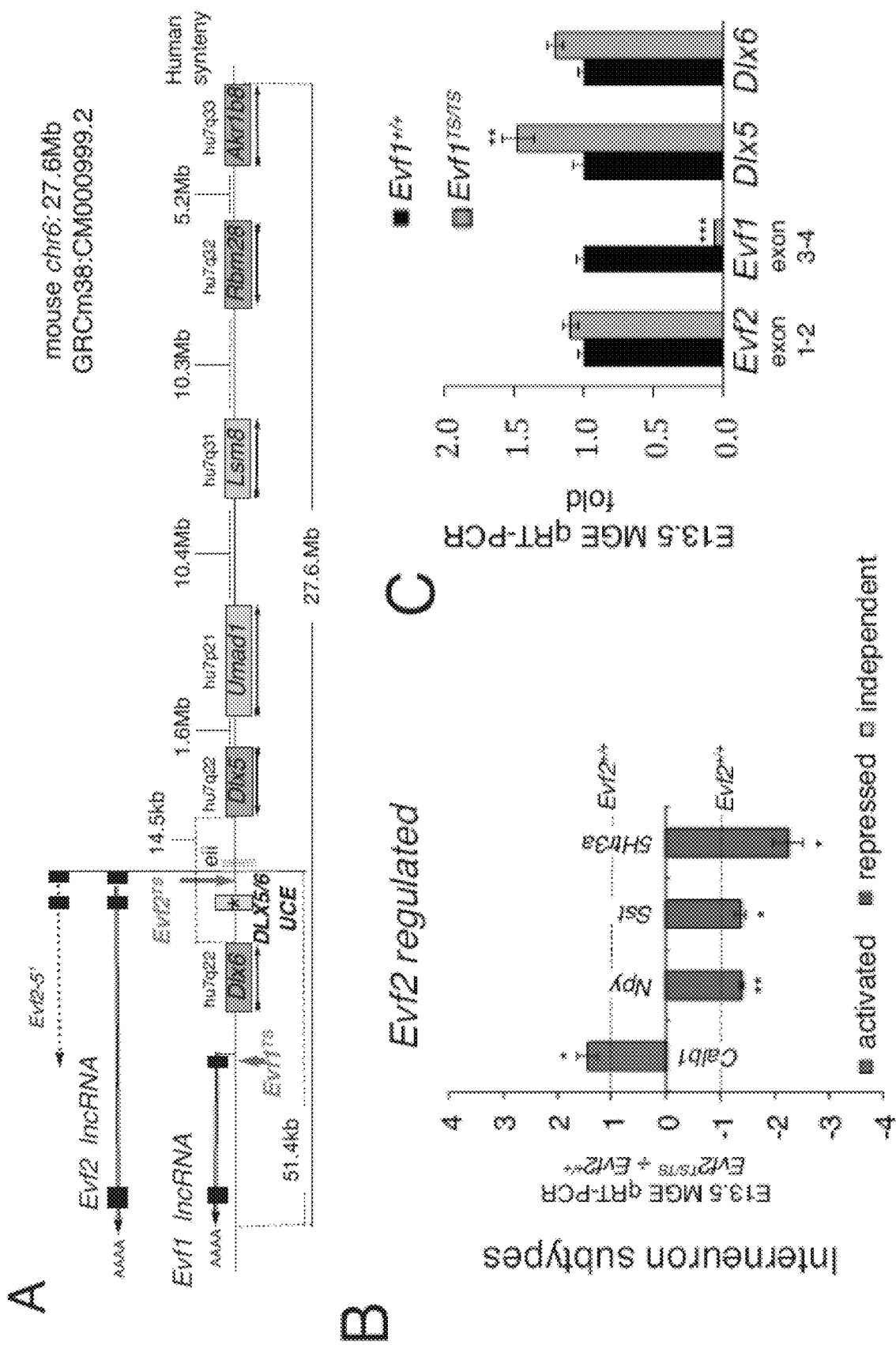
FIG. 1A-1K. Evf2 enhancer lncRNA regulation of genes across 27 Mb and Dlx6 dosage regulated interneuron subtype enhancers. A. Schematic of the 27.6 Mb region of mouse chr6 encompassing Evf2 and transcriptionally regulated target genes. Evf1 and Evf2 lncRNAs are spliced, polyadenylated transcripts, transcribed over a ~51 kb region. Dlx5/6 intergenic region, enhancers (Dlx5/6UCE, eii), (Zerucha et al., 2000)). Red arrows indicate sites of triple polyA transcription stop insertions, preventing Evf2 (Evf2TS) and Evf1 (Evf1TS) transcription in mice. Evf2-chr6 targets, identified by microarray, and validated by qRT-PCR (FIG. 10), are asymmetrically located across 27 Mb region. The corresponding human chr7 loci are indicated. B.-H. MGE qRT-PCR gene expression analysis from mice lacking Evf2 (Evf2$^{TS/TS}$, Evf2-regulated), lacking Evf1 and expressing truncated Evf2-5' (Evf1$^{TS/TS}$, Evf2-3'-regulated), expressing an Evf2 transgene (Evf2$^{TS/TS:R}$ trans-regulated), or wildtype littermates (Evf1$^{+/+}$, Evf2$^{+/+}$). B interneuron subtype genes (Calb1, Npy, Sst, 5Htr3a) in Evf2$^{TS/TS}$ normalized to Evf2$^{+/+}$, C. Evf2-5' (exon1-2), Evf1 (exon3-4), Dlx5, and Dlx6, in Evf1$^{TS/TS}$ (grey bars), normalized to Evf1$^{+/+}$ (black bars). D. interneuron subtype genes (Calb1, Npy, Sst, 5Htr3a) in Evf1$^{TS/TS}$ normalized to Evf1$^{+/+}$, E. interneuron subtype genes (Calb1, Npy, Sst, 5Htr3a) in Evf2$^{TS/TS}$ normalized to Evf2$^{TS/TS}$. F. chr6 targets: Evf2$^{TS/TS}$ normalized to Evf2$^{+/+}$, G. chr6 targets: Evf1$^{TS/TS}$ normalized to Evf1$^{+/+}$, H. chr6 targets: Evf2$^{TS/TS:R}$ normalized to Evf2$^{TS/TS}$ (except for yellow bar, normalized to Evf2$^{+/+}$). A-H: n=4-7 of each genotype, values normalized to Evf2$^{+/+}$, Evf1$^{+/+}$, or Evf2$^{TS/TS}$ (dotted lines), A, C-H, red (repressed genes, Dlx6, Dlx5, Rbm28, Akr1b8, Calb), green (activated genes, Umad1, Lsm8, Npy, Sst, 5Htr3a), grey (Evf2 independent gene, Ccnd2). I-K. UCSC browser display of interneuron genes and DLX binding sites identified by ChIP-seq. Dlx6 dosage-dependent regulation of DLX binding sites is tested in luciferase reporter assays, using primary MGE cells. Triangles represent increasing concentrations of Dlx6 plasmid; results are normalized to plasmid expressing GFP. I. Calb1 gene, Dlx6-regulated 2/3 DLX binding sites, J. Npy gene, Dlx6-regulated 2/2 DLX binding sites, K. Sst (Som) gene, Dlx6-regulated 1/1 DLX binding sites. I-K, n=12/condition, values from two experiments, Student's t-test, *p<0.05, p<0.01, *p<0.001, error bars (S.E.M).

The present disclosure provides compositions and methods for the treatment of neurological disorders or stress-induced conditions. Applicant surprisingly found that Evf2 long non-coding RNA modulates serotonin receptor expression by increasing the expression and activation of aldo-keto reductase 1b8 (Akr1b8) (mouse) in developing interneurons. By increasing the levels of Akr1b8/10, neuronal cells increase expression and activation of 5-hydroxytryptamine receptor 3A (ionotropic serotonin receptor 5HT3a or 5HTr3a). The increase in 5HTr3a receptor leads to the increase in serotonin in a subset of neuronal cells. This increase in serotonin can alleviate, reduce, attenuate or inhibit one or more symptoms of a neurological disorder or stress-induced condition.

This disclosure provides compositions and methods of treating neurological disorders and stress-induced conditions by treating a subject with an effective amount of Akr1b8/B10, or an agonist thereof. Further, the disclosure provides methods and compositions for treating neurological disorders and stress-induced conditions by treating a subject with small molecule effectors or metabolites of the mevalonate pathway. The present disclosure demonstrates that the activation of aldo-keto reductase1b8 (Akr1b8) or the human homolog Akr1b10 regulates and activates 5Htr3a, and in turn increases the level of serotonin in the brain.

The present disclosure provides improved compositions and methods of treating neurological disorders, including mood disorders, over the standard serotonin specific reuptake inhibitors (SSRIs) by directly regulating and increasing the amount of 5Htr3a (serotonin receptor) on a subset of neuronal cells, which in turn regulates serotonin levels in the brain of a subject.

In some embodiments, the present disclosure provides a method of treating a neurological disorder or stress-induced condition in a subject. The method comprises administering at least one of aldo-keto reductase family 1, member b10 (Akr1b10), aldo-keto reductase family 1, member b8 (Akr1b8), an agonist of Akr1b10, or an agonist of Akr1b8 in an effective amount to alleviate, reduce or inhibit one or more symptoms of the neurological disorder or stress induced condition in the subject.

Aldo-keto reductase family 1, member b10 (Akr1b10) (SEQ ID NO: 1) is the human homolog of aldo-keto reductase family 1, member b8 (Akr1b8) (SEQ ID NO: 3) in mice. Akr1b10 belongs to the AKR superfamily composed of more than 100 proteins that are structurally and/or functionally conserved in hierarchy of organisms from bacteria to humans. Akr1b10 is a monomeric enzyme with NADPH as a co-enzyme, and its enzyme activity is regulated by S-thiolation at the protein level. It is contemplated that either Akr1b10 or Akr1b8 can be used in the methods of the present disclosure. In some embodiments, a polypeptide comprising or consisting of SEQ ID NO:1 or SEQ ID NO:3 are used.

The Akr1b10 or Akr1b8 protein used in methods of the present disclosure may be a recombinant form of the protein or a protein directly or indirectly linked to an exogenous tag or agent. Suitable tags are known in the art and include, but are not limited to, affinity or epitope tags (nonlimiting examples include, e.g., cMyc, HIS, FLAG, V5-tag, HA-tag, NE-tag). Suitable agents include agents that help with the bioavailability or targeting of the protein, for example, but not limited to, agents that specifically target the blood brain barrier to allow for translocation of the proteins into the brain of a subject. In some embodiments, the Akr1b10 or Akr1b8 protein or agonists thereof may be directly or indirectly linked to an antibody or molecule with blood-brain barrier or blood-CSF barrier penetrant properties. For example, antibodies having binding specificity for the blood brain barrier are known in the art and include, but are not limited to, an antibody specific for a blood-brain barrier (BBB) receptor (BBBR) which allows for BBV transcytosis properties, a polypeptide or liposome that allows for BBB transport. In some embodiments, the blood brain barrier receptor is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), and heparin-binding epidermal growth factor-like growth factor (HB-EGF). Suitable BBBR are discussed for example in WO2012/075037, WO/2014/033074 and WO2015101586, the contents of which are incorporated by reference in their entireties. Further, suitable blood-brain barrier targeting antibodies are discussed in, for example, US2008/0019984, US20150196663, U.S. Pat. No. 5,004,697, WO 2016094566, PCT/US2007/070587, US20170174778, which are incorporated by reference in their entireties. Suitable blood brain barrier polypeptides are known in the art and include, but are not limited to, polypeptides discussed in WO2014076655 A1, WO2003009815 A2, WO2016097315, U.S. Pat. No. 7,902,156, WO2016097315, among others.

Suitable AkrB10 modulators are known in the art and include, but are not limited to, for example, tolrestat, EBPC (Ethyl-1-benxzyl-3-hydroxy-2(5H)-oxopyrrole-4-carboxylate), zopolrestat, sorbinil, epalrestat, fidarestat, statil ([3-(4-Bromo-2fluorobenzyl)-4-oxo-3H-phthalazin-1-yl]acetic acid), isolithocholic acid, androst-4-ene-3,6-dione, androst-4-ene-3β,6α-diol, PGA1, apigenin, luteolin, 7-hydroxyflavone, magnolol, honokiol, resveratrol, BDMC (disdemethoxycurcumin), butein, oleanolic acid, γ-mangostin, CAPE (acceic acid phenethyl ester), 3-(4-hydroxy-2-methoxyphenyl) acrylic acid 3-(3-hydroxypehnyl)propyl ester, MTF (9-methyl-2,3,7-trihydroxy-6-fluorone), (Z)-2-(4-methoxyphenylimino)-7-hydroxy-N-(pyridine-2-yl)-2H-chromene-3-carboxamide, 7-hydroxy-2-(4-methoxyphenylimino)-2H-chromene-3-carboxylic acid benzylamide, UVI2008, androstane-3β,5α,6β,19-tetraol, JF0064, JF0049, VA (glycyrrhetic acid), diclofenac, flufenamic acid, sulindac, among others, some of which can be found in Huang et al. "Aldo-Keto Reductase Family 1 Member B10 Inhibitors: Potential Drugs for Cancer Treatment, *Recent Patents on Anti-Cancer Drug Discovery* 2016, 11, 184-196, the contents of which are incorporated by reference in their entirety.

In further embodiments, the Akr1b10 and Akr1b8 agonist may include, but are not limited to Akr1b10 antisense RNA, Evf2 antisense RNA, Dlx6 antisense RNA, Akr1b10 siRNA, AKr1b8 siRNA, Evf2 siRNA, Dlx6 siRNA, or combinations thereof. Suitable antisense RNA can be derived from one skilled in the art, for example using SEQ ID NO:1, A single-stranded RNA (antisense RNA (asRNA)) is complementary to a messenger RNA (mRNA) strand transcribed within a cell, the asRNA and are from about 15 to 30 bp long. siRNA consists of two RNA strands, an antisense (or guide) strand and a sense (or passenger) strand, which form a duplex from about 19-25 bp in length, usually with a 3' dinucleotide overhang. siRNA against Akr1b10 can also be found commercially sold by a number of companies, for example, Ambion Inc (Austin, Tex., e.g. Sense (AGAGGAAUGUGAUUGUCAUTT SEQ ID NO:5) and anti-sense (AUGACAAUCACAUUCCUCUGG SEQ ID NO:6) oligonucleotides available for purchase) and from Novus Biologicals (Littleton Colo.). Suitable siRNA or asRNA can be derived by one skilled in the art using the sequences of Dlx6 and Evf2 known in the art, for example, from Dlx6 using SEQ ID NO: 52 or 53, and Evf2 using SEQ ID NO:53 and 54.

In some embodiments, the Akr1b10, Akr1b8, Akr1b10 or Akr1b8 agonists of the present disclosure may be delivered to neurons by use of a suitable expression vector for delivery into the subject. A recombinant expression cassette comprising a polynucleotide encoding the protein or agonist of the present invention is also contemplated. The polynucleotide may be under the control of a transcriptional promoter allowing the regulation of the transcription of the polynucleotide in a host cell.

The present disclosure also provides a recombinant expression cassette comprising a polynucleotide according to embodiments of the present disclosure under the control of a transcriptional promoter allowing the regulation of the transcription of the polynucleotide in a host cell, e.g. a neuronal cell. The polynucleotide can also be linked to appropriate control sequences allowing the regulation of its translation in a host cell.

The present disclosure also provides a recombinant vector (e.g., a recombinant expression vector) comprising a polynucleotide according to the present invention. Advantageously, the recombinant vector is a recombinant expression vector comprising an expression cassette according to the present disclosure.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

In some embodiments, the expression vector is a viral vector. Suitable viral vectors are known in the art and include, but are not limited to, for example, an adenovirus vector; an adeno-associated virus vector; a pox virus vector, such as a fowlpox virus vector; an alpha virus vector; a bacloviral vector; a herpes virus vector; a retrovirus vector, such as a lentivirus vector; a Modified Vaccinia virus Ankara vector; a Ross River virus vector a Sindbis virus vector; a Semliki Forest virus vector; and a Venezuelan Equine Encephalitis virus vector.

In some embodiments, a viral vector comprising at least one DNA regulatory sequence, e.g. enhancer, is provided. The DNA regulatory sequence is a nucleic acid sequence which is able to increase transcription of the target gene (for example, by leading to an increase in the number of transcripts produced over a given period of time, in comparison to the number of transcripts produced in the same period of time in the absence of the enhancer). The DNA regulatory sequence may be located anywhere in the viral vector, for example upstream or downstream of the promoter and gene. In some embodiments, the DNA regulator sequence is an enhancer and able to be present in either orientation.

Suitable DNA regulatory sequences include, but are not limited to, for example, the DNA regulatory sequences comprising or consisting of AkrRE1, AkrRE2, DLX binding site in (Zbtb16-5Htr3a), CALB1-DLX6 regulated enhancer 1, CALB1-DLX6 regulated enhancer 3, NPY-DLX6 regulated enhancer 1, NPY-DLX6 regulated enhancer 2, SST-Dlx6 regulated enhancer 1, homologous sequences thereof, or fragments thereof. Suitably, in some embodiments, the DNA regulatory elements are selected from the group consisting of SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50 and a combination thereof.

In the context of the DNA regulatory sequence or fragment thereof comprises or consists of a nucleic acid sequence having at least 70% (such as at least 75, 80, 82, 84, 86, 88, 90, 92, 94, 96, 98, 99 or 100%) sequence identity to the nucleic acid sequence of SEQ ID NO:26, SEQ ID NO:29, SEQ ID NO:32, SEQ ID NO:35, SEQ ID NO:38, SEQ ID NO:41, SEQ ID NO:44, SEQ ID NO:47, or SEQ ID NO:50, more preferably at least 75%, alternatively at least 80%. Proposed enhancers in humans can be found in SEQ ID NOs:55-60.

Suitably, in one embodiment the enhancers described herein of the 5Htr3a gene are regulated by Akr1b8. In some embodiments, these DNA regulatory sequences are used in viral vectors to specifically target and express genes in neurons expressing 5Htr3a.

In some embodiments, the expression vector further contains at least one DNA regulatory sequence, e.g. an enhancer, that enhances neuronal cells resulting in an increased expression of 5Htr3a receptors. In some embodiments, the expression vector further contains at least one DNA regulatory sequence and the nucleotide sequence for Akr1b10, Akr1b8, Akr1b10 agonist or Akr1b8 agonist as described herein to target expression in neuronal cells resulting in an increased expression of 5Htr3a receptors. Suitable DNA enhancers include, but are not limited to, for example, AkrRE1, AkrRE2, DLX binding site in (Zbtb16-5Htr3a), CALB1-DLX6 regulated enhancer 1, CALB1-DLX6 regulated enhancer 3, NPY-DLX6 regulated enhancer 1, NPY-DLX6 regulated enhancer 2, SST-Dlx6 regulated enhancer 1, homologous sequences thereof, or fragments thereof. In a preferably embodiment, the DNA regulatory elements are selected from the group consisting of SEQ ID NO:26, SEQ ID NO:29, SEQ ID NO:32, SEQ ID NO:35, SEQ ID NO:38, SEQ ID NO:41, SEQ ID NO:44, SEQ ID NO:47, SEQ ID NO:50, a homologous human sequence thereof.

In a further embodiment, the viral vectors may target other cells that endogenously express Ark1b10, for example liver cells.

As used herein, the term "gene" encompasses both protein-coding and non protein-coding genes. Thus, in one embodiment, the viral vector comprises at least one protein-coding gene. In another embodiment, the viral vector comprises at least one non protein-coding gene. The non protein-coding gene may encode an RNA. Thus, in one embodiment, the non protein-coding gene encodes a small interfering RNA (siRNA), a lncRNA, or an antisense RNA. Genes suitable for use in the present invention include, but are not limited to, those coding for the following: Akr1b8, Ark1b10, an agonist of Akr1b8, and an agonist of Akr1b10, Dlx6 and Evf2.

The present disclosure also provides a host cell containing a recombinant expression cassette or a recombinant expression vector according to an embodiment of the present disclosure. The host cell is either a prokaryotic or eukaryotic host cell. The host cell is capable of expressing the proteins or agonists of the present disclosure. Suitable host cells include, but are not limited to, mammalian cells and yeast cells. In some embodiments, the host cell is used to produce large quantities of the protein or agonist for use in the methods of the present disclosure.

Suitable agonists of either Akr1b10 or Akr1b8 can also be used in the methods of the present disclosure. Agonists of Akr1b10 or Akr1b8 include any chemical, protein or molecule that is able to elicit similar downstream activation of Akr1b10 or Akr1b8. In the present disclosure, an agonist of Akr1b10 or Akr1b8 would be able to elicit the increased expression of 5Htr3a receptor on one or more neuronal cells.

The "treating" or "treatment" of a neurological disorder, stress-induced condition or mood disorder includes, but is not limited to, reducing, inhibiting, alleviating or attenuating at least one or more symptoms of the neurological condition, stress-induced condition, or mood disorder.

The terms "effective amount" or "therapeutically effective amount" refer to an amount sufficient to effect beneficial or desirable biological and/or clinical results.

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

Neurological disorders or stress-induced conditions that can be treated by the methods provided herein include, but are not limited to, developmental neurological disorders, mood disorders, drug addiction, and the like. These disorders include, but are not limited to, for example, depression, anxiety disorder, panic disorder, obsessive-compulsive disorder (OCD), eating disorder, chronic pain, posttraumatic stress disorder (PTSD), epilepsy, drug addiction, and the like.

Many types of depression that may be treated by the methods of the disclosure include, but are not limited to, the three main types of clinical depression: major depressive disorder; dysthymic disorder; and bipolar depression, the depressed phase of bipolar disorder and any illness in which depression or depressive tendencies are a factor such as, inter alia, ADD (attention deficit disorder), ADHD (attention deficit hyperactivity disorder), Autism, anxiety, panic, bi-polar disorder, depression, GAD (generalized anxiety disorder), OCD (obsessive compulsive disorder), PTSD (post-traumatic stress disorder), Phobias, Schizophrenia, Convulsions, Anxiety, Depression, Mania, Manic-depression, Psychosis and other mood disorders. Within these types are variations in the number of associated mental symptoms, and their severity and persistence.

A subject experiencing major depressive disorder may suffer from, among other symptoms, a depressed mood or loss of interest in normal activities that lasts most of the day, nearly every day, for at least two weeks. Such episodes may occur only once, but more commonly occur several times in a lifetime. Dysthymic disorder, a chronic but less severe type or depression, unlike major depressive disorder, doesn't strike in episodes, but is instead characterized by milder, persistent symptoms that may last for years. Although it usually doesn't interfere with everyday tasks, people with this milder form of depression rarely feel like they are functioning at their full capacities. Bipolar disorder cycles between episodes of major depression, similar to those seen in major depressive disorder, and highs known as mania.

In some embodiments, the neurological disorder is a developmental neurological disorder. Developmental neurological disorders are impairments of the growth and development of the brain or central nervous system, including disorders of brain function that affect emotion, learning ability, self-control, and memory during growth and development. Suitable neurological developmental disorders include, but are not limited to, autism and autism spectrum disorders, Asperger's syndrome, fetal alcohol spectrum disorder, tic disorder, including Tourette's syndrome, attention deficit hyperactivity disorder, learning disabilities, schizophrenia, schizotypal disorder, addiction, and the like.

In some embodiments, the neurological disorder is a mood disorder. The mood disorder may include, but is not limited to, for example, major depressive disorder, unipolar major depressive episode, dysthymic disorder, treatment-resistant depression, bipolar depression, adjustment disorder with depressed mood, cyclothymic disorder, atypical depression, seasonal affective disorder, melancholic depression, psychotic depression, post-schizophrenic depression, depression due to a general medical condition, post-viral fatigue syndrome, chronic fatigue syndrome, and the like.

In another embodiment, the stress-related condition is selected from, but not limited to, posttraumatic stress disorder, acute stress disorder, adjustment disorder, bereavement related disorder, panic disorder, obsessive-compulsive disorder (OCD), eating disorder, chronic pain, posttraumatic stress disorder (PTSD), general anxiety disorder, social anxiety disorder, and anxiety disorder, due to a medical condition.

In some embodiments, the neurological disorder is epilepsy. In other embodiments the stress-induced condition is drug addiction.

In other embodiments, the present disclosure provides methods of increasing serotonin levels in a subject. The method comprises administering Akr1b10, Akr1b8 or an agonist of Akr1b10/Akr1b8 in an amount effective to increase the level of serotonin in the subject. In some embodiments, the increased serotonin levels are present in a subject suffering from a neurological disorder or stress-induced condition.

An increased level of serotonin in a subject may include, but is not limited to, an increase in serotonin levels of at least 5%, suitably at least 10%, alternatively at least 15%, alternatively at least 20% in the subject.

In further embodiments, the present disclosure provides a method of increasing expression of 5-hydroxytryptamine receptor 3A (5Htr3a) in at least one neuron, the method comprising contacting the at least one neuron with at least one of Akr1b8, an agonist of Akr1b8, Akr1b10, or an agonist of Akr1b10, wherein the at least one neuron has an increased expression of 5Htr3a on its surface. The Akr1b8, an agonist of Akr1b8, Akr1b10, or an agonist of Akr1b10 is provided in an effective amount to increase the expression of 5Htr3a on the surface of the neuron.

Not to be bound by any theories, it is believed that the increased expression of 5Htr3a on neurons leads to an increased level of serotonin signaling by the neuron. In turn, this increased signaling leads to a reduction or inhibition of one or more symptoms associated with the neurological disorder or stress-induced condition.

The term neuron includes interneurons. The interneurons may be found within the cortex of the brain of the subject. In some embodiments, the neuron is a human neuron.

The present disclosure further provides methods of inducing a pluripotent stem cell to differentiate into a neuron comprising culturing the pluripotent stem cell in the presence of at least one of Akr1b8, an agonist of Akr1b8, Akr1B10, or an agonist of Akr1B10, wherein the pluripotent stem cell differentiates into a neuron that expresses 5Htr3a on its surface. Suitable pluripotent stem cells include, but are not limited to, embryonic stem cells (ES cells) and induced pluripotent stem (iPS) cells. In some embodiments, the ES cell or iPS cell is a human cell. The method includes culture steps, conditions and medium to drive the ES or iPS cell toward neural differentiation which are known by one skilled in the art. Suitable culture steps can be found in, for example, Takahashi, K. and S. Yamanaka, Induction of pluripotent stem cells from mouse embryonic and adult fibroblast cultures by defined factors. Cell, 2006. 126(4): p. 663-76, the contents of which are incorporated by reference in its entirety. Akr1b8/b10 can be used in the recent trans-differentiation methods based on Yamanaka et al, Cell 2006, for example, methods as described in Ebert, A. D., et al., EZ spheres: a stable and expandable culture system for the generation of pre-rosette multipotent stem cells from human ESCs and iPSCs. Stem Cell Res, 2013. 10(3): p. 417-27; Hunsberger et al., Induced Pluripotent Stem Cell Models to Enable In Vitro Models for Screening in the Central Nervous System, *Stem Cells Dev* 2015 Aug. 15; 24(16):1852-64, Abranches E, Silva M, Pradier L, Schulz H, Hummel O, Henrique D, et al. (2009) Neural Differentiation of Embryonic Stem Cells In Vitro: A Road Map to Neurogenesis in the Embryo. PLoS ONE 4(7): e6286. doi:10.1371/journal.pone.0006286, the contents of which are incorporated by reference in their entirety.

In some embodiments, the compositions may be used to alleviate or reduce one or more symptom or sign associated with the mood disorder, including, but not limited to, depression and any illness in which depression or depressive tendencies are a factor such as, inter alia, ADD (attention deficit disorder), ADHD (attention deficit hyperactivity disorder), Autism, anxiety, panic, bi-polar disorder, depression, GAD (generalized anxiety disorder), OCD (obsessive compulsive disorder), PTSD (post-traumatic stress disorder), Phobias, Schizophrenia, Convulsions, Anxiety, Depression, Mania, Manic-depression, Psychosis, and other mood disorders.

Certain aspects of the present disclosure provide compositions which reduce or even substantially or completely diminish depression. In additional aspects, certain embodiments of the present disclosure provide methods leading to functional improvement after mood disorders or depressive events.

Further, the present disclosure provides methods and compositions for increasing the activation and regulation of 5Htr3a receptors by targeting the mevalonate pathway with small molecule effectors or metabolites of the mevalonate pathway.

Figure 14:
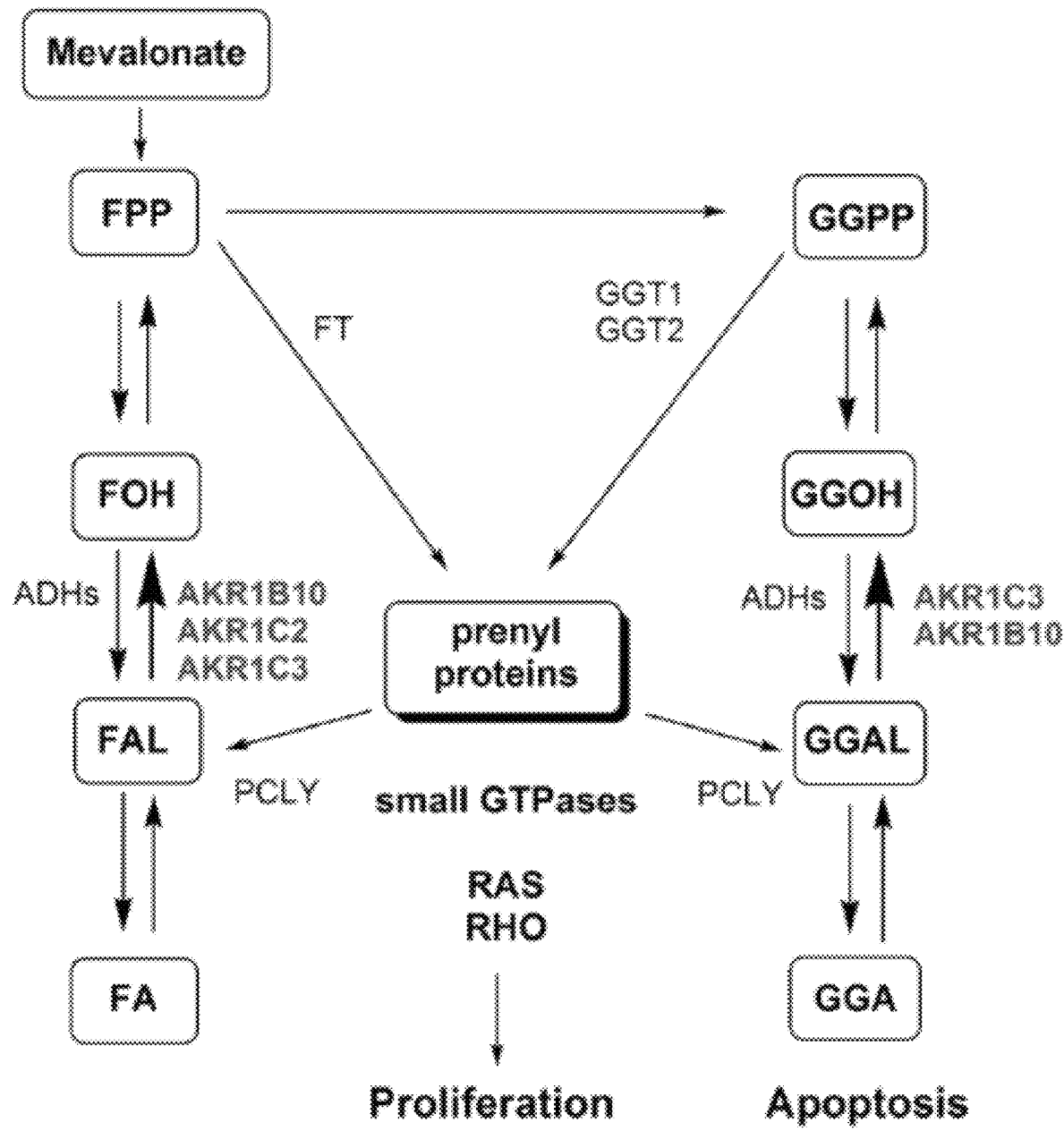
FIG. 14. A diagram depicting the role of AKR1B10 in the Mevalonate Pathway. Figure from Rizner 2012 ("Enzymes of the AKR1B and AKR1C subfamilies and uterine diseases", Frontiers in Pharmacology, vol. 3, Article 34, March 2012). AKR1B10, AKR1C3, and AKR1C1 catalyze the reduction of all-trans-retinal and 9-cis-retinal to their corresponding retinols, respectively. The reverse reaction is catalyzed by alcohol dehydrogenases (ADHs). Retinal is further oxidized by aldehyde dehydrogenases (ALDHs) to form retinoic acid, which by binding to the retinoic acid receptor (RAR) and the retinoid X receptor (RXR) stimulates cell differentiation. Retinoic acid is further metabolized by CYP26A to form 4-hydroxy-retinoic acid. (Adopted from Endo et. al., 2011.)
Figure 15:
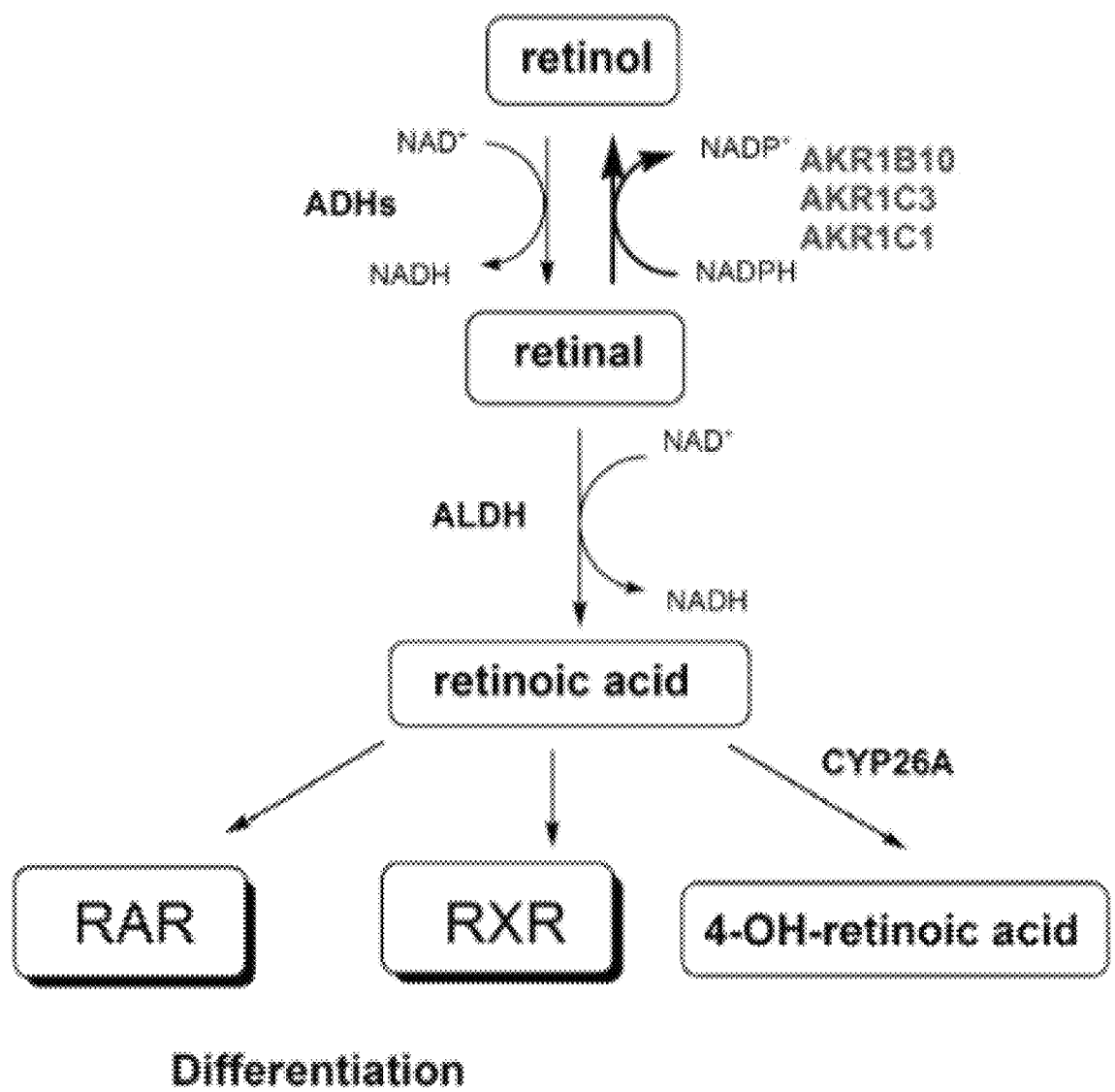
FIG. 15. A diagram depicting the implications of AKR1b and AKR1C enzymes in retinoid signaling. Figure from Rizner 2012. Prenylation involves transfer of farnesyl pyrophosphate (FPP) or geranylgeranyl pyrophosphate (GGPP) by farnesyl transerase (FT) and geranylgeranyl transferase 1 and 2 (GGT1 and GGT2), respectively, to various proteins including small GTPases (RAS and RHO). The reverse reaction that releases farnesal (FAL) and geranyl geranial (GGAL) is catalyzed by prenyl cysteinlyase (PCLY). Farnesyl pyrophosphate and geranylgeranyl pyrophosphate thus serve as substrates of FT and GGT1/GGT2 but can also be dephosphorylated to form farnesol (FOH) and geranylgeranyol (GGOH). FOH and GGOH are oxidized to FAL and GGAL by alcohol dehydrogenases (ADHs) and by yet unidentified enzymes to farnesoic acid (FA), geranylgeranoic acid (GGA) and other metabolites. The reduction of FAL and GGAL to FOH and GGOH is catalyzed by AKR1B and AKR1C enzymes. This reaction indirectly recovers substrates for further formation of active prenyl pyrophosphates. Additionally, reduction of GGAL to GGOH prevents formation of GGA and the metabolites with potential apoptotic effects. (Adopted from Endo et. al., 2011.)

A further embodiment provides a method of treating a neurological disorder or stress-induced disorder, the method comprising: administering a small molecule effector or metabolite of the mevalonate pathway, wherein administration of the small molecule effector or metabolite alleviate, reduce or inhibit at least one symptom of the neurological disorder or stress-induced disorder. The mevalonate pathway is shown in FIGS. 14 and 15 and is described in Rizner et al. 2012, the contents of which are incorporated by reference in its entirety. The ability to modulate the mevalonate pathway with AKR1b10/1b8 allows for the treatment of a neurological disorder, stress induced disorder, and other suitable disorders, including additional small molecule effectors or metabolites that directly alter the mevalonate pathway. For example, in some embodiments, the small molecule effectors of the mevalonate pathway include, but are not limited to, e.g. FOH, GGOH, antisense RNA regulators of Akr1b10 and Evf2.

Aspects of the disclosure described with respect to the former method can be applicable to the latter method, and vice versa, unless the context clearly dictates otherwise.

The methods disclosed herein can include a conventional treatment regimen, which can be altered to include the steps of the methods described herein. The methods disclosed herein can include monitoring the patient to determine efficacy of treatment and further modifying the treatment in response to the monitoring. The methods disclosed herein can include administering a therapeutically effective amount of Akr1b10, Akr1b8, an agonist of Akr1b10, or an agonist of Akr1b8.

In some embodiments, compositions for use in carrying out the method claims are provided. Suitable compositions comprise an effective amount of Akr1b10, Akr1b8, an agonist of Akr1b10, or an agonist of Akr1b8, and a pharmaceutically acceptable carrier.

The term "pharmaceutically acceptable carrier" refers any carrier, diluent or excipient which is compatible with the other ingredients of the formulation and not deleterious to the recipient.

The active agent is preferably administered with a pharmaceutically acceptable carrier selected on the basis of the desired route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, but are not limited to, for example, tablets, capsules, solutions, parenteral solutions, troches, suppositories, or suspensions.

For oral administration, the active agent may be combined with one or more solid inactive ingredients for the preparation of tablets, capsules, pills, powders, granules or other suitable oral dosage forms. By way of example only, the active agent may be combined with at least one excipient, including, but not limited to, fillers, binders, humectants, disintegrating agents, solution retarders, absorption accelerators, wetting agents absorbents or lubricating agents.

For parenteral administration, the active agent may be mixed with a suitable carrier or diluent, including, but not limited to, water, an oil (e.g., a vegetable oil), ethanol, saline solution (e.g., phosphate buffered saline or saline), aqueous dextrose (glucose), and related sugar solutions, glycerol, or a glycol such as propylene glycol or polyethylene glycol. Stabilizing agents, antioxidant agents and preservatives may also be added. Suitable antioxidant agents include, but are not limited to, sulfite, ascorbic acid, citric acid and its salts, and sodium EDTA. Suitable preservatives include, but are not limited to, benzalkonium chloride, methyl- or propyl-paraben, and chlorbutanol. The composition for parenteral administration may take the form of an aqueous or nonaqueous solution, dispersion, suspension, or emulsion.

The composition is preferably in unit dosage form. In such form the preparation may be divided into unit doses containing appropriate quantities of the active component. The unit dosage form may be a packaged preparation, the package containing discrete quantities of preparation, such as, but not limited to, packeted tablets, capsules, and powders in vials or ampoules. Also, the unit dosage form may be a capsule, tablet, cachet, or lozenge itself, or it can be the appropriate number of any of these in packaged form.

The present invention has been described in terms of one or more preferred embodiments, and it should be appreciated that many equivalents, alternatives, variations, and modifications, aside from those expressly stated, are possible and within the scope of the invention.

The invention will be more fully understood upon consideration of the following non-limiting examples.

Example 1: Evf2 Enhances lncRNA Functionally and Spatially Organizes Megabase Distant Genes in Developing Forebrain Gene regulation requires selective targeting of DNA regulatory enhancers over megabase (Mb) distances. Here, Applicant shows that Evf2, a Dlx5/6 ultraconserved enhancer (Dlx5/6UCE) lncRNA, regulates genes that are asymmetrically-positioned across 27 Mb. Evf2 localizes to both activated (Umad1, ~1.6 Mb distant) and repressed (Akr1b8, 27 Mb distant) targets in mouse developing forebrain, controlling distances between Dlx5/6UCE and transcriptional targets in interneuron subpopulations. Through both short-range (Dlx6 anti-sense) and long-range (Akr1b8) repression, the Evf2-5'UCE region regulates multiple interneuron subtype genes, linking the mevalonate pathway and interneuron development. Surprisingly, Evf2 regulates the number and position of hundreds of Dlx5/6UCE-chr6 interaction sites across chr6 (~150 Mb), without affecting transcription. Active histone lysine modifications distinguish Evf2 positively- and negatively-regulated Dlx5/6UCE-chr6 sites, supporting that many sites are marked before Evf2 regulation. These studies reveal that an autosomal cloud-forming enhancer lncRNA regulates genes through antisense and chromosome topological mechanisms, and also controls the 3-D architecture of an entire chromosome.

Enhancers are defined as DNA sequences capable of regulating genes at a distance, independent of orientation. Early studies show regulatory interactions between the sonic hedgehog (Shh) limb enhancer (ZRS) and the Shh gene, despite a 1 Mb distance (Anderson et al., 2014; Lettice et al., 2003). Technological advances in understanding chromosome topology (Dekker, 2016) reveal that the majority of promoter interactions (~93%) are distal, rather than proximal (de Laat and Duboule, 2013; Sanyal et al., 2012). In addition, validated enhancer regulatory landscapes in vertebrates span ~1 Mb, and facilitate tissue-specific and/or developmentally programmed gene expression. Colinearity is an elegant example of enhancer regulatory landscapes that contain functionally and spatially organized HoxA and HoxD genes involved in body patterning (Kmita and Duboule, 2003). HoxD genes located at the borders of topological domains are subject to a developmentally-dependent switch in domain regulation, providing a mechanism for HoxD gene colinearity in vertebrate limbs (Andrey et al., 2013). However, many enhancer regulatory landscapes organize megabase distant genes, and therefore, enhancer-dependent, selective regulation of genes over long distances remains a fundamental question in biology.

Applicant's work on Evf2, a spliced and polyadenylated enhancer lncRNA (Feng et al., 2006) indicated that Evf2 is transcribed from Dlx5/6UCE (Zerucha et al., 2000), and regulates Dlx5/6UCE activity in trans (Feng et al., 2006).

Evf2 is expressed at sites of interneuron birth in mouse embryonic forebrain (E13.5 medial and caudal ganglionic eminences [MGE, CGE]), recruits transcription factors to the Dlx5/6UCE (Bond et al., 2009), forms a large DLX1 homeodomain containing ribonucleoprotein complex (Evf2-RNP), and directly inhibits BRG1(SMARCA4) ATPase and chromatin remodeling activities (Cajigas et al., 2015). In adult mice, Evf2 loss causes GABAergic circuitry defects, supporting enhancer lncRNA biological significance (Bond et al., 2009).

Evf2 forms one-two RNA clouds per nucleus in developing interneurons (Feng et al., 2006), similar to clouds described for imprinting and dosage compensation lncRNAs (Brockdorff, 2011; Redrup et al., 2009). While the dosage compensation lncRNA Xist controls chromosome-topology across the inactivated X-chromosome (Giorgetti et al., 2016; Nora et al., 2012), evidence supporting chromosome-wide effects of autosomal lncRNAs is lacking. This Example demonstrates that Evf2 targets Dlx5/6UCE interactions to sites across chr6 (~150 Mb), but affecting gene expression only across a ~27 Mb region. These interactions extend beyond the limitation of ~1 Mb for the majority of enhancer regulatory landscapes. Thus, in addition to antisense regulation, these data support biologically significant, instructive and permissive roles of an enhancer lncRNA through control of chromosome topology.

Results

The Evf2-5' Enhancer-Containing Region Regulates Interneuron Subtype Genes

GABAergic interneurons in the adult brain display the greatest diversity of any cell type, partly due to expression of interneuron subtype specific genes (DeFelipe et al., 2013). In mice, Dlx homeodomain transcription factors, originally identified by homology to fly dll play critical roles throughout interneuron development, from their birth and migration in the GE's (Anderson et al., 1997; Price et al., 1991), to adult activity-dependent maturation (De Marco Garcia et al., 2011). In mouse GE's, Shh induces GABAergic interneuron specification, activating Dlx's, Evfs, and an embryonic form of glutamate decarboxylase 1 (Gad1), the rate-limiting enzyme in GABA production (Feng et al., 2006; Kohtz et al., 1998). While embryonic Shh and Dlx genes contribute to interneuron diversity (Cobos et al., 2005; Long et al., 2007; Xu et al., 2010), the role of Evf2 has not been shown.

Using mice lacking Evf2 (Evf2$^{TS/TS}$ (Bond et al., 2009), transcription stop insertion (TS) in Evf exon 1, Evf2$^{TS}$, FIG. 1A), the effects of Evf2 loss on interneuron subtype gene expression in MGE were determined. Evf2 activates and represses interneuron subtype genes in MGE, with greater than two-fold changes in serotonin receptor 3a (5Htr3a), and subtle changes in calbindin 1 (Calb1), neuropeptide Y (Npy), and somatostatin (Sst, Som) (FIG. 1B). While Sst and 5Htr3a constitute two of the three major interneuron subclasses (Rudy et al., 2011)), parvalbumin, which marks the third major interneuron class, and other interneuron subtype genes (vasoactive intestinal peptide (VIP) and calretinin) are not expressed this early in development (not shown).

Figures 6A, 6B, 6C, 6D:
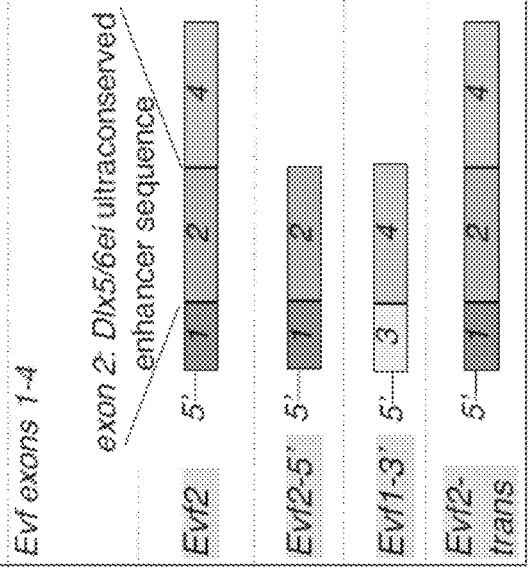
FIG. 6A-D. Evf2-chr6-targets and interneuron subtype gene expression: dose-dependence and differential roles of the Evf2-5'UCE region, 3' end and trans effects. A. Table summarizing necessary and sufficient regulatory roles of different Evf lncRNA spliced forms in E13.5 MGE. Evf exons are labeled (1-4), repressed genes (red), and activated genes (green). Pink Star: correlation between repressed targets and interneuron subtype gene regulation. B. Taqman E13.5 MGE qRT-PCR analysis from 6 different mouse mutants, where maternal (m), and paternal (p) alleles are indicated: Evf2TSm/+p, EVf2TSp/+m, Evf2TS/TS, Dlx5/6KOm/TSp, Dlx5/6KOp/TSm, Evf1TS/TS. Correlations between Evf2/Evf2-chr6 target genes (Evf2, Dlx5, Dlx6, Umad1, Lsm8, Rbm28, Akr1b8), and Gad1/interneuron subtype genes (Gad1, Calb1, Npy, Som, 5Htr3a), reveal dose dependent relationships for 4/35 gene pairs. X-axis-Evf2-chr6 target genes, Y-axis-interneuron subtype genes: Dlx6: Calb1 (r2=0.81), Lsm8:Npy (r2=0.95), Umad1:5htr3a (r2=0.93), Umad1: Som(Sst) (r2=0.86), n=4-7 of each genotype (individuals analyzed for Evf2TS/TS and Evf1TS/TS, pooled values for Evf2TSm/+p, Evf2TSp/+m, Dlx5/6KOm/TSp, Dlx5/6KOp/TSm. Values are normalized to +/+ littermates. Schematics for each genotype are shown on the right. C. Taqman E13.5 MGE qRT-PCR analysis from Dlx5/6KO/TS showing genetic rescue of Dlx5/6 rescues effects on interneuron subtype genes, normalized to Dlx5/6+/Evf2+ littermates, n=4 each genotype, Student's E.-test, ***p<0.001, D. Evf2-regulated histone lysine methylation (H3K4me3) changes in promoter regions of interneuron subtype genes (Calb1, Npy, Som/Sst1). UCSC browser profiles of anti-H3K4me3, native ChIPseq results compare profiles in Evf2+/+ and Evf2TS/TS E13.5 GE chromatin. Despite subtle changes in (<2-fold), IDR-MACS2 peaks are indicated by black tracks, where darker bars indicate higher peak densities (black>grey). MACS2 identities differential peaks (pink tracks), expressed in −log 10(p-value). Computationally predicted enhancer sites are indicated at the top (Enhancers mm9; FANTOM, UCSC).
Figures 6A, 6B, 6C, 6D:
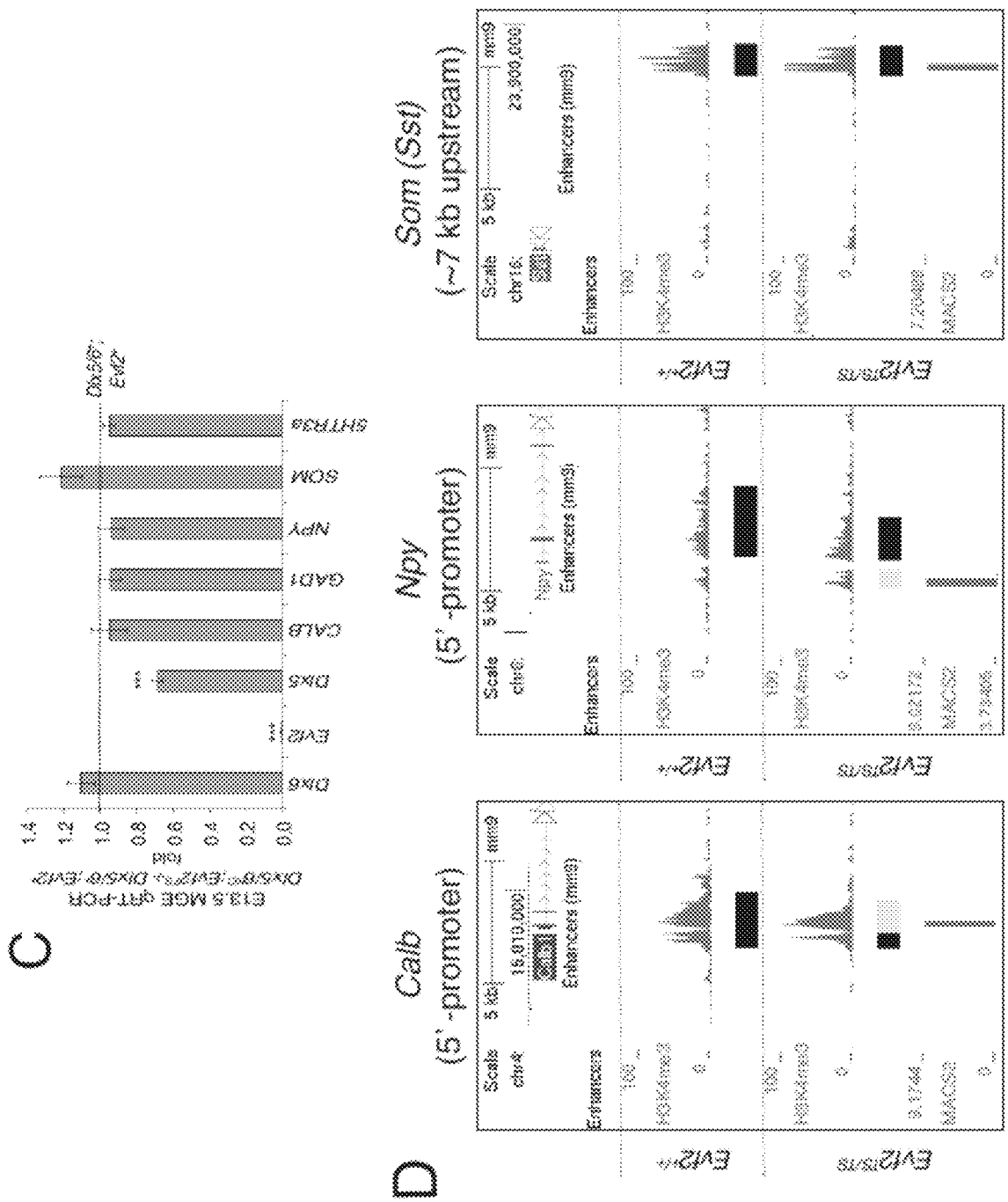

In order to distinguish between the roles of Evf2-5' (UCE-containing) from Evf2-3' (UCE-lacking) regions, Evf1$^{TS/TS}$ mice were generated (inserting TS into Evf exon 3, Evf1$^{TS}$, FIG. 1A). Evf1$^{TS}$ insertion truncates Evf2, generating an enhancer-containing form (Evf2-5), and preventing transcription of Evf1 (FIG. 1C). Evf2-5' retains enhancer transcription and Dlx6 anti-sense transcription, the latter consistent with the finding that Dlx6 expression does not change in Evf1$^{TS/TS}$ (FIG. 1C). However, similar to Evf2$^{TS/TS}$, Dlx5 is increased in Evf1$^{TS/TS}$ (FIG. 1C). Therefore, Evf2-5' is both necessary and sufficient for Dlx6 repression, while Evf2-3' is required for Dlx5 repression. In Evf1$^{TS/TS}$, interneuron subtype gene expression is not affected (FIG. 1D). Given that Evf1 continues to be expressed in Evf2$^{TS/TS}$ (Bond et al., 2009), Evf1 is not sufficient to regulate interneuron subtype genes in Evf2$^{TS/TS}$MGE. Therefore, Evf2 truncation, rather than Evf1 loss is responsible for interneuron subtype gene regulatory differences between Evf1$^{TS/TS}$ and Evf2$^{TS/TS}$ (FIG. 6, pink star). Analysis of Evf2$^{TS/TS:R}$ MGE indicates that Evf2 expressed from a transgene at ~38% wildtype levels (Berghoff et al., 2013) does not rescue interneuron subtype genes (FIG. 1E), supporting that the Evf2-5' enhancer-containing region controls interneuron subtype gene expression through cis-mechanisms. The combined genetic data indicates that the Evf2-5' enhancer-containing region is both necessary and sufficient for regulating Dlx6 and interneuron subtype genes.

Evf2 Activates and Represses Asymmetrically Positioned Genes Across 27 Mb

In order to identify genes involved in Evf2-dependent regulation of interneuron subtype genes, Applicant compared gene expression between Evf2$^{+/+}$ and Evf2$^{TS/TS}$ MGE using microarray analysis (FIG. 10, validated targets, FIG. 11, complete list). Microarray analysis indicates that the majority of validated targets are located on mouse chr6 (Evf2-chr6 targets) (FIG. 10). With the exception of overlapping Dlx6 (anti-sense), Evf2-chr6 target genes are organized asymmetrically, 5' of the Evf2 transcription start site, across 27 Mb (FIG. 1A). Evolutionarily conserved organization of 5/6 of the Evf2-chr6 target genes in human chr7 supports a potentially significant biological role (FIG. 1A). Asymmetric positioning of Evf2-chr6 targets and synteny with human chr7 led to further focus on the significance and mechanism of Evf2-chr6 target gene regulation.

Evf2-5'UCE Represses Dlx6, Rbm28, and Akr1b8

In addition to repressing Dlx5 and Dlx6, as shown previously (Bond et al., 2009)), Evf2 represses long-range targets Rbm28 and Akr1b8, and activates long-range targets Umad1 and Lsm8 (FIG. 1A, 1F, FIG. 10). Comparisons of Evf2-chr6 targets in Evf2$^{TS/TS}$ and Evf1$^{TS/TS}$ MGE show that Evf2-5' is both necessary and sufficient for Rbm28 and Akr1b8 repression, while Evf2-3' is required for Umad1 and Lsm8 activation (FIG. 1F, G). Therefore, Evf2 repression of Dlx6 and long-range targets requires the Evf2-5'UCE region, while activation requires the Evf2-3' region. In Evf2$^{TS/TS}$, partial rescue of Lsm8 supports Evf2-dependent trans-activation of at least one Evf2-chr6 long-range target gene.

Figures 1A, 1B, 1C, 1D, 1E, 1F, 1G, 1H, 1I, 1J, 1K:
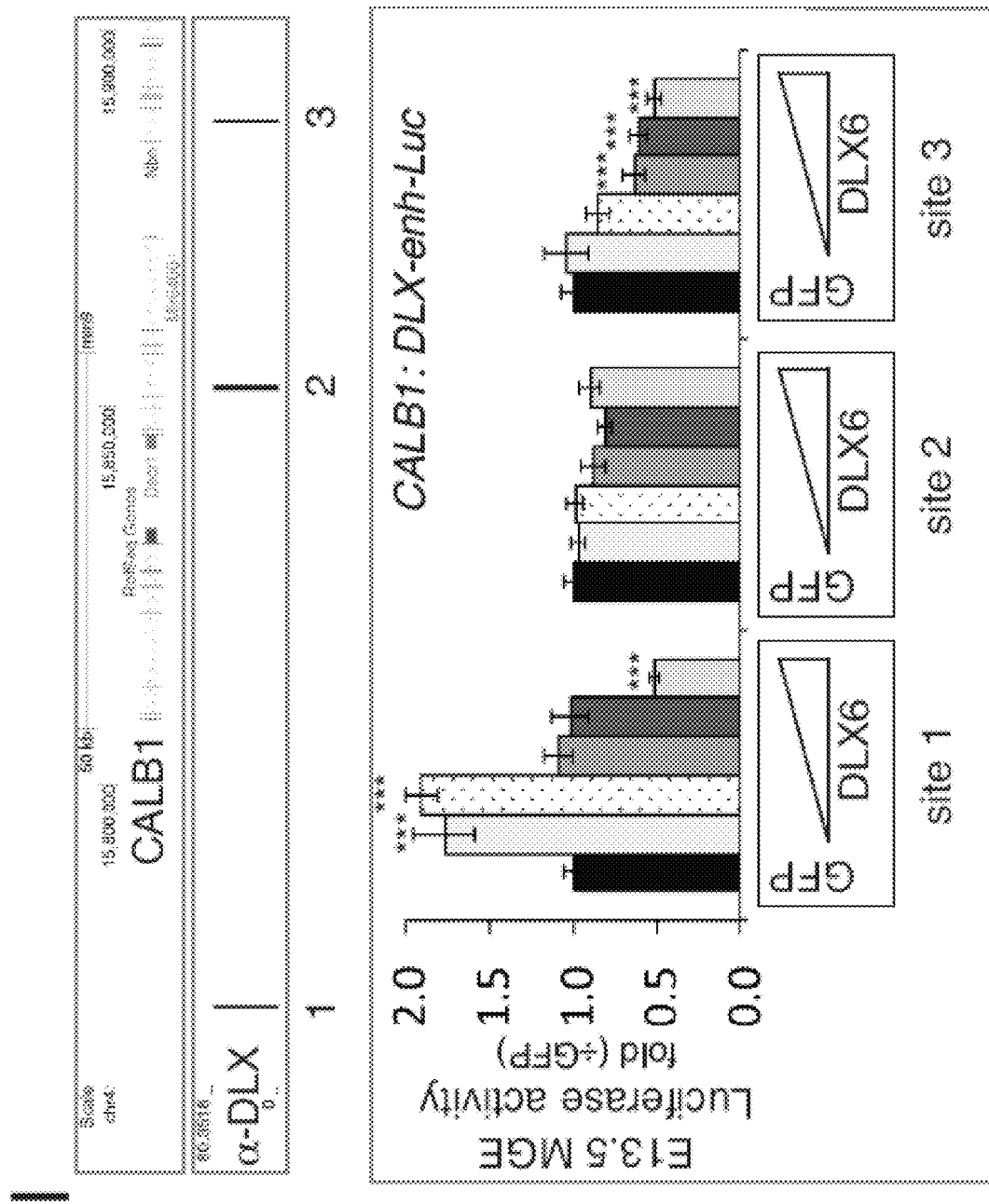

Gene expression analysis correlates Evf2-5' repression of Evf2-chr6 targets (Dlx6, Rbm28, Akr1b8) with regulation of interneuron subtype gene expression (FIG. 1, compare B, D, compare F, G). FIG. 6A summarizes the relative roles of the Evf2-5' UCE region, 3' end, and trans effects on Evf2-chr6 targets and interneuron subtype genes, highlighting the correlation between Dlx6, Rbm28, Akr1b8 repression and interneuron subtype gene regulation (pink star).

The Evf2-Antisense Target Dlx6, Regulates Multiple Interneuron Subtype Genes

Using a genetic approach, Applicant next analyzed gene expression from 6 mouse mutants with different combinations of Evf2$^{TS}$, Evf1$^{TS}$ and Dlx5/6$^{KO}$ (Merlo et al., 2002) alleles (FIG. 6B, 6C). In Dlx5/6$^{KO}$; Evf2$^{TS}$ mice, rescue of Dlx6 and Dlx5, also rescues interneuron subtype gene effects (FIG. 6C). Furthermore, 4/35 possible dose-dependent relationships between five interneuron subtype and seven Evf2-chr6 target genes are detected at an $r^2 > 0.8$, including Dlx6 and Calb1 ($r^2$=0.81) (FIG. 12). In order to test whether Dlx6 dosage directly regulates Calb1 expression, Applicant used anti-DLX ChIPseq to identify potential enhancers in E13.5GE, and found three DLX binding sites within ~50 kb of the Calb1 gene (FIG. 1I). Transfection into primary cultures of MGE shows that Dlx6 dosage regulates Calb1-enhancers (sites 1 and 3) in luciferase reporter assays (FIG. 1I). Anti-DLX ChIPseq identifies DLX binding sites near Npy and Sst genes, also regulated by Dlx6 in a dose-dependent manner (FIG. 1J, K). Thus, Dlx6 activates and represses multiple interneuron subtype enhancers (5/6 tested), supporting that Dlx6 dosage contributes to interneuron diversity as early as E13.5. These data support that Evf2 repression of Calb1 and activation of Npy and Sst occur through Dlx6 antisense regulation.

Figures 2A, 2B, 2C, 2D, 2E, 2F, 2G, 2H, 2I, 2J:
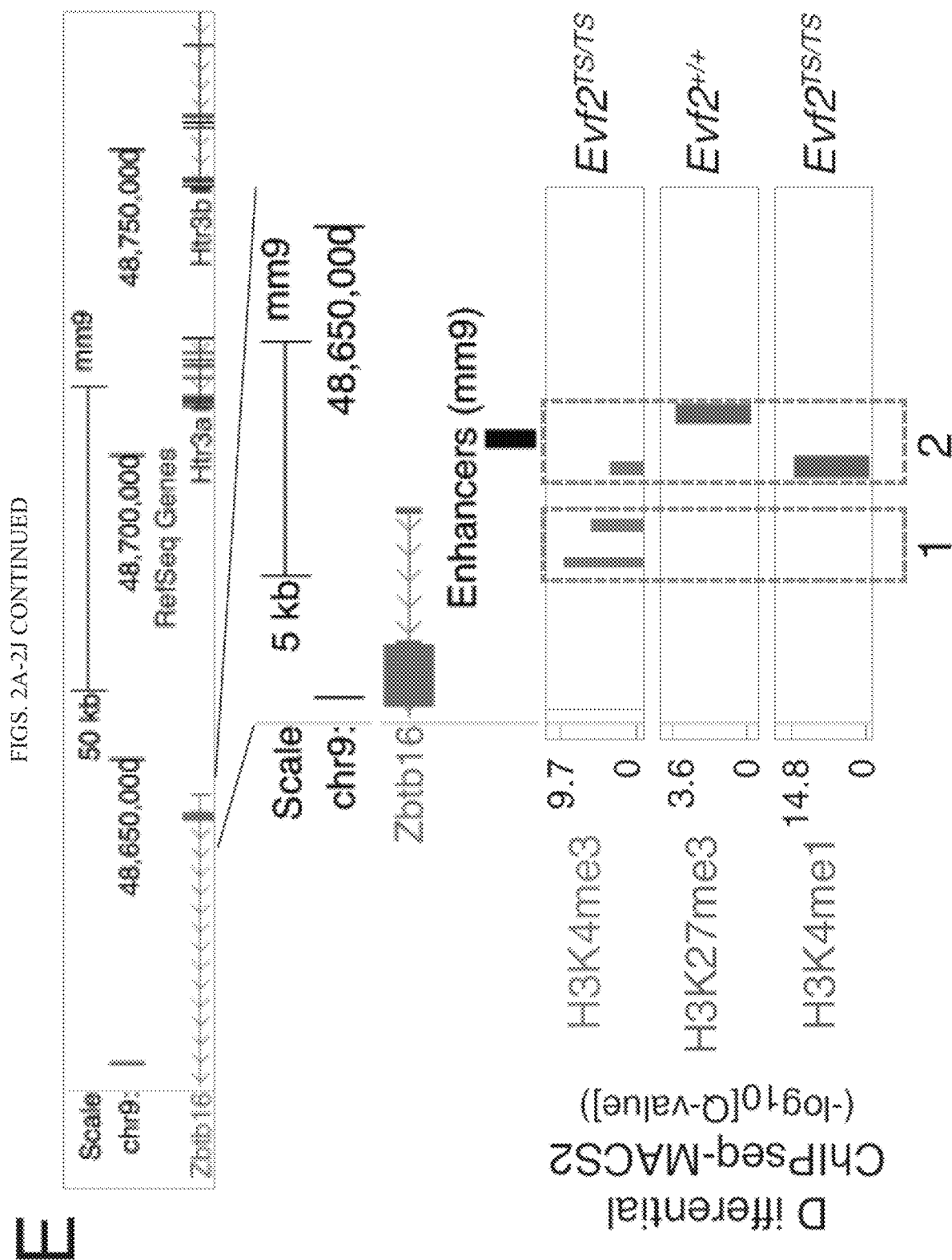
FIG. 2A-J. The Evf2-Akr1b8-5Htr3a axis: Akr1b8 and mevalonate pathway-regulated enhancers in the Zbtb16-5Htr3a region. A, B. qRT-PCR analysis of CGE, Evf2$^{TS/TS}$ normalized to Evf2$^{+/+}$, red: repressed genes, green: activated genes and grey: independent genes. A. interneuron subtype genes and glutamate decarboxylase gene 1 (Gad1), B. Evf2-chr6 target genes, C. qRT-PCR analysis of CGE Evf2$^{TS/TS}$; Akr1b8$^{-/-}$ normalized to Evf2$^{TS/TS}$; Akr1b8$^{+/+}$. CGE (Akr1b8, Sst, 5Htr3a), n=6-15 of each genotype. D. qRT-PCR of Akr1b8 or 5Htr3a expression in primary CGE transfected with Akr1b8 (pCMV6-Akr1b8, grey bars), normalized to GFP transfected with GFP (pCMV-GFP, black bars). n=3-6. E. UCSC Browser display of Zbtb16-Htr3a/b (5Htr3a/b) region, and differential H3Kme (ChIP-seq-MACS2, purple bars) in the promoter region of Zbtb16 of Evf2$^{-/-}$ vs Evf2$^{TS/TS}$ GE, identifies potential Akr1b8-regulated enhancers (AkrRE1/2). F-J. Regulation of AkrRE1/2 in luciferase reporter assays, using primary CGE and MGE cells. F. Akr1b8 regulation of individual enhancers AkrRE1 (1) and AkrRE2 (2), normalized to GFP expression. G-J. Dosage effects of mevalonate pathway metabolites FOH and GGOH (grey bars) on AkrRE1/2 luciferase reporters, normalized to buffer alone (−, black bars). Triangles indicate increasing concentrations (FOH: 0.1, 1, 10, or 100 µM, GGOH: 0.01, 0.1, 1, 10, or 100 µM). G-H. CGE, n=10, and I-J. MGE. n=12/condition, averaged from two experiments, Student's t-test, *p<0.05, p<0.01, *p<0.001, error bars (S.E.M).
Figures 2A, 2B, 2C, 2D, 2E, 2F, 2G, 2H, 2I, 2J:
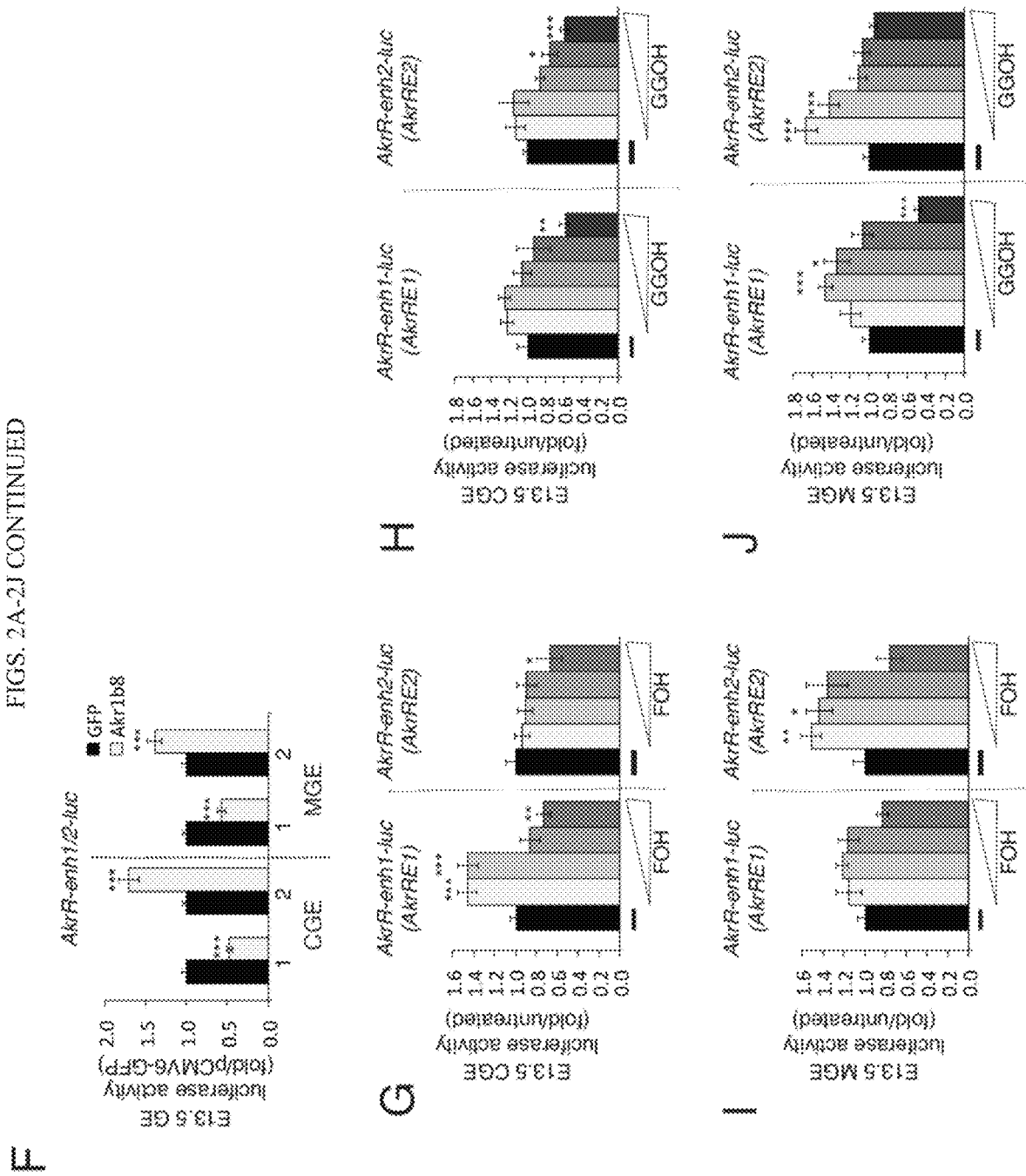

Regional Control of the Evf2-Akr1b8-5Htr3a Axis Involves the Mevalonate Pathway and Akr1b8 Regulated Enhancers Morphologically and molecularly distinct lateral, medial and caudal ganglionic eminences (LGE, MGE and CGE, FIG. 7A) are sites of interneuron birth in the embryonic brain, and contribute to interneuron diversity (Gelman and Marin, 2010; Nery et al., 2002; Waclaw et al., 2010; Wichterle et al., 2001). Given that the CGE is a major source of 5Htr3a-expressing interneurons (Rudy et al., 2011), Applicant next analyzed Evf2- gene regulation in CGE. Analysis of interneuron subtype gene expression profiles in Evf2$^{TS/TS}$ CGE shows that both Sst and 5Htr3a increase, with no effects on Calb or Npy levels (FIG. 2A). However, Evf2-chr6 targets show a similar profile of activation and repression compared to MGE (compare FIG. 1F and FIG. 2B), with two exceptions: (1) subtle Dlx5 repression is not observed in CGE, (2) Akr1b8 repression is greater in CGE (~15-fold) compared to MGE (~7-fold).

Therefore, although Evf2 regulation of Evf2-chr6 targets is similar in MGE and CGE, interneuron subtype gene expression differs for all four interneuron subtype genes as follows: (1) Evf2 represses Calb in MGE, but not CGE, (2) Evf2 activates Npy in MGE, but not CGE, (3) Evf2 activates Sst and 5Htr3a in MGE, but represses Sst and 5Htr3a in CGE (compare FIGS. 1B and 2D). Together, these data show that Evf2 control of interneuron subtype gene expression in embryonic brain is regionally regulated, depending on MGE or CGE origin.

Applicant next determined whether correlations between Akr1b8 and 5Htr3a, the most highly regulated Evf2-chr6 target and interneuron subtype gene, respectively, reflect direct regulation. Although the loss of Akr1b8 (Akr1b8$^{-/-}$) does not affect interneuron subtype gene expression in CGE (FIG. 7B), loss of Akr1b8 from Evf2$^{TS/T}$ partially rescues 5Htr3a levels in Evf2$^{TS/TS}$; Akr1b8 double homozygote CGE (FIG. 2C). Thus, Evf2 represses 5Htr3a, in part, through Akr1b8 repression in CGE. Furthermore, Akr1b8 transfection into CGE primary cultures increases endogenous Akr1b8 and 5Htr3a levels (FIG. 2D). Differential analysis of ChIP-seq peaks identifies Evf2-dependent changes in H3K4me3 (active promoters), H3K27me3 (silent chromatin), and H3K4me1 (enhancers) in two regions located at the Zbtb16 5' end (~63 kb downstream of the 5Htr3a gene, FIG. 2E, FIG. 7). Evf2 decreases active marks (H3K4me3, sites 1/2 and H3K4me1, site 2), and increases repressive mark (H3K27me3 at site 2), FIG. 2E, purple bars indicating sites of statistically significant enrichment. Co-transfection of Akr1b8 with site 1 or site 2 luciferase reporters into primary CGE and MGE shows that Akr1b8 represses Akr1b8-regulated enhancer 1 (AkrRE1) and activates AkrRE2, indicating site-dependent effects (FIG. 2F).

As part of the mevalonate pathway, Akr1b8 controls farnesol (FOH) and geranylgeraniol (GGOH) levels, affecting protein prenylation (Endo et al., 2011), and can also convert all-trans-retinaldehyde to retinol (Gallego et al., 2007). However, given the lack of evidence to support the involvement of retinoids in Evf2 regulation, (FIGS. 10 and 11) and FIG. 7C, Applicant tested the involvement of mevalonate pathway metabolites in AkrRE1/2 regulation. In CGE and MGE, FOH and GGOH display dose-dependent, enhancer- and region-specific effects (FIG. 2G-J). These data support the idea that the Evf2-Akr1b8-5Htr3a axis involves regionally controlled mevalonate pathway regulation of enhancers located downstream of 5Htr3a in developing brain. While Akr1b8 (AKR1B10 in human) belongs to a large family of aldo-keto reductases with links to diabetes and cancer (Penning, 2015), roles in neuronal development or brain circuitry have not been reported. These studies are significant as they reveal a novel pathway for modulating 5Htr3a in neurons, and also demonstrate the potential for signaling pathway identification through studies of enhancer lncRNA gene regulation in vivo.

Figures 3A, 3N:
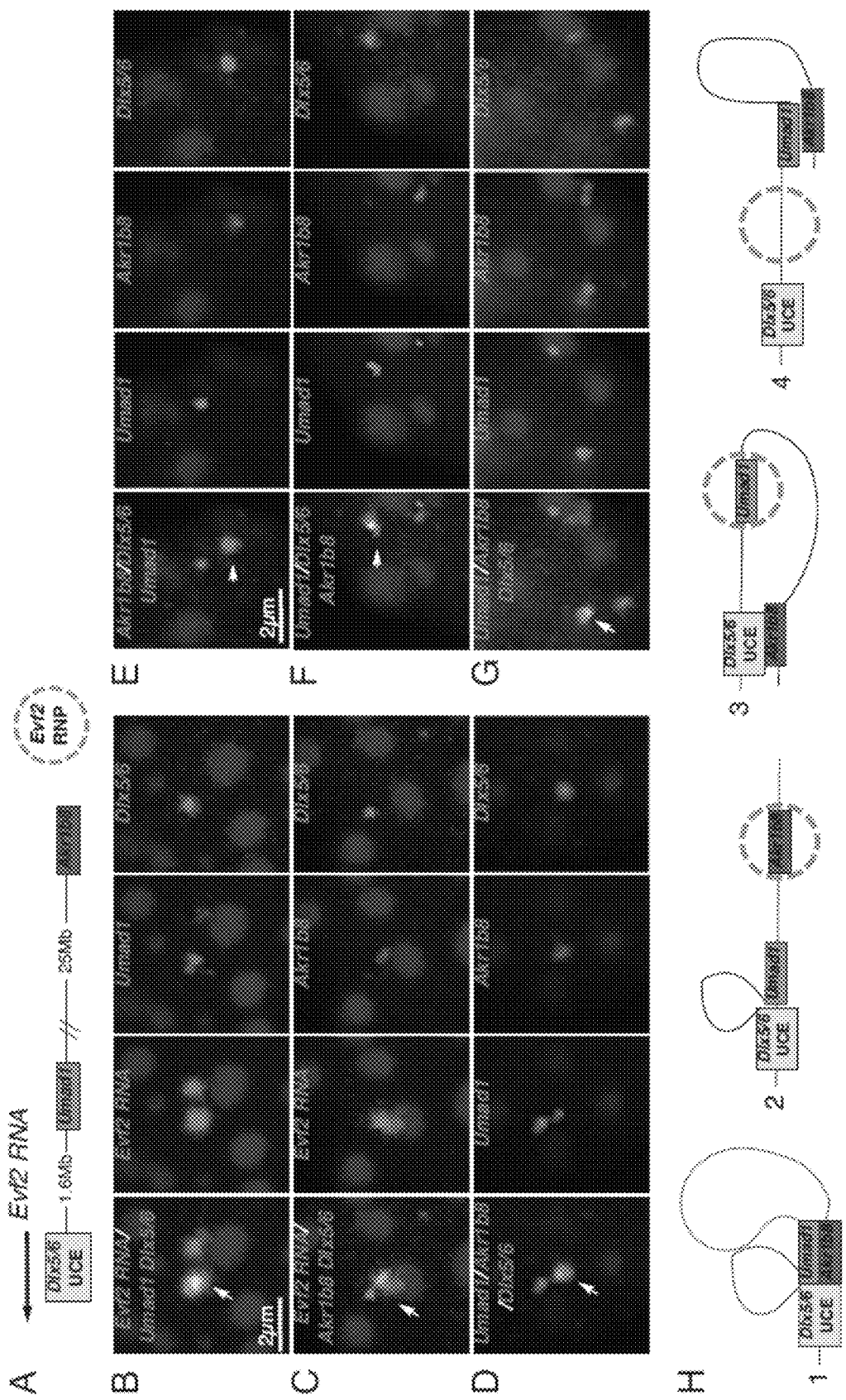
FIG. 3A-N. Evf2 RNA cloud associates with Umad1 and Akr1b8, and regulates Dlx5/6 UCE-Umad1-Akr1b8 distances in interneuron subpopulations. A. A schematic showing the distances between Dlx5/6UCE (yellow), Umad1 (green, activated target gene), Akr1b8 (red, repressed target gene), direction of Evf2 lncRNA transcription, formation of the Evf2 RNA cloud (green dashed circle). B-C. Fluorescent in situ hybridization (FISH) of GE nuclei probed with anti-sense Evf2 RNA (green), and DNA probes, as indicated. White arrows indicate co-localization of Evf2 RNA cloud and target genes. D-G. DNA FISH of GE nuclei showing examples of Dlx5/6UCE-gene interactions. H. Schematics summarizing Evf2 RNA cloud localization and Dlx5/6UCE-Umad1 Akr1b8 interactions. I-N: Comparison of distances between Dlx5/6UCE-Umad1 Akr1b8 in Evf2$^{+/+}$ and Evf2$^{TS/TS}$ GE nuclei (n=83, each genotype), I-K. Gene distances from single nuclei binned in 8 groups (<0.2 µm->2 µm), and percentages of nuclei in each bin plotted. Chi-square ($\chi^2$, (*p<0.05), degrees of freedom (df=7), Evf2$^{+/+}$ (black bars) Evf2$^{TS/TS}$, Evf2$^T$ density plot of gene distances shows greater density of Evf2$^{TS/TS}$ nuclei (blue) outside of main cluster Evf2$^{+/+}$ nuclei (red). M, N. Self-organizing maps (SOMs) in the Matlab neural network toolbox (NNT) and three training iterations optimally cluster gene-distance data and visualization. M. Neighbor weight distance SOMs show that ~2-fold more Evf2$^{+/+}$ nuclei clusters Evf2$^{+/+}$ are connected by closer distances (yellow hexagons) compared to Evf2$^{TS/TS}$, N. Weight position SOMs provide a 3-D visualization of connections between Evf2$^{+/+}$ (orange) and Evf2$^{TS/TS}$ (blue) centroids.

Evf2 Regulates Dlx5/6UCE-Umad1-Akr1b8 Chromosome Topology in Interneuron Subpopulations Asymmetric positioning of Evf2-chr6 targets across 27 Mb raised the possibility that chromosome topological mechanisms are involved in Evf2 long-range gene regulation. Applicant used Evf2 RNA/DNA fluorescence in situ hybridization (FISH) in E13.5GE nuclei, to investigate the relationship between Evf2 RNA cloud, Dlx5/6UCE, and long distance targets Akr1b8 and Umad1 (an activated target gene located at -1.6 Mb distance) (FIG. 3A). While Evf2 RNA clouds (one or two clouds/nucleus) localize with Akr1b8 or Umad1 (FIG. 3B, C), Evf2 RNA clouds do not appear to co-localize with Dlx5/6UCE (0/50 nuclei). DNA FISH analysis of Umad1-Akr1b8-Dlx5/6UCE detects all possible co-localization relationships (FIG. 3D-G). Based on Evf2 RNA/2-probe DNA FISH and 3-probe DNA FISH, these results suggest that Evf2 RNA clouds localize with Umad1 or Akr1b8 in single nuclei, only when Dlx5/6UCE is not associated (FIG. 3H). Applicant next determined whether Evf2 alters chromosome topology between Dlx5/6UCE and target genes by comparing distances between Dlx5/6: Umad1 (X), Dlx5/6:Akr1b8 (Z), and Umad1: Akr1b8 (Y) in 83 nuclei from Evf2$^{+/+}$ and Evf2$^{TS/TS}$. Binning XYZ values by size shows that Evf2 regulates distance profiles (FIG. 3I-K). A 3D-density map of nuclei according to XYZ coordinates compares the distribution of Evf2$^{+/+}$ (red) and Evf2$^{TS/TS}$ (blue) nuclei, and indicates increased clustering by Evf2$^{+/+}$ nuclei (FIG. 3L). Self-organizing maps (SOMs) optimally cluster gene-distance data and reveal Evf2$^{+/+}$ nuclei clusters that are connected by closer distances (yellow hexagons) compared to Evf2$^{TS/TS}$ (FIG. 3M, FIG. 8C-F), visualizing distinct connections between Evf2$^{+/+}$ (orange) and Evf2$^{TS/TS}$ (blue) centroids (FIG. 3N). Taken together, these data indicate that Evf2 regulates chromosome topology in the 27 Mb region by altering Dlx5/6: Umad1: Akr1b8 gene-distance relationships in a heterogeneous manner among interneuron subpopulations.

Evf2 Regulates Both the Position and Number of Dlx5/6UCE Interactions Across Chr6

Figures 3A, 3N:
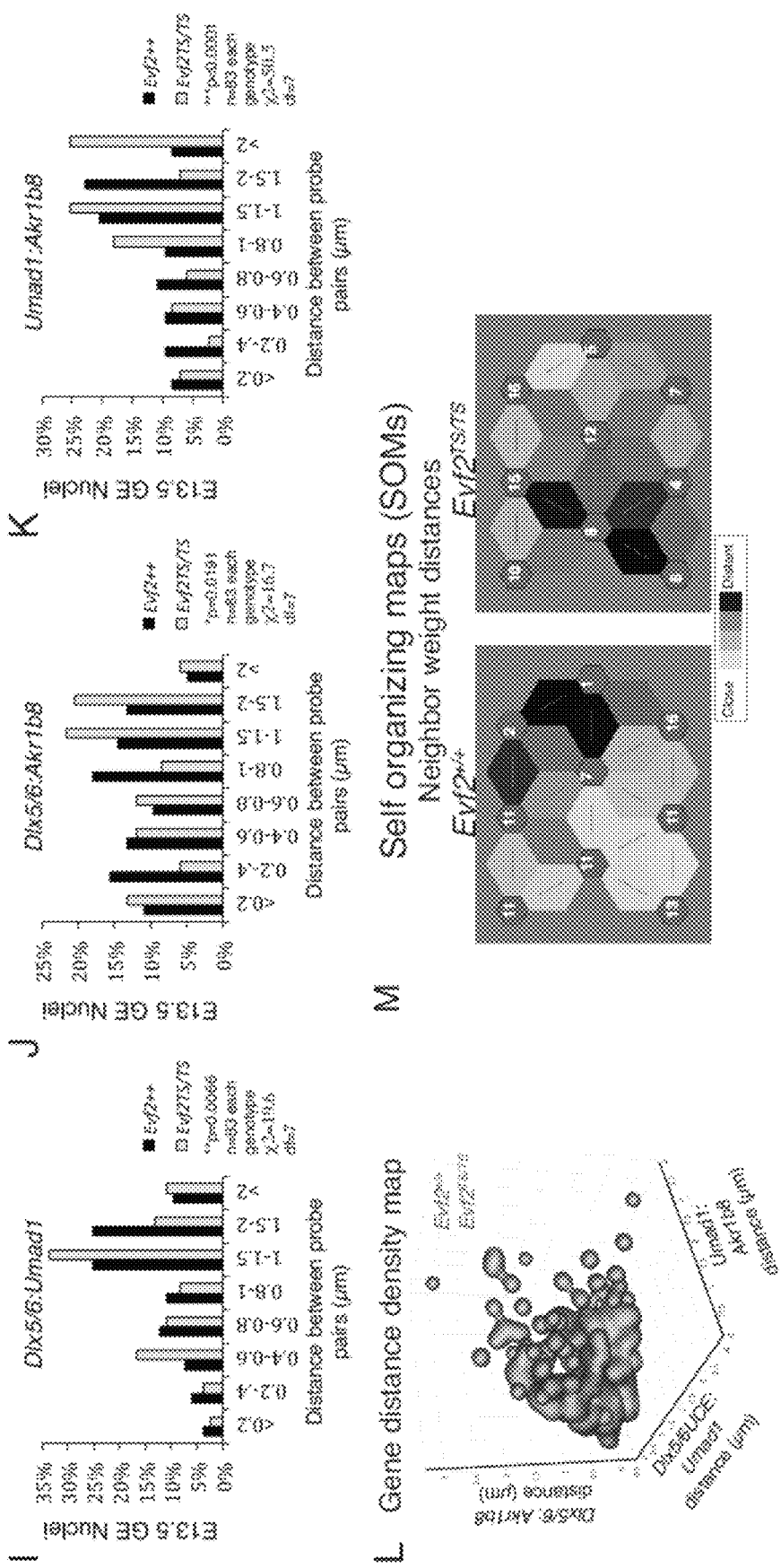
Figures 3A, 3N:
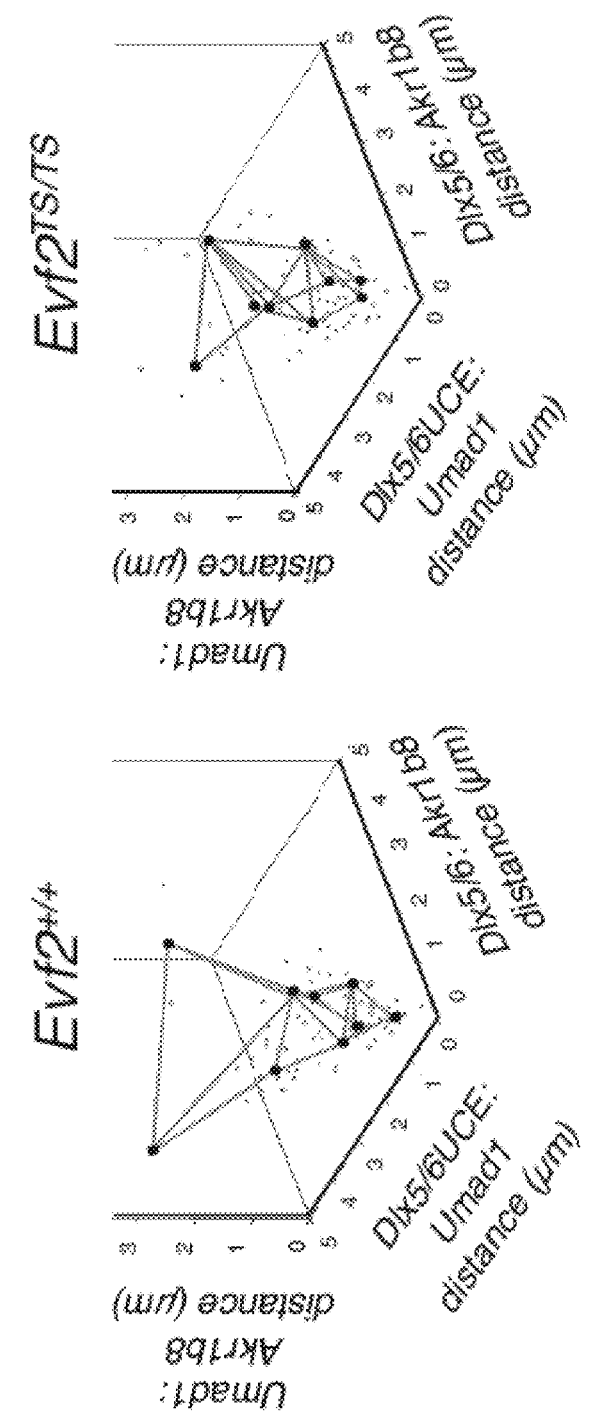
Figures 4A, 4B, 4C, 4D, 4E, 4F, 4G, 4H, 4I, 4J:
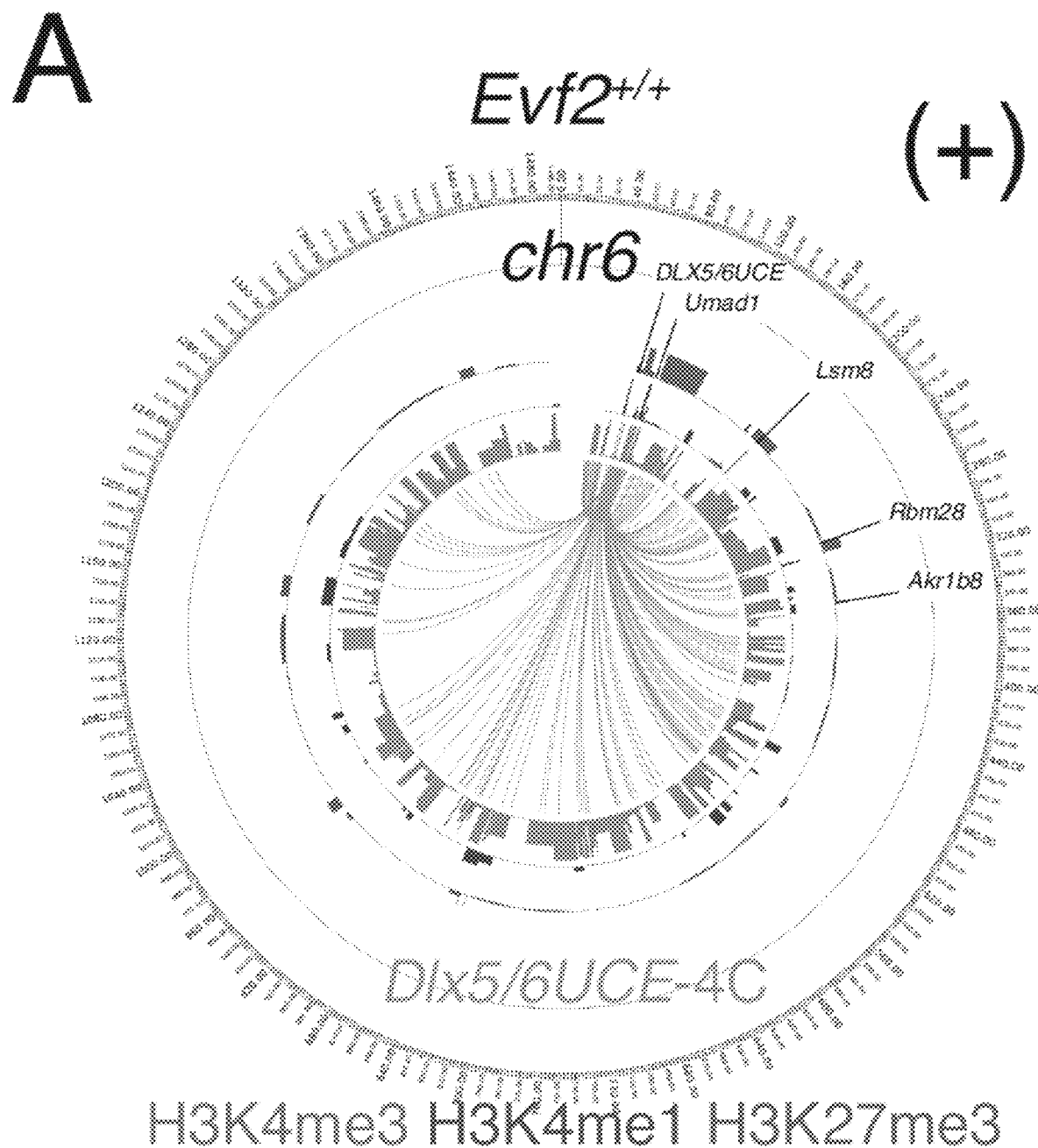
FIG. 4A-J. Evf2 regulates Dlx5/6UCE interactions across chr6. A-C. Integrated Circos plots indicating Dlx5/6UCE interaction sites across chr6 (inner panels showing interactions identified by 4C-seq of GE), and corresponding H3Kme profiles (identified by native ChIPseq of GE, H3K4me3 [green], H3K4me1 [purple], H3K27me3 [red] peaks). A. enriched in Evf2$^{+/+}$ (+, positively regulated), B. enriched in Evf2$^{TS/TS}$ (−, negatively regulated), C. conserved (detected in both Evf2$^{+/+}$ and Evf2$^{TS/TS}$I, Evf2-independent). D-E. Upper panels indicate the distribution of Evf2-regulated Dlx5/6UCE interacting sites (Evf2$^{+/+}$ (+), orange empty circles, Evf2$^{TS/TS}$ (−), empty blue circles. Lower panels indicate the density of Evf2-regulated Dlx5/6UCE interacting sites. D. Across entire chr6 (~150 Mb), E. Across 0-40 Mb of chr6 (including 27 Mb region containing the Dlx5/6UCE bait and transcriptional target genes, Umad1, Lsm8, Rbm28, and Akr1b8). F-J. Normalized read counts of histone modifications H3K4me3, H3K4me1, H3K27me3, and H3K27ac with respect to distance from Dlx5/6UCE-chr6 interacting sites. Histone modification plots showing p-value calculations at ±0-2 kb, 0±6 kb, and 0±10 kb, indicated by grey bars; pink line (p=0.05) on the right y-axis indicates the cut-off for significant differences. F. Evf2$^{+/+}$ comparison of histone modification profiles at Evf2-Dlx5/6UCE-chr6 sites (+, orange solid line) and (−, orange dashed line), (unpaired t-test). G. Evf2$^{TS/TS}$ comparison of histone modification profiles at Evf2-Dlx5/6UCE-chr6 sites (+, blue solid line) and (−, blue dashed line), (unpaired t-test). H. Comparison of histone modifications profiles at Evf2-Dlx5/6UCE-chr6 sites (+) in Evf2$^{+/+}$ (orange line), and Evf2$^{TS/TS}$ (blue line), (paired t-test). I. Comparison of histone modification profiles at Evf2-Dlx5/6UCE-chr6 sites (−) in Evf2$^{+/+}$ (orange line), and Evf2$^{TS/TS}$ (blue line), (paired t-test). J. Comparison of histone modification profiles at conserved Dlx5/6UCE-chr6 interaction sites (Evf2-independent, I) in Evf2$^{+/+}$ (orange line), and Evf2$^{TS/TS}$ (blue line), (paired t-test).
Figures 4A, 4B, 4C, 4D, 4E, 4F, 4G, 4H, 4I, 4J:
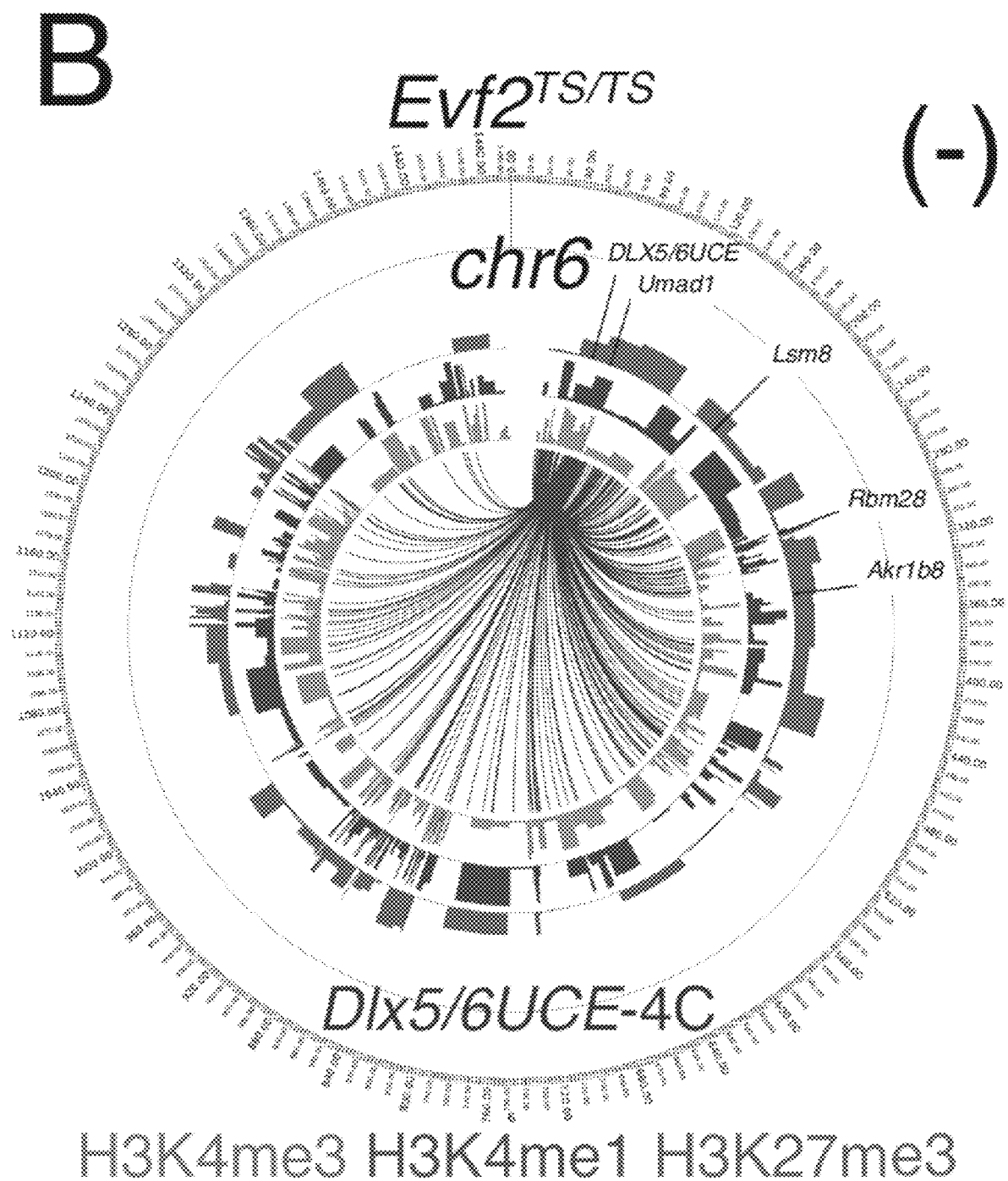
Figures 4A, 4B, 4C, 4D, 4E, 4F, 4G, 4H, 4I, 4J:
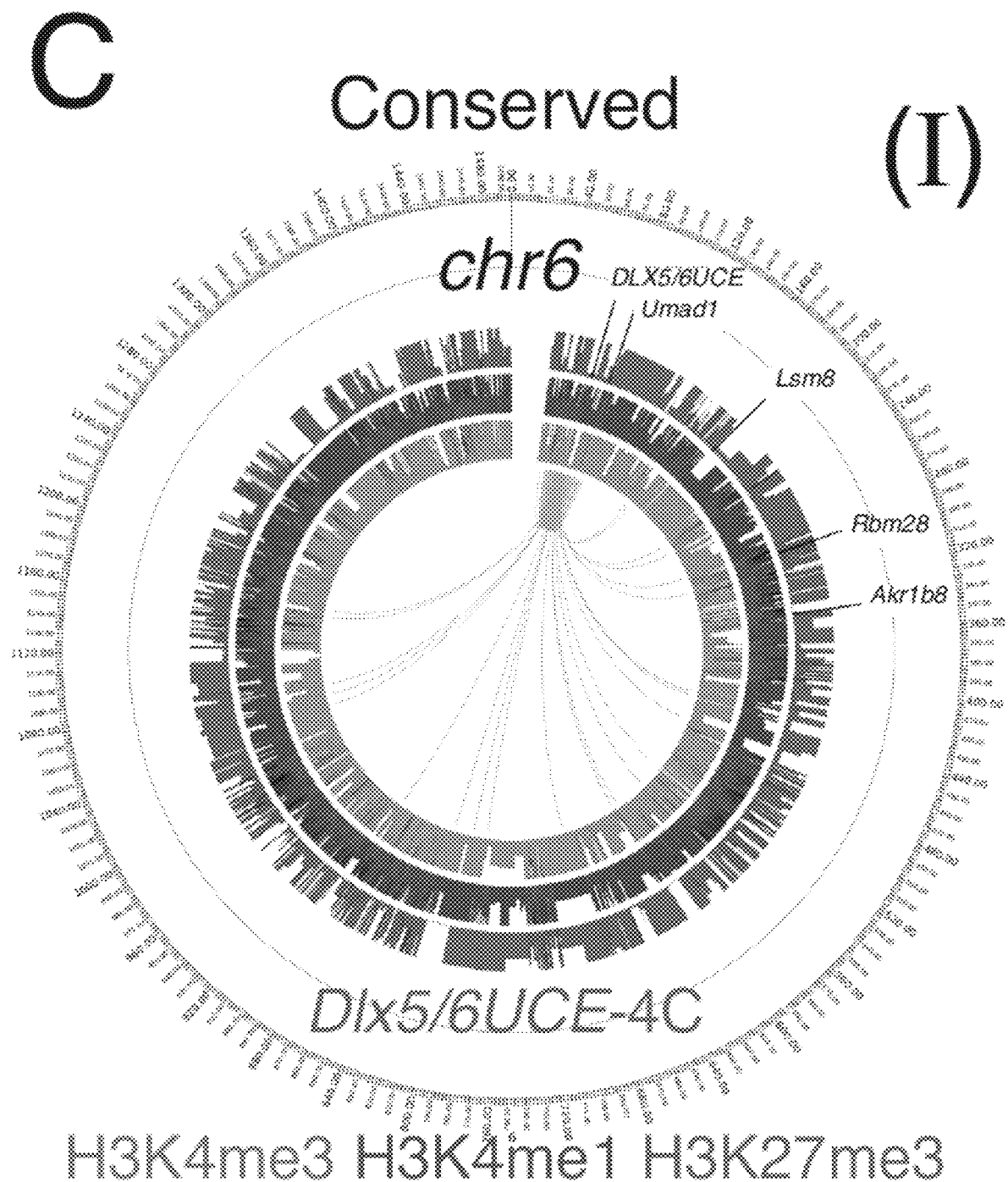
Figures 4A, 4B, 4C, 4D, 4E, 4F, 4G, 4H, 4I, 4J:
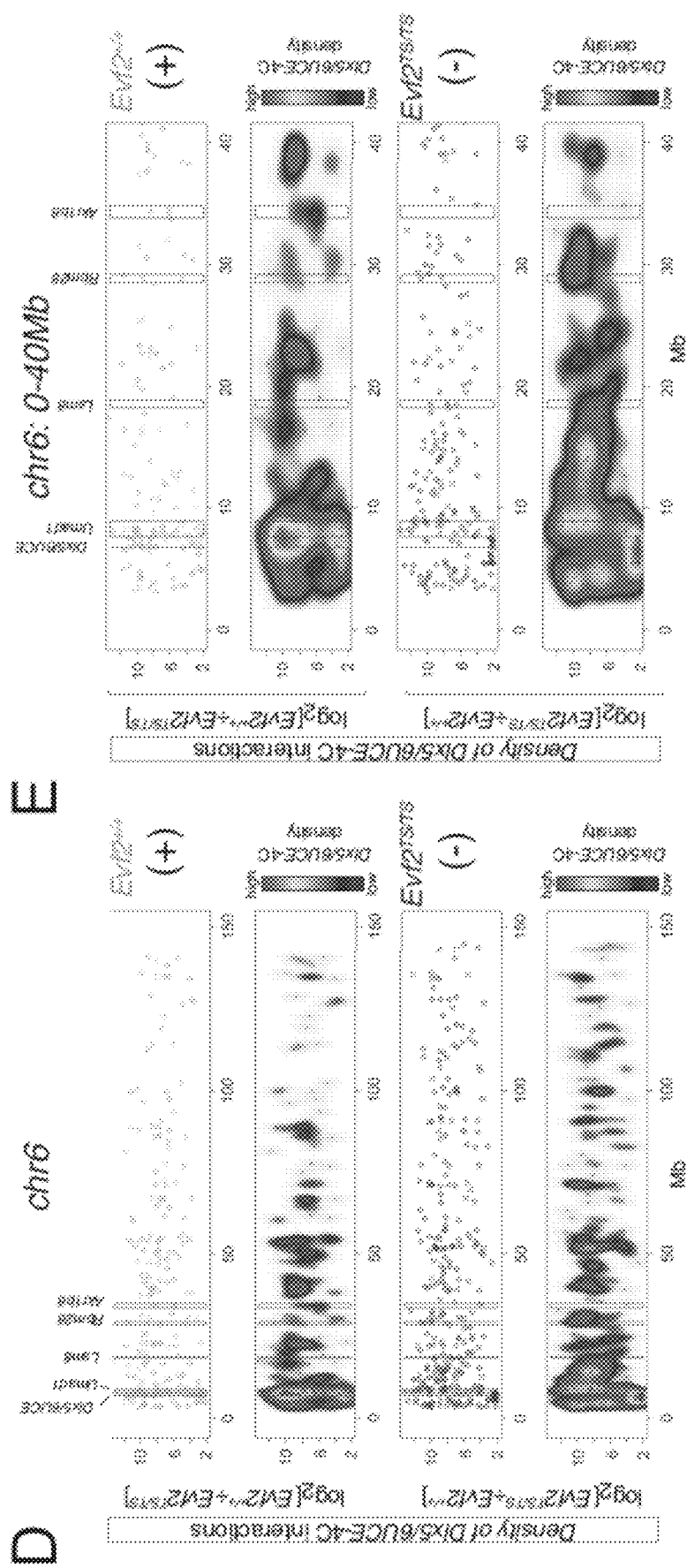
Figures 4A, 4B, 4C, 4D, 4E, 4F, 4G, 4H, 4I, 4J:
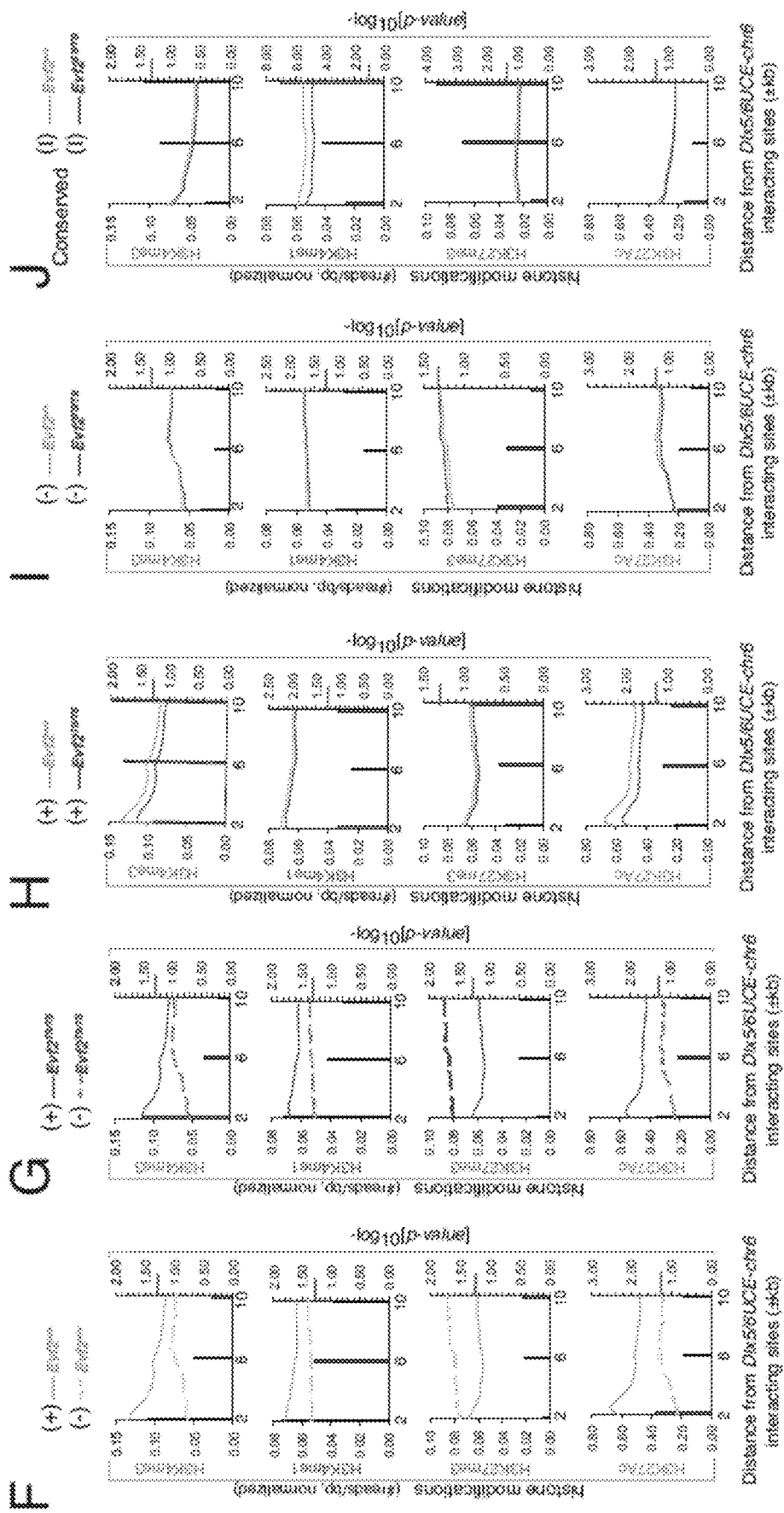

Evf2 RNA cloud co-localization with DNA loci (Umad1, and Akr1b8) and topological changes in Dlx5/6UCE: Umad1:Akr1b8 are consistent with a direct role for Evf2 RNA in transcriptional regulation (FIG. 3). However, the question of whether Evf2-dependent topological effects are restricted to transcriptionally regulated target genes, or extend to chr6-wide regulation remained. Applicant next used high-throughput Chromosome Conformation Capture sequencing (4C-seq) (van de Werken et al., 2012) with Dlx5/6UCE as the bait sequence to compare all Dlx5/6UCE interacting sites in Evf2$^{+/+}$ and Evf2$^{TS/TS}$ E13.5GE (FIG. 4A). Although 3-D visualization is not possible, advantages of 4Cseq are greater resolution (~5-10 kb) and sensitivity compared to DNA-FISH, allowing quantification of Dlx5/6UCE-gene interactions that occur in minor cell subpopulations.

Circos plots of Dlx5/6UCE interacting sites across chr6 show hundreds of interactions, the majority of which are Evf2-regulated (FIG. 4A). Positively-regulated sites, detected in Evf2$^{+/+}$ and not in Evf2$^{TS/TS}$ are represented by orange lines (+), whereas negatively-regulated sites, detected in Evf2$^{TS/TS}$ and not in Evf2$^{+/+}$ are represented by blue lines (−). Conserved sites, detected in both Evf2$^{+/+}$ and Evf2$^{TS/TS}$ are represented by grey lines, and indicate fewer Evf2-independent interactions at a distance from the bait (I). Circos plots of the 0-40 Mb region indicate the relative positions of Evf2-chr6 targets, with fewer (I) interaction sites at a distance (>±2.5 Mb) from the bait, compared to (+)/(−) interactions (FIG. 9). While Circos plots highlight changes in the position of Dlx5/6UCE interaction sites, 2-D density plots display both the intensity of the change and the density of interaction sites (blue-red gradient indicating density of interactions), with superimposed black dots indicating site positions (restriction enzyme sites, FIG. 4B). Panels indicating the position of interaction sites (hollow orange/blue circles) and relationship to Evf2-chr6 targets are also included on top of each density plot. While the highest density of both (+) and (−) interactions occurs close to the bait (red and yellow regions), higher fold changes are more dramatic for (+) (y-axis). In addition, density analysis indicates that the region between 60-100 Mb (x-axis) contains more (+) sites, whereas >100 Mb region contains more (−) regulated sites. Analysis of (+) interactions with Evf2-chr6 targets reveals high-density (red/yellow) interaction fold changes with Umad1, mid-density interactions (green) with Akr1b8 (FIG. 4B), and (+) and (−) low density interactions (blue) with Lsm8 and Rbm28. Together with DNA-FISH, these data support that Evf2 regulates the number and position of Dlx5/6UCE interactions to repressed and activated target genes, as well as across the full-extent of chr6.

Figures 9A, 9B, 9C, 9D, 9E, 9F, 9G:
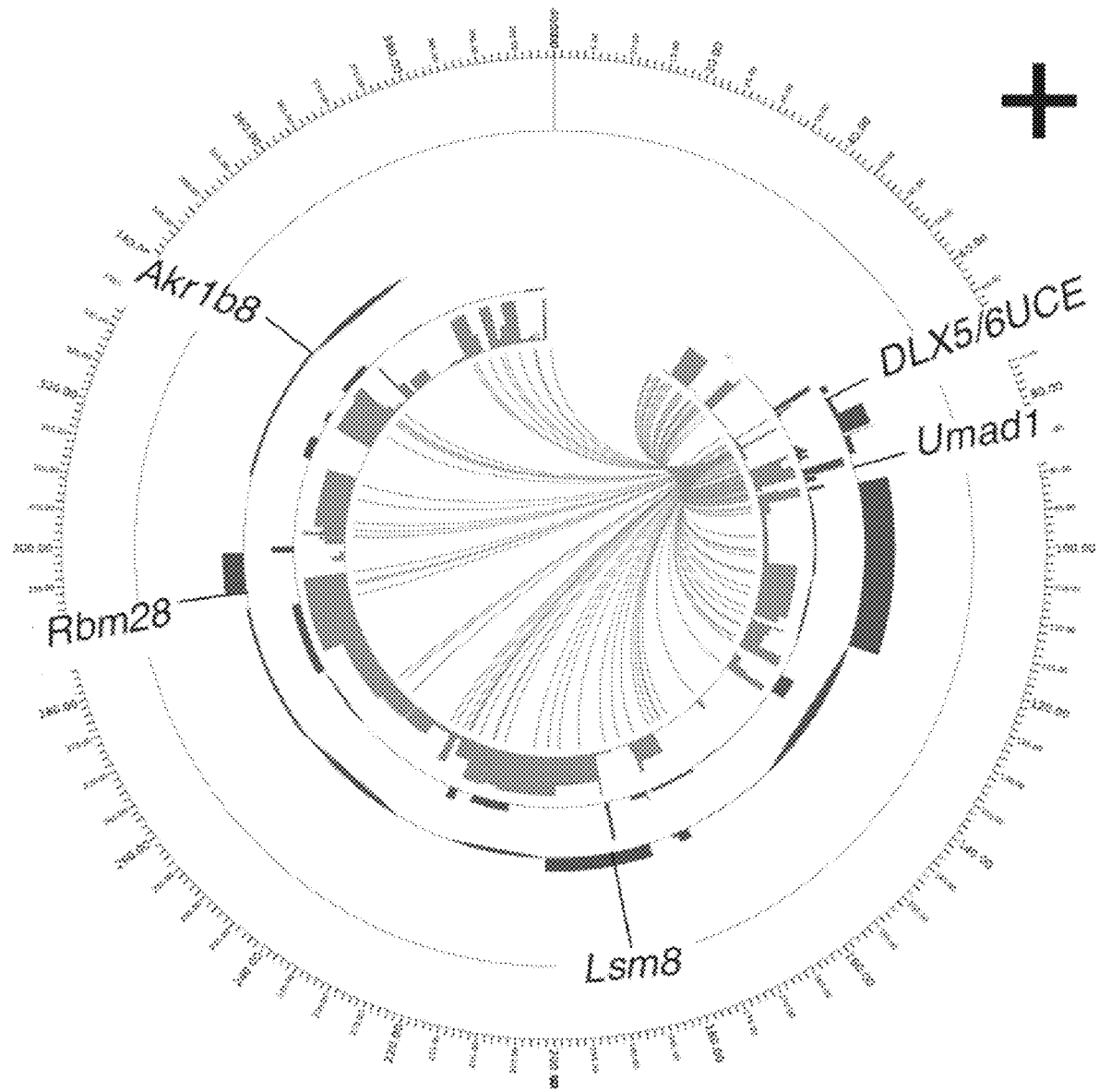
FIG. 9A-G. Evf2-dependent and independent Dlx5/6UCE interactions and histone lysine methylation effects across chr6 (0-40 Mb) and at Evf2-chr6 target genes. A-C. Integrated Circos plots indicating Dlx5/6UCE interaction sites across chr6 (0-40 Mb), with the Dlx5/6UCE bait and long-range transcriptionally regulated target genes (Umad1, Lsm8, Rbm28, Akr1b8) labeled. Inner panels show Dlx5/6UCE interactions identified by 4Cseq; surrounding panels align histone lysine methylation profiles (MACS2 enriched (+/−) or conserved (I) identified by native ChIPseq of E13.5GE, H3K4me3 [green], H3K4me1 [purple], H3K27me3 [red]. A. enriched in Evf2+/+(+, positively regulated), B. enriched in Evf2TS/TS (−, negatively regulated), C. conserved (detected in both Evf2+/+ and Evf2TS/TS, I, Evf2-independent). D-G. Zoomed in regions of Dlx5/6UCE interacting sites (+, red region) and (−, yellow region) aligned with differential histone lysine methylation effects at Evf2-chr6 target genes. D. Umad1, E. Lsm8, F. Rbm28, G. Akr1b8. Only differential ChIPseq peaks are indicated. Taken from Wust1 genome browser site. Evf2-dependent changes in histone lysine methylation at (+) and (−) do not follow general correlations with respect to transcriptional regulation.
Figures 9A, 9B, 9C, 9D, 9E, 9F, 9G:
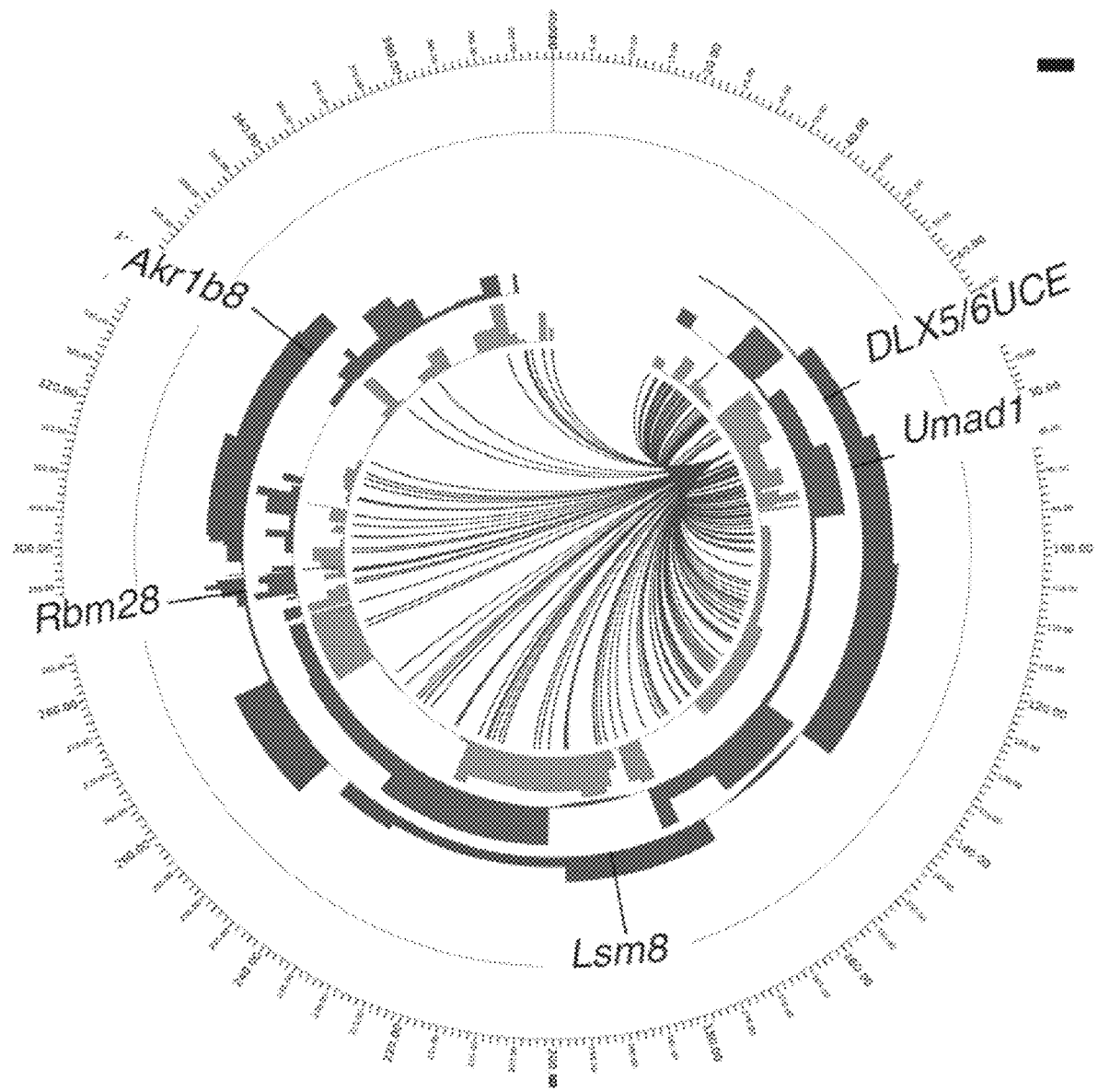
Figures 9A, 9B, 9C, 9D, 9E, 9F, 9G:
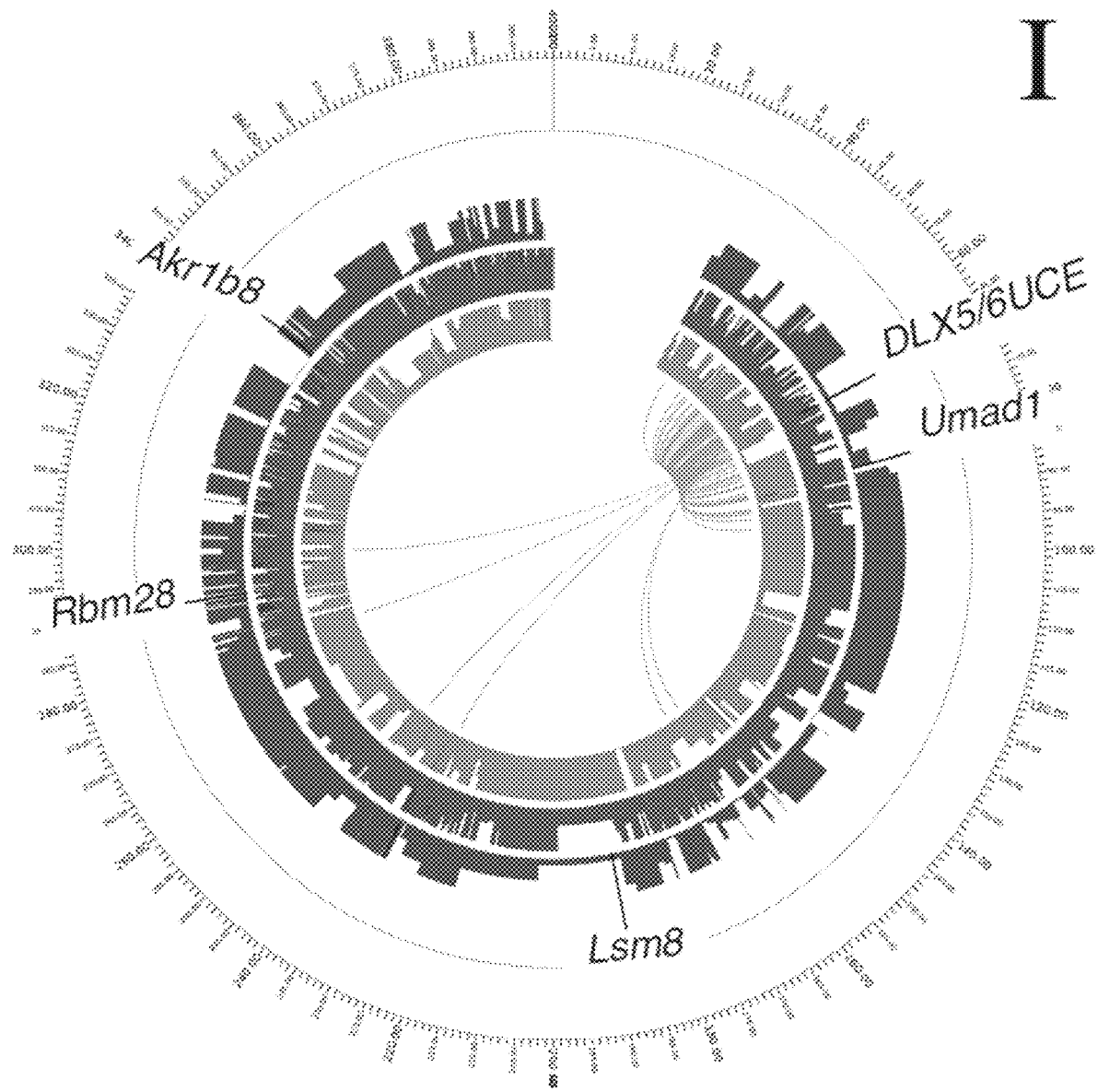
Figures 9A, 9B, 9C, 9D, 9E, 9F, 9G:
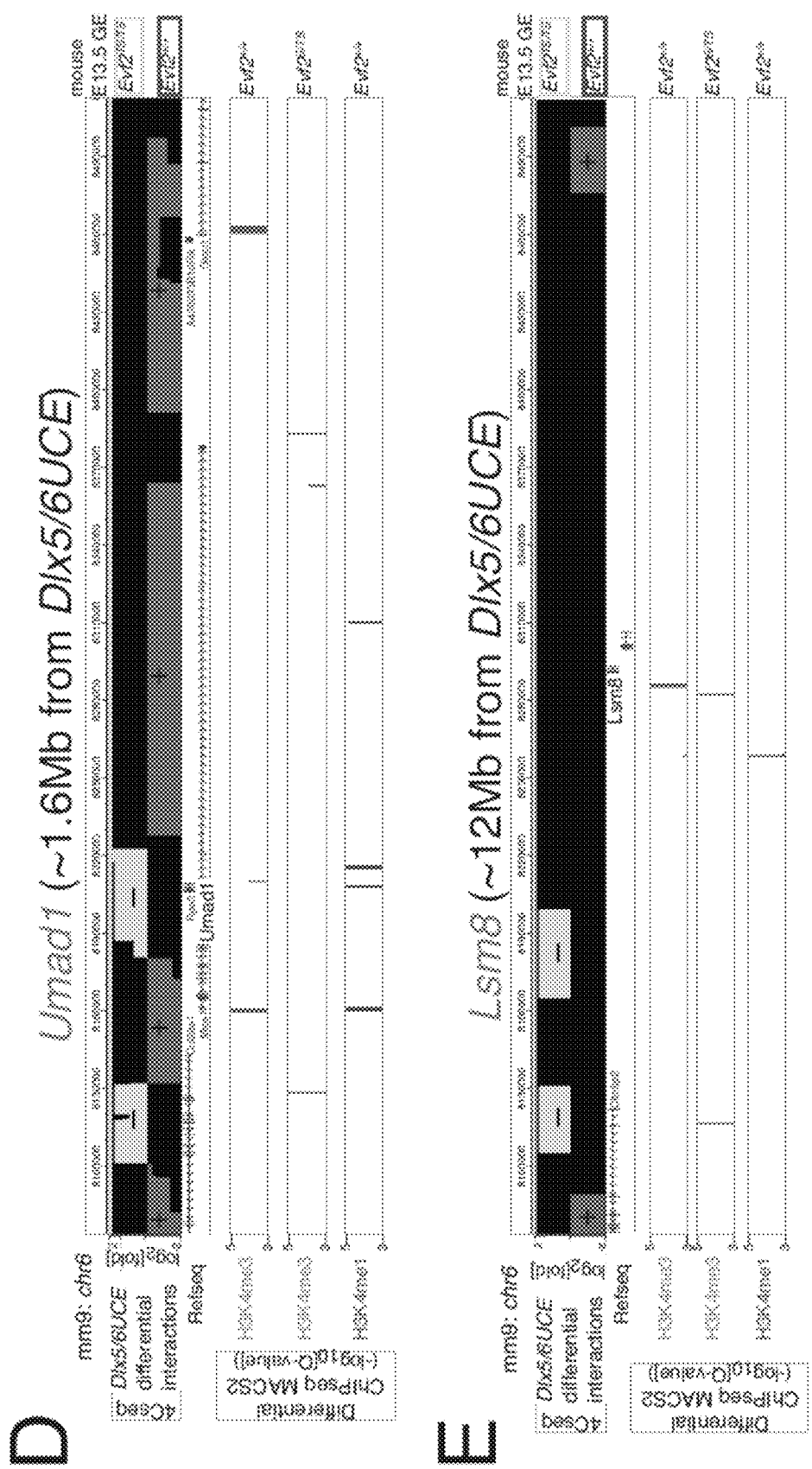
Figure 13:
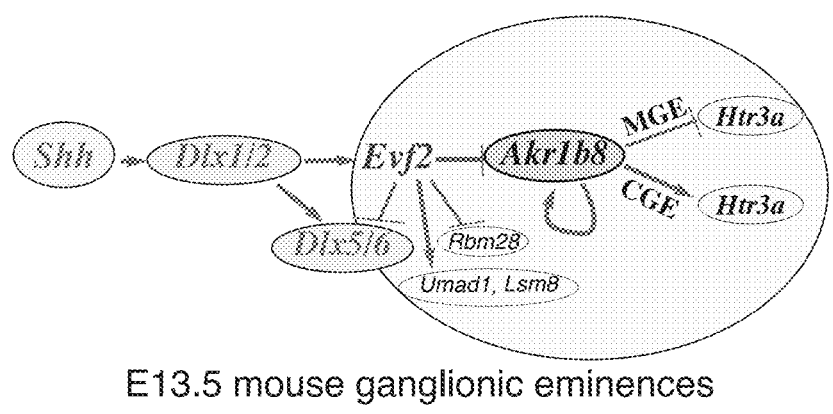

Active Histone Modifications Distinguish Between Evf2 Positively and Negatively Regulated Dlx5/6UCE-Chr6 Interaction Sites In order to further characterize Dlx5/6UCE-chr6 interactions, Applicant compared histone lysine modification profiles in Evf2$^{+/+}$ and Evf2$^{TS/TS}$ chromatin, using ChIP-seq. Circos plots align profiles of differentially regulated histone lysine methylation (H3K4me1/3, H3K27me3) peaks with Dlx5/6UCE interactions (chr6-wide: FIG. 4A-C, 27 Mb: FIG. 9A-C). Examination of H3Kme at Evf2-chr6 long-range target genes (Umad1, Lsm8, Rbm28, and Akr1b8) reveals that differences between (+) (red region), (−) (yellow region) in Evf2$^{+/+}$ and Evf2$^{TS/TS}$ are gene specific (FIG. 9D-G). However, chr6-wide analysis indicates that active marks (H3K4me3/1 and H3K27ac), but not inactive H3K27me3 marks, are enriched at (+) sites compared to (−) sites (FIG. 4F). Surprisingly, enrichment of active marks at (+) sites occurs in both Evf2$^{+/+}$ and Evf2$^{TS/TS}$ (FIGS. F, G), supporting that active marks precede Evf2-regulated Dlx5/6UCE interactions. Direct comparisons of H3K4me3 and H3K27ac profiles in Evf2$^{+/+}$ and Evf2$^{TS/TS}$ indicate very few changes (see subtle line shifts, FIG. 4H), supporting Evf2 independence at the majority of (+) sites. Furthermore, although Evf2 does not regulate the overall histone modification differences between (+), (−) and (I) sites, these differences support the involvement of differential mechanisms in (+), (−) and (I) site selection (FIG. 4I, J). Thus, in permissive regions, active histone modifications selectively mark the majority of (+) sites, prior to Evf2 regulation, while in the instructive 27 Mb region containing Dlx5/6UCE-Evf2-chr6 target genes, Evf2 regulates active and repressed histone methylation of (+) and (−) sites in a gene-specific manner.

Discussion

In this work, Applicant shows that Evf2-chr6 targets are asymmetrically positioned across-27 Mb, 5' to the Evf2 transcription start site, with the closest (Dlx6) and furthest genes (Akr1b8) regulating interneuron subtype genes (FIG. 5A). Analysis of multiple genetic models supports in vivo dosage relationships between Dlx6-Calb1, Umad1-Sst, Umad1-5Htr3a, and Lsm8-Npy (FIG. 6B). Together with published reports that Dlx5/6 dosage controls the development of parvalbumin interneurons (Cho et al., 2015; Wang et al., 2010), Applicant's genetic experiments link five of six Evf2-chr6 target genes to interneuron diversity. Thus, Evf2 regulates a small group of megabase distant genes with biochemical and genetic roles in interneuron diversity, functionally organizing a 27 Mb region of chr6.

While involvement of Evf2-Dlx6 in regulating interneuron subtype genes may not be surprising, identification of Dlx6-regulated enhancers at multiple interneuron subtype genes (Calb1, Npy, and Sst) is unexpected, and supports a major role for Dlx6 dosage. In addition, the Evf2-Akr1b8-5Htr3a axis links the mevalonate pathway to Akr1b8 regionally controlled enhancer activity, revealing a novel role for lncRNA regulation of lipid metabolism in interneuron diversity. This is important, as the embryonic 5Htr3a+ interneuron population gives rise to a major subclass of adult interneurons (vasoactive intestinal peptide, VIP+) involved in disinhibition, and control of adult brain circuitry and behavior (Lee et al., 2013; Letzkus et al., 2011; Pi et al., 2013). In addition, 5Htr3a itself controls the migration of interneuron progenitors from CGE to adult destinations (Murthy et al., 2014). Thus, developmental effects on Gad1 expression combined with changes in multiple interneuron subtype genes may contribute to adult brain GABAergic circuitry defects in mice lacking Evf2 (Bond et al., 2009).

Regulation of Dlx5/6UCE-Gene Interactions Across Mouse Chr6: Biological Significance and Human-Mouse Conservation In subpopulations of interneurons, Evf2 localizes to both activated and repressed target genes, regulating Dlx5/6UCE-target gene distances, and supporting a role in spatial organization of genes across ~27 Mb. In addition to human chr7 synteny within the 27 Mb region of mouse chr6, evidence that Evf2 is enriched 6000-fold in human embryonic brain interneurons compared to other lncRNAs, supports Evf2 significance in human brain development (Liu et al., 2016). Across chr6 (~150 Mb), Evf2 regulates the number, density, and position of Dlx5/6UCE-chr6 interactions (FIG. 4A-E, 5B-C), indicating that topological effects extend beyond the transcriptionally targeted 27 Mb region (instructive region). However, is there evidence to support that Dlx5/6UCE-chr6– wide interactions outside the 27 Mb region (permissive region) are biologically significant, despite the absence of transcriptional effects? Gene ontology analysis (GO) of Dlx5/6UCE-chr6-wide gene interactions shows that specific biological processes are associated with (−) (development, transcription, metabolic/biosynthetic process) and (I) (stimulus response) (FIGS. 5B-D), and that Evf2 regulates the majority of Dlx5/6UCE-chr6 interactions, with only 4.3% independent of Evf2 (FIG. 5D, compare grey circle). Analysis of human developing brain Dlx5/6UCE-chr7 gene interactions (Won et al., 2016) indicates that ~65% of mouse E13.5GE Dlx5/6UCE-chr6 gene interactions (Evf2$^{+/+}$, orange, FIG. 5E) are conserved. Conversely, ~44% of human Dlx5/6UCE-chr7 gene interactions are conserved with mouse Dlx5/6UCE-chr6 gene interactions (FIG. 5E). Furthermore, ~51% of human Dlx5/6UCE-chr7 gene interactions are subject to Evf2− regulation in mice (FIG. 5E, deep yellow, red and green overlap). Thus, human-mouse conserved Dlx5/6UCE-chr6 gene interactions and GO analysis support the potential biological significance of UCE-lncRNA topological control across chr6, even at genes that do not have detectable changes in gene expression.

Selective Regulation of Megabase Distant Genes Through Complex Effects on Chromosome Topology Although the majority of Evf2-regulated Dlx5/6UCE-chr6 sites do not cause detectable changes in gene expression, it is possible that cellular heterogeneity masks transcriptional changes. RNA/DNA and DNA/DNA FISH analysis supports heterogeneity in chromosome topology among interneuron progenitors. In addition, E13.5GE interneuron progenitors can be divided into three categories of Evf2 RNA cloud expression (zero, one, or two/nucleus) (FIG. 3B-C), contributing to heterogeneity. Although Evf2 regulation of Umad1 (~6-fold increase) and Akr1b8 (~7-fold decrease) is dramatic, Dlx5/6:Umad1 and Dlx5/6:Akr1b8 co-localization occurs in <10% of nuclei (FIG. 3I, J). Recent evidence supports highly heterogeneous chromosome 3D structures in single cells (Stevens et al., 2017, Nagano et al., 2017). It remains to be determined whether heterogeneity results from transient, unsynchronized interactions that occur in the majority of cells, or interactions that are limited to specific GE subpopulations. In support of dynamic or transient mechanisms is the surprising result that the Evf2 RNA cloud does not co-localize at Dlx5/6UCE, despite co-localization with target genes Umad1 and Akr1b8 (FIG. 3B, C, H). Given that only one-two Evf2 RNA clouds are detected per nucleus, it is likely that the Evf2 RNA cloud forms away from the site of Evf2 transcription initiation, and moves along chr6 to regulate target genes.

In addition to cellular heterogeneity, another possible explanation is that topological changes precede gene expression changes, and are part of a dynamic procession during development. Evidence that chromosome topology is dynamic and changes during developmental and or cell cycle transitions has been reported (Hug et al., 2017; Nagano et al., 2017; Noordermeer et al., 2011; Phillips-Cremins et al., 2013). Therefore, Evf2 may be permissive and establish a topology required for future regulatory events, similar to that proposed for ZRS-Shh interactions in the zone of polarizing activity in the limb (Williamson et al., 2016). Furthermore, the finding that (I) gene interactions are grouped with stimulus response genes (GO analysis, FIG. 5D) raises the possibility that transcriptional changes may be revealed in response to specific stimuli. Thus, it will be important to determine how heterogeneity, transient vs. stable associations, stimulus response, and developmental timing mechanisms relate transcriptional control and Evf2− regulated Dlx5/6UCE-chr6 gene interactions.

Data in this application support the idea that Evf2-Dlx5/6UCE interactions spatially and functionally organize megabase distant genes involved in interneuron diversity across a 27 Mb region of chr6. The requirement of the UCE-containing region (Evf2-5′) in regulating neuronal diversity through repression of Dlx6 and Akr1b8, supports a role for ultraconserved sequences that function through both RNA and DNA mechanisms. However, Evf2 gene activation requires the Evf2-3′ end, and in the case of Lsm8, occurs through a trans-mechanism (FIG. 1H, 5A), supporting functional constraints outside of the ultraconserved sequence. Thus, Evf2-5′ and -3′ distinguish between long-range repression (Akr1b8, Rbm28) and activation (Umad1, Lsm8) within the 27 Mb region. FIGS. 4E and 9D-G show that (+) and (−) sites are identified at both activated and repressed target genes (Umad1, Lsm8, Rbm28). Thus, Evf2 regulated Dlx5/6UCE interactions within the 27 Mb region do not follow a general rule where (+)/(−) sites correlate with transcriptional activation/repression. Furthermore, although Evf2 regulates Dlx5/6UCE: Umad1:Akr1b8 topology, such effects appear heterogeneous, and also do not follow simple correlations between gene-distances and transcriptional effects (FIG. 3I-K). Evf2 control of specific Dlx5/6UCE gene distance relationships are best revealed using SOMs, showing that Evf2 increases the number of nuclei that are in clusters connected by closer distances (FIG. 3O-P). Together, these results support that Evf2 and Dlx5/6UCE selectively regulate megabase distant genes through complex spatial effects on chromosome topology, with distinct roles of the Evf2-5′ and -3′ regions in transcriptional activation and repression.

Conservation of Dlx5/6UCE-chr6/7 gene interactions in mice and humans, and association of (−) and (I) with specific biological processes, support that interactions are part of a selective rather than stochastic process (FIG. 5A, D). Surprisingly, chr6-wide increase of active histone modifications at (+) compared to (−) sites is Evf2-independent (FIG. 4F-I, FIG. 5B), supporting that H3K4me3/1 and H3K27ac marks precede lncRNA-dependent enhancer interactions in permissive regions. Future experiments to define the mechanism of Evf2-Dlx5/6UCE-chr6 site selection specifically through studies of individual components of the Evf2-RNP complex (Cajigas et al., 2015) will be important to understanding how instructive and permissive topological domains are established.

Materials and Methods

Mouse Strains

Generation of Evf1$^{TS/TS}$ Mice

The Evf1 targeting construct was generated using lambda phage based recombineering in *E. coli* as described (Liu et al. 2003). The retrieval vector was constructed as follows. Using high fidelity Taq (Roche), homology arms of approximately 500 bp were PCR amplified (with restriction sites added) from BAC DNA. Using a three-fragment ligation, homology arms were cloned into ClaI and NheI sites of PL253, with a HindIII site engineered between them. A 19.4 kb region (corresponding to position 6,809,651-6825,742 on mouse chromosome 6, NCBI assembly) was retrieved from pBAC e3.6 M8 (M. Ekker, U. Ottawa) into the retrieval plasmid using recombination-induced EL250 cells (Liu et al. 2003). Further targeting was performed on the retrieved plasmid. The polyadenylation targeting vector was constructed in PL452, a floxed-Neo containing plasmid. The triple polyadenylation signal (Soriano 1999) was cloned into EcoRI and SalI sites of PL452. Approximately 500 bp of targeting homology arms were cloned sequentially on either side of the polyA-floxed-Neo insert. Briefly, fragments were PCR amplified as above and cloned into either ClaI and KpnI sites or NotI and SacII sites. This triple polyA-floxed-Neo cassette was targeted into the retrieved 19.4 kb region using recombination-induced EL250 cells. Successful targeting was confirmed by Southern blot analysis of the completed construct using internal probes (NEBlot kit, NEB).

Mouse ES cells were targeted by homologous recombination using standard procedures. Successful targeting in ES cells was confirmed by Southern blot, verifying proper recombination at both the 5' and 3 ends. Probes were generated outside the 19.4 kb homologous region. EL250 cells and recombineering plasmids PL253 and PL452 were provided by Dr. Neal Copeland.

Evf1TS (floxed neo)/+ heterozygotes were verified by Southern, crossed to EIIAcre (Jackson Labs) for two generations, and crossed to the Evf2$^{TS/TS}$ background. Neo removal was verified by PCR (not shown). Mice are maintained on the same mixed background as Evf2$^{TS/TS}$ strain; all mice are housed according to IACUC guidelines.

Additional Mouse Strains

1. Evf2$^{TS/TS}$ (Bond et al. 2009) were crossed to C57/Bl6 for one generation, and maintained on a mixed background (C57/Bl6, 129Sv, FVB), source: Kohtz lab
2. Evf2$^{TS/TS:R}$ (Berghoff et al. 2013), maintained on the same background as Evf2$^{TS/TS}$, source: Kohtz lab
3. Akr1b8$^{+/-}$ (Akr1b8$^{tm1.1(KOMP)Vlcg}$)source: Jackson (strain 024334).
4. Akr1b8$^{-/-}$:Evf2$^{TS/TS}$: crossed to Evf2$^{TS/TS}$ for three generations, and maintained on the Evf2$^{TS/TS}$ mixed background, source: Kohtz lab
5. Dlx5/6KO/TS: Dlx5/6KO/+ mice (Merlo et al. 2002) were maintained on Evf2$^{TS/+}$ background, and crossed to Evf2$^{TS/TS}$ mixed background, source of Dlx5/6KO/+ (A. Bendall)

Microarray Data and Validation

Figures 7A, 7B, 7C, 7D, 7E:
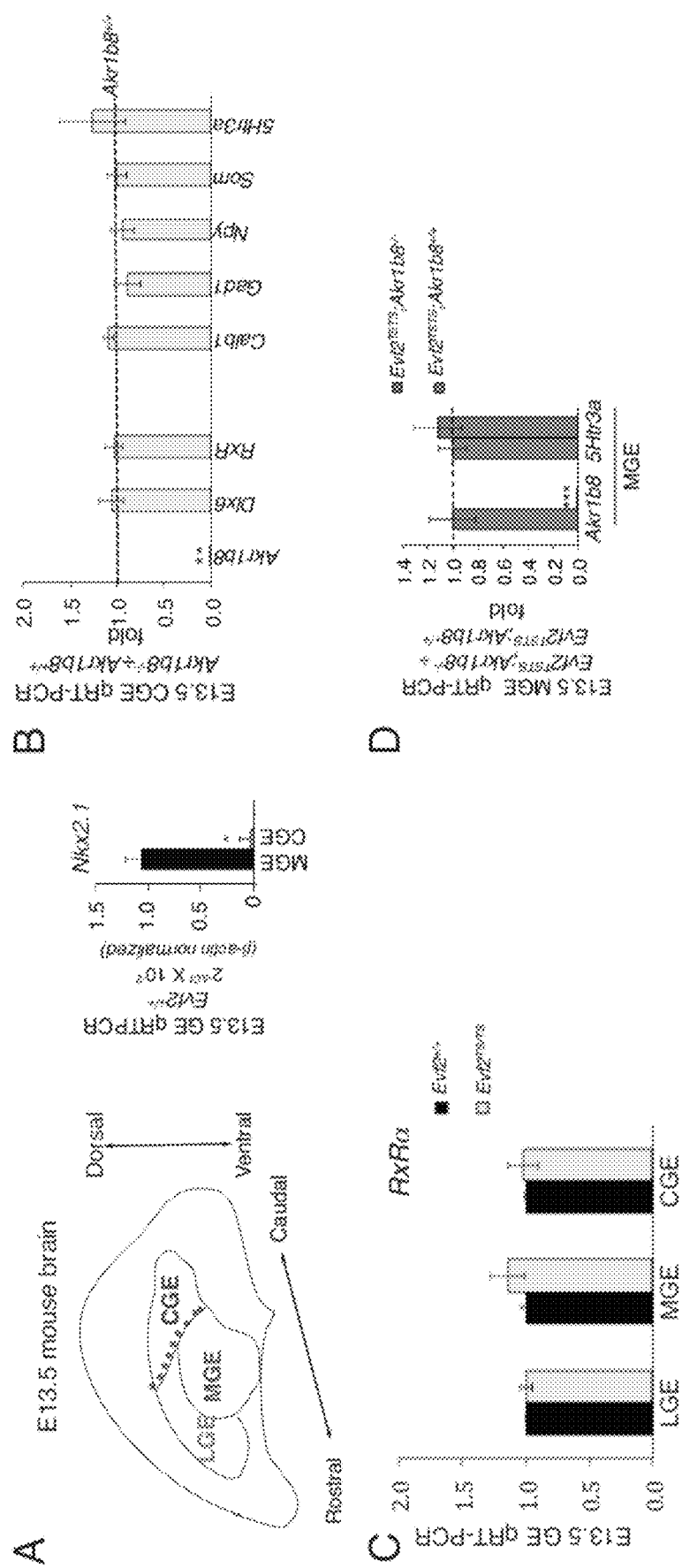
FIG. 7A-E. Genetic and epigenetic analysis of the Evf2-Akr1b8-5Htr3a axis. A. Schematic of E13.5GE mouse embryonic brain indicating sub-divisions of embryonic ganglionic eminences (LGE, MGE, CGE), with the red dotted line showing the region dissected to separate MGE from CGE. Taqman qRT-PCR analysis of Nkx2.1 (a marker for MGE), confirming accuracy of dissections between MGE (Nkx2.1 detected), and CGE (Nkx2.1 not detected), n=2 pools each region, *p=0.02. B. Taqman qRT-PCR analysis of E13.5 CGE, Evf2TS/TS normalized to Evf2+/+, Akr1b8, Dlx6, retinoid receptor alpha (RxRα), interneuron subtype genes in E13.5 CGE, Akr1b8−/− normalized to Akr1b8+/+. Loss of Akr1b8 does not affect interneuron subtype gene expression in CGE. C. Taqman qRT-PCR analysis of RxRα in LGE, MGE, and CGE of Evf2+/+ and Evf2TS/TS indicates no effects of Evf2 loss in any region of the GE. p>0.05, n=4. D. Taqman qRT-PCR analysis of E13.5 MGE Evf2TS/TS; Akr1b8−/− normalized to Evf2TS/TS; Akr1b8+/+. Akr1b8 loss does not rescue Evf2 effects on 5Htr3a in MGE (Akr1b8, 5Htr3a). n=6-15 of each genotype. Student's t-test, **p<0.01, error bars (S.E.M). E. Evf2-regulated histone lysine methylation (H3K4me3, H3K4me1, H3K27me3) changes in the Zbtb16-5Htr3a region. UCSC browser profiles of native differential ChIPseq results compare profiles in Evf2+/+ and Evf2TS/TS E13.5 GE chromatin. IDR-MACS2 peaks are indicated by black tracks, where darker bars indicate higher peak densities (black>grey). MACS2 identifies differential peaks (pink tracks), expressed in −log 10 (p-value). Computationally predicted enhancer sites are indicated at the top (Enhancers mm9, FANTOM, UCSC).
Figures 7A, 7B, 7C, 7D, 7E:
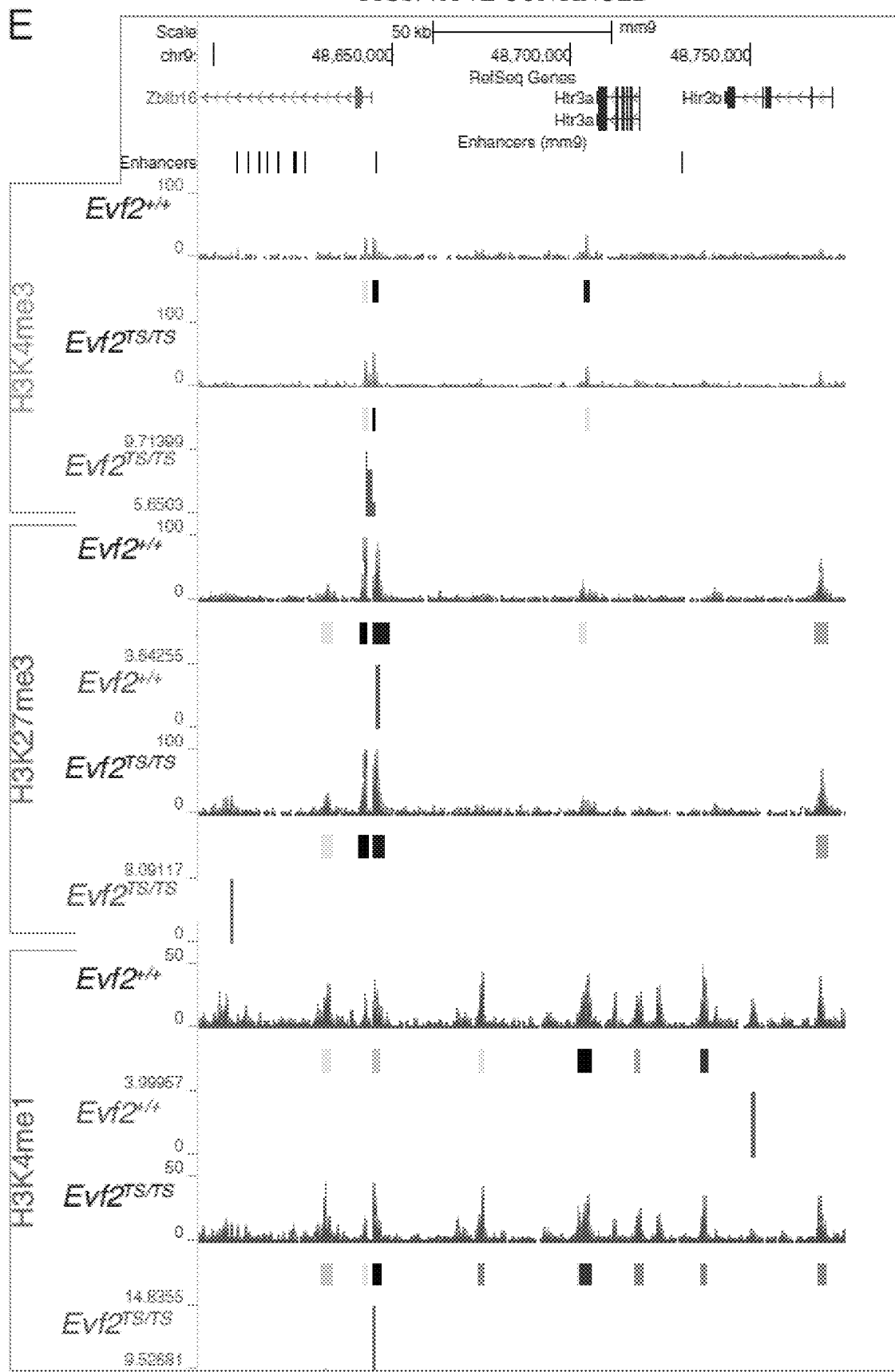
Figures 8A, 8B, 8C, 8D:
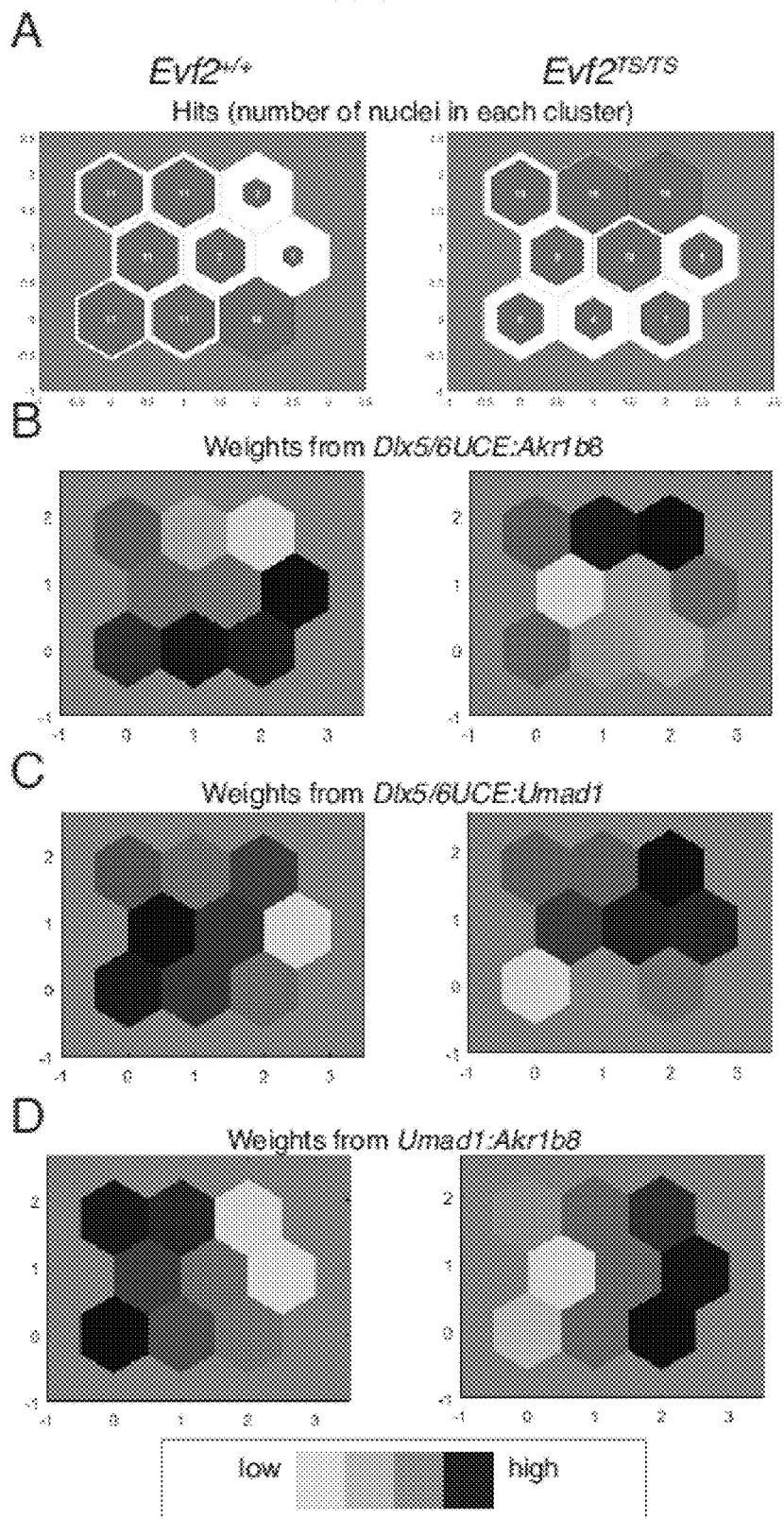
FIG. 8A-D. Self-organizing map analysis of Dlx5/6UCE-Umad1-Akr1b8 gene distances in Evf2$^{+/+}$ vs Evf2$^{TS/TS}$ E13.5GE nuclei. Dlx5/6UCE-gene distances, and gene-gene distances were calculated for 83 nuclei from Evf2+/+ and Evf2TS/TS by DNA FISH: Dlx5/6:Umad1, Umad1:Akr1b8, and Dlx5/6:Akr1b8. Self-organizing maps (SOMs) were generated in the Matlab neural net-work toolbox (NNT) using three training iterations to optimally cluster gene-distance data and visualization: (www.mathworks.com/help/nnet/gs/clus-ter-data-with-a-self-organizing-map.html). The NNT provides algorithms and applications to create and visualize neural networks, including methods for clustering data www.math-works.com/help/nnet/index.html. A. Blue hexagons represent clusters, with the number of nuclei indicated in each cluster. B-D. Weights from each distance are indicated by color, with lowest (yellow) highest (black). B. Distances between Dlx5/6UCE:Umad1. C. Distances between Dlx5/6UCE:Akr1b8. D. Distances between Umad1:Akr1b8.

E13.5 medial and caudal ganglionic eminences were isolated from embryos using fine microdissection scissors (Lumsden bioscissors), in L15 medium. In FIG. 7A, a schematic of E13.5 mouse brain shows ganglionic eminences (LGE, MGE, CGE, based on schematic (Gelman and Marin 2010)), and dorsal/ventral and rostral/caudal axes. Dotted red line shows the boundary between MGE/LGE and CGE where tissues are dissected. At E13.5, the sulcus between MGE and LGE is well defined, allowing precise definition of LGE/MGE/CGE regions under a dissecting microscope. RNA isolation, cDNA production, qPCR were performed, as previously described (Berghoff et al. 2013). For microarray analysis, 5 pools of E13.5 MGE's from two brains/genotype from males (5) and females (5) were hybridized to 10 Affymetrix. GeneChiP.Mouse430_2 arrays, and the results analyzed using GeneSpring software. Genes showing a minimum of 2-fold differences, and p-values of ≤0.05 were validated further by TaqMan qRT-PCR. Probes for TaqMan qPCR:

Dlx5 (Mm00438430_m1)
Dlx6 (Mm01166201_m1)
Actb (Mm00607939_s1)
Akr1b8 (Mm004841314_m1)
Calb (Mm00486647_m1)
Gad1 (Mm04207432_g1)
Npy (Mm01410146_m1)
Som (Mm00436671_m1)
5Htr3a (Mm00442874_m1)
Vip (Mm00660234_m1)
Custom Evf1 probe

```
Evf1-probe (0.1 µM):
                                         (SEQ ID NO: 7)
5' AGAGCTATGCGACTGTAGGCAAGCCAT Evf1-F (0.1 µM):
                                         (SEQ ID NO: 8)
5' GCATGGAAACTTGATACCTTGGT 3'

Evf1-R (0.1 µM):
                                         (SEQ ID NO: 9)
5' GCCTTTCAGAACTAGAAGGGATTTAAA 3'
```

SYBR-Green Primers for qPCR:

```
                                        (SEQ ID NO: 10)
Evf2-F    (0.2 µM, 5'-CTCCCTCCGCTCAGTATAGATTTC-3')

(SEQ ID NO: 11)
Evf2-R    (0.2 µM, 5'-CCTCCCCGGTGAATATCTCTT-3')

(SEQ ID NO: 12)
Umad1-F   (1.2 µM, 5'-CACAGGCACCCTTGAGTAAGT-3')

(SEQ ID NO: 13)
Umad1-R   (1.2 µM, 5'-CCCCCAGTCTTGGGCTACTG-3')

(SEQ ID NO: 14)
Lsm8-F    (0.8 µM, 5'-CTCAGCACTGTCCAACCTGTA-3')

(SEQ ID NO: 15)
Lsm8-R    (0.7 µM, 5'-TGATGTGGAGGAGGTACACAAG-3')

(SEQ ID NO: 16)
Rbm28-F   (1 µM, 5'-GTTTGACAGCTGATGGCACC-3')

(SEQ ID NO: 17)
Rbm28-R   (1 µM, 5'-CACACTGGAGAACGGACCAT-3')

(SEQ ID NO: 18)
Akr1b8-F  (1 µM, 5'-CCTGCCTGACATCCTGCTAT-3')

(SEQ ID NO: 19)
Akr1b8-R  (1 µM, 5'-GGAGATGTCCGTTCGCTTCT-3')

(SEQ ID NO: 20)
Ccnd2-F   (0.7 µM, 5'-CGTCCGGGTCTCTCCGTCGC-3')

(SEQ ID NO: 21)
Ccnd2-R   (0.7 µM, 5'-GCCGTTCACCTGTGTCCAACTGGC-3')

(SEQ ID NO: 22)
β-actin-F (0.3 µM, 5'-GCGAGCACAGCTTCTTTGC-3')

(SEQ ID NO: 23)
β-actin-R (0.3µ M, 5'-TCGTCATCCATGGCGAACT-3')
```

Transfections into Primary E13.5 GE

Luciferase Reporter and Expression Vectors

For all luciferase experiments, enhancers were cloned into the pGL3 promoter vector (Promega) using the KpnI and NheI restriction sites on the 5' and 3' sites, respectively. The Calb1 enhancers (site 1, site 2, and site 3), AkrR enhancers (site 1 and site 2), NPY enhancers (site 1 and site 2), and SST enhancer (site 1) were identified by MACS2 peak analysis of ChIP-seq (DNA sequences obtained from the UCSC genome browser). Primers were designed to PCR amplify enhancer sequences from C57BL/6J mouse genomic DNA into expression plasmids.

Expression plasmids for pCMV6-Akr1b8, pcDNA3-EGFP, or pENTR223.1-Dlx6, were purchased from Origene, Addgene, or DNASU, respectively. Subsequently, Dlx6 was amplified by PCR and cloned into the BamHI and EcoRI restriction sites on the pcDNA3 backbone. To generate the pCMV6-EGFP control plasmid, EGFP was PCR amplified and cloned into the pCMV6 empty using the restriction sites AscI and NotI.

Primary Embryonic Brain Ganglionic Eminence Transfections

MGE and CGE tissues were dissected from E13.5 Swiss Webster embryos, dissociated in L15 media by pipetting several times, and spun through a cell strainer for single cell preparations. Briefly, cells were seeded at a density of 2.5×10$^5$ cells per cm$^2$ (Flandin et al. 2011). One day prior to seeding cells, 24-well plates were coated with poly-L-lysine (30 µg/mL; Sigma) and laminin (5 µg/mL; Sigma), while 96-well plates were coated with poly-L-lysine (3 µg/mL;

Sigma) and laminin (5 μg/mL; Sigma). Initially, cells were seeded in neurobasal medium (DMEM/F-12 supplemented with L-glutamate, B-27 (Gibco), N2 supplement (Gibco), bovine pituitary extract (35 μg/mL; Life Technologies), mito+ serum extender (BD Biosciences), penicillin (100 U/mL; Gibco), streptomycin (100 μg/mL; Gibco), and glutamax (0.8 mM; Gibco)).

Specifically, for the Akr1b8 gene expression study, cells were seeded at 470,000 cells per well in a 24-well plate. 24 hours after culturing cells, the medium was changed to neuralbasal media without antibiotics and 1.4 μg of expression vector (pCMV6-AKR1b8) or control vector (pCMV6-EGFP) was transfected using Fugene 6 (Promega), as recommended in the user manual. Cells were harvested 48 hours after transfection for RNA isolation (PicoPure RNA isolation kit; Applied Biosystems) and RT-PCR to quantify Akr1b8 (Assay ID: Mm00484314) and 5Htr3a (Assay ID: Mm00442874) normalized to □-actin.

For all luciferase experiments, cells were cultured at a density of 78,300 cells per well in a 96-well microplate treated for tissue culture. Cells were allowed to attach for 24 hours before changing the medium to neuralbasal media without antibiotics. Transfections using Fugene 6 (Promega) were performed as recommended. Cells were harvested 48 hours after transfection with 1× passive lysis buffer (Promega) supplemented with 0.1% Digitonin (Sigma) for cell lysis. To ensure thorough cell lysis, lysates were subjected to two freeze-thaw cycles prior to performing Dual Luciferase Reporter assays (Promega). All transfections were normalized to the internal control expressing Renilla luciferase, performed at least in triplicate and a minimum of two times.

For Calb1 enhancer transfections, Applicant used five concentrations ranging from 20 ng to 240 ng of pcDNA3-Dlx6, where the total amount of expression plasmids was maintained at 240 ng using pcDNA3 EGFP as the control; 50 ng of pGL3 luciferase reporter containing Calb1 site 1, site 2, or site 3; and 5 ng of pRL null. For NPY and SST transfections, three concentrations ranging from 40 ng to 160 ng of pcDNA3-Dlx6 were tested, where the total amount of expression plasmids was maintained at 280 ng using pcDNA3 EGFP as the control, along with 50 ng of pGL3 luciferase reporter containing NPY site 1, NPY site 2, or SST site 4, and 5 ng of pRL null. For AkrR-enhancer transfections, optimal effects were obtained with 160 ng of pCMV6-Akr1b8 for CGE AkrRE1/2 and MGE AkrRE1, and 80 ng of pCMV6-Akr1b8 for MGE AkrRE2. The total amount of expressed plasmid DNA was maintained at 240 ng using pCMV6 EGFP as the control. For reporters, Applicant used 50 ng of pGL3 luciferase reporter containing AkrRE1/2 and 5 ng of pRL null.

For Farnesol (FOH; Sigma) and Geranylgeraniol (GGOH; Sigma) treated cells, 50 ng of each AkrR enhancer reporter plasmid and 5 ng of pRL null were used. FOH and GGOH were freshly prepared in DMSO (Sigma) at varying concentrations using serial dilutions. Neurobasal media without antibiotics was supplemented with a final concentration of 0.01, 0.1, 1, 10, or 100 μM for GGOH and 0.1, 1, 10, or 100 μM for FOH. Prior to adding transfection reagent/DNA mixture, the media was changed to that containing the respective concentration of metabolite.

Primer and Enhancer Sequences

The DNA sequences obtained from the UCSC genome browser are listed below. Enhancer sequences were PCR amplified from C57BL/6J mouse DNA using the following primers:

Calbindin1 enhancers: Site 1 (476 bp):

5' primer:
(SEQ ID NO: 24)
GAATTATAGGAAAACACAATCAAACAGG

3' primer:
(SEQ ID NO: 25)
CAGGAGGAATTTCTTTTCTGATTG (SEQ ID NO: 26)
GAATTATAGGAAAACACAATCAAACAGGTGAAGAAAAGGAACAAAACCA

TCCAGGATCTAAAAATGGAACTAGAAACAATAAAGAAATAACAAAGCAA

GACAACCCTGGAGTTAGAAAACCTAGGAAAGAAGTCAGGAGTCATAGAT

GCAAGCATCACGAACAGAATACAAGAGATAGAGGGAATCTCAGGTGCAG

AAGATACCATAGAAAGCACTGACACAACAGTGAAAGAAGACACAGAAAA

CAAAAAATTCCTAACCCAAAACATCCAGGAAATCCAGGATACAATGAGA

AAACCAAACCTAAGGATAACAGGTATAGAAGAGAGCAAAGATTCCCAAC

TTAAAGGGCCAGTAAATATCTTCAACAAAATTATAGAAGAAAACTTCCC

TAACCTAAAGAAAAAGATGCCCATGAACATACAAGAAGCCTACAGAACT

CCAAATAGACGCAATCAGAAAAGAAATTCCTCCTG

Site 2 (776 bp):

5' primer:
(SEQ ID NO: 27)
CTCTTCACAGCAATGAAACCCTAAGAC

3' primer: (SEQ ID NO: 28)
GCTGGTCATGTTTTGACTCTATTAATTGG (SEQ ID NO: 29)
CTCTTCACAGCAATGAAACCCTAAGACACTGTTTTTGGGATGGCCA

GTCTGCA

CTATCTGCAATTCTTTACCTAGTCTGTCAATACAAAGACCGAAATTTAAG

AGACACATTCCATGGCCAAGAATATCTTCAATATAAAGAAATCAGAATTA

AATTATCAAGGACTTCTACCTCTAGCCATGATGGACTCTTATACATCACT

ATAACTGTGCAAGAGATACAGATCCTGTCACTGCCGGCCACCTTACAGCA

GGTAGAGAAGGAACGGCATCATGATATGATAAGCCTAACAGCATCTTAGA

ATTTCTGGCTGAGAAGCGGCTCTGAGAAGGGAAGTGCACAGGAACAGGGC

TCGAGCACTTTTCATAGAGTCTCCCTGAGTGTGTGCTGATTCCCCATTGT

GAAACCGAGGAAAAGTGCCCATGGAATCTAGAAAAAGGCAACTGCTATCA

CAGCACTGAACTGGACGGTGTCTCTAAAGGCTCACAAAGGGCTGGGAGAC

GGAGAGGCGGCAAGCTTCCTAACTGGCATCCAAAGCCTTCGGCAGTCAGC

TCAGAAGAATCATACTGAAGGGCTAAGTTAGACTCAAAGGAAAGCTACTA

TACCCACCCAAATAAACTTTACAAATGAGTTGTAAAATGATCATGTACTC

AGAGTAACTGCTTCCTCATGTAAGATGTAACACTTCAAAGGAAAACTCAA

AAGCCAGGCTTTGTGCTCACACTGAATTAGAAACGTGGGCAAACCCAATT

AATAGAGTCAAAACATGACCAGC

Site 3 (364 bp):

5' primer:
(SEQ ID NO: 30)
CACAACCATCTGTAATGAGATCTGATGC

3' primer:
(SEQ ID NO: 31)
GATCAGTGAGTTTGAGGCCAGCC (SEQ ID NO: 32)
CACAACCATCTGTAATGAGATCTGATGCTTCTTCTGGGGTGTCTGA
AGACAGC
TCCAGTGTACTTACATATATAATAAATAAATAAATCTTAAAAAAAATAA
ATAAATTTCAGCATCCTAAGAGCACTGGCTACCCTTCCTGAGGATCTGGG
TTCAAGTCAGCTGTACTGTGAATCCTCTGGATTCTGAGCACTGCATGCAT
GCGCTGCACGGACATTACAGACATACATTCAGGCAAATGCTCATACACAG
AAAATAAAAGTAGATGAAATAGTTCTTGATATTTTTTTCTTGAGCCTTTT
TTTTTTTTTTTTGAGAGGGTCTCAACCATATCAGCCTGGCTGGCCTCAA
ACTCACTGATC AkrR enhancers: Site 1 (1062 bp):

5' primer:
(SEQ ID NO: 33)
ATCAGCCGATTCTGGGCAA

3' primer:
(SEQ ID NO: 34)
GCCGGGAGGTCTGCCA (SEQ ID NO: 35)
AGGTGCAGCGATCAGCCGATTCTGGGCAAAGCCAGCGCTAACCCG
CCAGAGC
TCCGAGGATCGATGGTGCAACACACCCCTTGTTCCCAGAGACCCCCGCCG
AGACTTGCATAGGACTTTGGCAAACTTGGGAAAGCAACTTTTCCCCAGGA
GTCAGGTGCCTGGAAGAAAGGGAACAGAACTAAGAAAGGGGAAAGCGAA
AGAGCCTGGGGAAAGGAGAAGGTCCGAGCGGGCTGGACGCCGCTGCTAGG
CCGGCCCGGCAGCGCAACCCCCCAGGGGAGAAAAGGATGCACAAAAGCC
TGGAGGCGAGTGGTGGGAGGCCAAATGAGAAGAGATCTCTGGGTCCTCCA
CCTTCCACCCAAGATCACGATCCCCGGGAAGTCACCAGCAGGGTCCCCGG
CCTCCCGCACCAGCTGCCGGCGTGCCCGAGTCAAACACGCTGGGAGCGTG
GCGGGGAGGAGGCGAGCTGGTTGCAGCGGTGCGCTCCTGTGCATTCCGGT
GGGGTCCGCAGGCTGGCAGGATCGTGCGCATTTCGAGCGCGTGCGGGAGC
GTGCGAGGGGCTGGGCAAGCTTGCAGCGCGCCAGGGTGGGAAAGACATCC
CGAATGCATCAGGTGCAGAGCCGGGAACCCACCGTGCGCGGCCGGGAGCG
CACAGCGAGCTCCCGCTCCACCGGCCGTTCCCACCGAGAGCCGAGGAGGA
CTCGGAGCGCCAGAGTCTCTCCGAAGCGTCCCTCTCTCCTTAAAAGAGGG
CATCAAGTCCAATCAAAAAAGAAGAAAAAAATCCCACCACGTTTTCTCT
AAAGAAAACAAAACCCGATCGGATACCAGTCCCCTCCCACCCGACCCCCA
GGTTCACTCCTTGCTTCCTCCGGGTCTAGCTCCCCAGCTCGCCAGCGAAT
AAACACAAATAAATAAGACACAATCCTATCTCACGCCAAGCGCACCGGTC
CGCATACATATGAGCACCCACAGGCTCTCTGCTCCTCCGCCAGCCCTTGC
CTGTACAAAGACACCCAGTCCCCGACTACACGCGCCCGCAGCCCTGGCAG
ACCTCCCGGC Site 2 (1667 bp):

5' primer:
(SEQ ID NO: 36)
GCTGCTGCCCCGGC

3' primer:
(SEQ ID NO: 37)
ACGGATTCTCTTTCTCTGATTTGAGG (SEQ ID NO: 38)
GCTGCTGCCCCGGCGGCAGCGGCTGCTGCTCGTTGGCTAGGTGGAG
AGGGCA
AAAGGTTGCAAAGGAAGAGGAGCCGCAGAGGACCTGGCAGTCCCCAAGGG
GTCAGAAGGATGAGTGGGAGAAGCGGTTCCCACTTTAGCCCCAGGTTTTT
TCATTTCCACTGGGCATGCGGTGTATCCCGCGCCCCTAACTCCCCCAACT
CCAGTACTCAAGAGCGCAGTTTTGTCCCGTTTTTTATTATTTGCACCAGT
TCAGTGTGTGGCTTCTAGCTTTTCACTTTTTCTCAGGATTCGGATCGCAT
CCTCCCTTACCCTAGCTTTAAATGGGTCGTTTCCCAAGTCCCAAACCAGG
CCTCTGATGCCTGACCACAGGAGTTCGCCGGATTTGGCCAGATAAATCTA
AAGGGGCCAGTAGAAATCTGGTAGGAGGCAGCACCTCGATTTTGCTATCT
AGATTGTTGCACACTGAGATGCGAAGGCCTGAGTAGTAATACTTTCTCAC
TCCTAATCTCGGGCATCCTCCCCGCCCGCACGCCCCCCCCCATCTTCCCC
GGCCCCAGGAACCTGGATGGAAAGTTCTGAAGATTCTGCGCCTAACTCAG
CTCTGCCTTCAGGAGCTACTGGAAGCTTGGAAGAGCGCTGGGCCGCTCCA
GAGTACTTTCTTCCCTCAGCGGCTGGACCATTTTAAAGGGCGTACTTGAG
ATGACAAACCGTAGGGTAGAAAGACCAAAGGAAAAAAAATATTCCTTCTA
CCCGCGGAAAGCACCGTCTCCTCCTTTGCACACGAAGCTAGGCAGGGAAT
TGAGGTTGGAGGGTTCTTTTCTGAGCACTGGCCTCCGGCCAAAGCCCCAG
CGCAGTGTTATTGGGGGTGTGGTGGAGAGCGCCACCCAGGGGTCTCAGAA
AAGTCACCCACACAGCCCCACCCTCCAGTCCTAAGGTATTAGTTCCAGGC
TTCAGTTTAGGGGTGCTGTGTTCTTGGCTTACCGCGGATCTCCCACAGGA
CCCACAGAATCGTATCTTGATTCCCCAGGAGCTAAAGGAGAAGGAAAGTG
GGCGGTGAATGGAGACAAAAAACCCACGAAGACCAGGTGGCAGAGCTTA
CACAAGATCTGCACGGGGGTCTGCTAACGTGGTGGTCATTTATAATAACA
AGGCATCCTAACAATTGACACTCCCAGGTCTCAGATTAGCAGTGGGAGAG
AGAAGTCCGCAGAACCGAGCACTGGGAAGCAAAGGAAGAAAACTACAATT
GAGTTACCCTCTCATAGGCAGTGTCATGTGGGTGAGACAAGGCGAAACCC
CCCTACCCCAGTCAGTTGGTATACAACAAAAAACACCTTGTGTAAAGGCT
ACCTGATTCTTTCAAGTTAAGGCGAACCCTCTGTAAGAAGTAGGGGATTT
GAGGACGTTAAGAAGGAACTGCCATCTATAAAGAAAGCAAGAGTGGATGA
GCAGAAGGGAACAGGAAAAACACACACCCCCCTGCCGTGAATGCCTGGCC

ATGGGAATGGAGCATTGAGCTTGTTGAGTTCCTGTCTAAAGAAGGCTTGC

TATCTAGGGTCCACATCCACCTACCACCCTCTCTCCAGCAGTCACCGGAG

AGGCACACGATTAACCTCTGATCCTATTCTACCATTAATCCTCAAATCAG

AGAAAGAGAATCCGT

NPY Enhancers: Site 1 (535 bp):

5' primer:
(SEQ ID NO: 39)
CTCAATCTCGGCATTGAATAGA

3' primer:
(SEQ ID NO: 40)
CATGATACCGTGAAGATTTAAGTTTG (SEQ ID NO: 41)
CTCAATCTCGGCATTGAATAGAAATTATCCCAAACAGTTCTTATTA

AATATCC

AGGTTATTCTGGGCCTTCGTGAGCATGGCAATTTCCTCAAAGCAGGATTT

AGAAAATCTGAGTCATAAGACCCATTTTTGTGCAAATTTCTCCAACAAAG

AAAAATGCATTTATAAACACCCCATTGAAGCTGCAGGAAGAGTAAGCAAA

AGGGTTGTTAGTGAATGAGCGATAGTACATGCATATCGGCAACAAAGAGC

CCGGTTATTAACCAAGGTGTGTGAAATGCCATTAACATGTTTTGATTTGA

TGGATCTTTAATATTATATTTTATGAATAGAAAAACTACTCAGAAAAATT

CCATTAGGCCACTTCCATTTTAATTATTTTAGCTTCTCAGATGTGAATTT

CTTTGTTGTTGGATGTCTGAGGGATTTAACCTCCCTGATGGACAGAGAAT

GCTGTAGTGACACAGTGACCAATGCCAGCTGTTCTGAGGCCACATCCTAC

ATCTGACAAACTTAAATCTTCACGGTATCATG

Site 2 (360 bp):

5' primer:
(SEQ ID NO: 42)
TTGAGTTCCTGTCCTGGCTTT

3' primer:
(SEQ ID NO: 43)
AAAAGTCATGTCTTCAAAAACAAACA (SEQ ID NO: 44)
TTGAGTTCCTGTCCTGGCTTTCTTTAGTGATAAACAGCTATGTGAA

GTGTAA

GCTGAACAAACCCTTTCCTCCCCAATCTGCTTTTTGGTAATGGTGTTTCA

CCACAGAAACCCCAAGGAAGACATGCAATACCCTGATAATTTATTCAAAT

ACATCTCCTAGCCTCTAACTTTCCCTTAAATTTTTCCTTGAGTCTCTGTA

ACCTCACTGTGTGGCATCTTCTTTCACATTGTGTGTGTGTGTGTGTGTGA

ATTCTACATAACTTTATTAAAGAATTTATACTTATACTTGTTAAGTATAT

CAAAGGAATTTCCAACCAGTAGTATCTAATTTGTTTGTTTTTGAAGACAT

GACTTTT

SST (Som) Enhancer: Site 4 (548 bp):

5' primer:
(SEQ ID NO: 45)
GAGCTCCCAGGGACTAAACC

3' primer:
(SEQ ID NO: 46)
CAGTGTTCTCTGGAATTTTCATTG (SEQ ID NO: 47)
GAGCTCCCAGGGACTAAACCACCAATCAAATGGAGAGACCCATGG

CTCCAGC

TACATATGTAGAAGAGGATGGCCTTGTCAGACATCAATGGGAGGAGAGGT

CCTTGGTTCTGTGAAGGCTGTATGCCCCCAGTGTACAGGAATGCCAGGGC

CGAGAAGTGGGAGTGGTTGGGTTGGTGAGCAAGGGGGAGGGGGGTAAGG

AATAGGGGGTTTTCAGAGGGAAAACCAGGAAAGGGGATAACATTTGAAAT

GTAAATAAAGAAAATATCTAATTAAAAACTTGTTTTTTTTTTTTTTAAA

AAAGAGTCAGCGTAAATGGCCTCTTCTCCCATACATCTACAAACAAAATC

ACTACTAGGAACAATTACACAGGACATTTATAATCAATCTCTCTAGCTTA

TATTCTCAAGGCAGCCTGTGAGGCTACTGAATCAATAAGGTTTTTTTTA

ATATTTTATCAGGCAATATATAAGTGAGATATTATAGATACTTTATCTAT

TAGGTAGATAATATTTCTTGATCAATGAAAATTCCAGAGAACACTG

DLX Binding Site in (Zbtb16-5Htr3a)

(SEQ ID NO: 50)
TCTTAAGTCTGAGGCTCACAGACCCTTATTTCACAGGTCAAAGGTCAAAG

GTCAACCAGTCAACGGTATTCTGAGGAAGTGCTGGCACAAAGATGAGCCC

ACTGGAGAGTTCCTCTACAAAGCAACTTCCGGGGAAATGGAGGCTATGT

ATACTACCCAGCCCAGCCTCCTACATTTTCTGCAGGTTTGGTGTCTGTCC

ACTTCCTTGGTTTGTTTTGTTTTGTTTTTTTGTTTTTGACACAAGATTTA

CAACCCTGACTCACCTTGAACTCACTCTGTAGCCCAGGCTGGCTCCAGGC

TCATGATCCCCTGCCTCGGCCTCTCGAATGCCAGGATCACAACATGTAC

TAACATGCTCAGCCCCCTGCATGGAGCTTCATGGGAAAGAAAACCTTTGA

ACGATGAGTGCTACCGCAGACCTCCACCCTAAACCAAAGCAAGTTCTTCA

GATGGCCCGAGGACACTTGAGAATGTTCCCTACCTTCTAAAGGTGACAT

TAGATCTTCCCAGAGAATGTTTCTTAATGTCAGCAGCCGTGTCATATTCC

AAGAGGGGTCATTAGTCACTCCTTGTGTCATTGTGCTATACATCACTCAA

GACTAAGCTGTTTCCATGTTCCTC

Proposed Human Homologs of the Enhancer Regions
Akr Enhancer Human Site 1 from Human.chr11

(SEQ ID NO: 55)
AGGCTTTGTA CCGCCAGGGG CTGGCGGAGC AACAGAGCCC

GTGGGTGCTC TTATGTATGC GGACCGGTGC GCCGGCGCAA

GATAAGGTTG TGGTTTATTT ATTTGTGTGT TTATTCGCCG

GCCGGCTGGG AAGCTAGAAT CGGAGGAGCT GACGAGTAGA

TCTGGGGGCG GAGGGGAGCA GGACTGGGAC TGCTTACGTT

-continued

```
TTGTTTCTCT TTGAGAAAAC GTGGTGGGCT TTTTCTTGAT
TGGACTTGAT CCCTACCCCC CTTTTGCAGG GGAGGGAGGG
AAGCTCCAGA GGGTCTGCAG CGCTGCGGGC CCTCCTCGGC
TCTCGGCGGG ACCGGCGGTG ACACCGGAGC TCGCCGTGCG
CTCCCGGCCG CTCTCGGTGG GTGCCGGTCT CTGCACCTGA
TGCGTTCGGG ATGCCTTTCC CACCCTGGCG CGCTCGCCGC
TAGCTCGCAC AGCGCCTCGC ACACTCCCGC ACGCGCTTGA
AATGCGCACG GTCCCGCCGG CCCGCGGAAC CACCCGGACG
CACGGAGCGC TCCGCACCGA CTCGCTCGCC GGCTCCCCGA
GACGCTCGCA CCGTGCTTGG GCCGGGCGCG CTGGCCGCTG
GCGCCGCTGG CCAGAGGCCT GGGACCCAGC CGGTCGCTCC
CAGGGGGTCA CGGCCCTGGG TCGGAGAGGG AGGGCGGGCA
GACCCCTTCT CGCCTTTCCT CCCACAACTC GCTGCGGGGC
TTTTGTGCTT CCCCTTCGCC GCGGGGCGGG TCCGCCTCCC
CTGCCGCTCT CGCCGCGGAG TCCAGCCCGC CCGGACTGTC
GCCGTTCCTC CCCGTCTCTT TCGCTTTCCC TCGTCCCTAG
CTCAGCTCTC CTTCTTTCAG GAGTCTAGCT CCTCGGGAAA
AGTTGCTTCC CCAAGTTTGC TGAAGTCGTC TCCAAGTCTC
GGTGGGGGTC GCTGGGAACT GGGGGGGTGT GAGAGCGCGG
TCGATCCCCG GAGCTCGGGC GGGTTATCGC CGG
```

Ark Site 2 from Human

```
                                      (SEQ ID NO: 56)
GgGGGTTAATt GTGTGCtTCT CCtGctACTG CacTGagGAG
AGGCTGGTAG GTGGATGTGG ACAGCAAAGC GGAAACCTCC
AGCAGGCACT ATCTAGGCAG AAGCTCAACA AGTGTAGTGA
TTCTTTCTTC TGTTTCCCTG GTGAGGCACC AGGAGGGTCT
TTTCTCCTCT CCTTACATCC CTCCACTCTT GCTCTCCTTG
CAGCCCAGTT CTTTCCTAAC TTTCTTTAAA TCCCTTTCCT
CTAACAGGGT GTATAGACCT TAGTTAGAAA AACAGGTAGT
CTCTAAATGG GATTGCTCTT TATTGTTAAT GAAATGAATA
CCCAGGGACT GGGCTTCCCC TCCGCTTGCC CTGGGTTTGA
TGTGGTTGTA TCCCGTGCTA TCAGAGGAGC CCTTCCTTCA
CTCAAGTGTG TTCCCCTGGC CAGCTCTCTC CGCAGACTCC
TGTTGGGCTG AGCTTTCCCT GCTCTTAAGA GTCAGGAGTG
GCTCTTGCTG GGATGGAATG ACCCGTCTTT GGGGCTGCCT
CATGAGCGGC TCTTGTGAAC CCGGATCAGT TCCGATGTGT
AAACTCTACC GCCTGGCCTT CAGCGAACAG ATACAGATTT
CTGCCACCTT CCATGACCCT ACAGTTCATG GGACTGGGTC
TGGGGCAGTG CCAGAGGCAC GCATGGAGGT GTGATTCTAG
GTGAGTCCTG CGGAAAACCT CTGGCCCACC CGTGAGTCAC
GGACAGAACA TGCAGACTCA GGCCTTGGTG ACATAAGCTC
CGCATTGCTA AAACGCGTG ACCTCGAGGG CTGACTGGCC
TGAGAACCCT GGATGGCGCT CTCGGCCACC CCCACCTCCC
ACCCCAACGT CCTGGGCTTC GGTCAGAATC CACAGCCCGT
GCCCGAAGAG CGCTTCCCGC CTCTGGCACC CTACCTTCGC
TCAGCTCCAG GGAAAAGGGG AGAGGGCAGC TTTCTGCAGT
CAGAGGAAGA GTACATTTTC TTTGGCTGCT CTACCCTCTG
AAGTAGGGCG GCCAGCTGAA GGAGGACACA CTTTTGAGGG
GCCCAGAGGT TGTCCAAGCT TCCCCCTGCC CCCTGAAGAC
TGTGCACTGA GCTGGGCGCA GTTCTCGGGA ACTGTTTCCA
CCCAGATTGC TGGGGGGCGG GGGGGTAGGA TGAGGGCAGA
GCCGAGAGGC TGTCCAAGGT TTGGGAGAGA GAAAAGTTTC
TGCCAGGACT CGACGTTGGC CTCCAGCAAT CGCGACAGCT
AAAAACGGGT GTCTCGCTTC GACAATAGAT CCCCGCGGAC
CTTCTGGCAC CTGGTTCACT AGCGCCCGCG AACTCTGCCT
CGGGAGACTT ATTGAAATCC GGATGCTCAA GCCGGGAGGC
GCGCAGTAAC CAGGAGGATG AGAGGGCCGG GTTTGGGCTA
GGAAAGCGGC CTTTTAAAAC AGATGTCAGG GGGACTGCAG
CCCCGAGCCA TGAGAAAAAA GTTAAAGGCG AGATGACACG
GACTGAATTG GGCAAACAT TGGAAGAGGA GACAAAACTG
CGTGCTTGAG CACCGGGGTG CGGGGAGGGG GCGACAAAAC
CCGTATCCAG TGCAAATTAA AATCTTGGGA GTAGGTGGGG
GCTGCTGCGC GCCCTTCACC CTCAGTTCCC CTATTAAGGA
TTCTGAGTCC CCATGCACTC CTCTCCTCTG GCTCCTTCCT
TCCTCTCCGC TCGGCCGGTG AGAGGCGGCC GC
```

DLX Binding Site in Human Chromosome 11

```
                                      (SEQ ID NO: 57)
AAGACAGAGA TAAAGACATA GTTCTTGCCC CCACAGAGTG
TATAGTCTTA AGGAACTTAT AAATGGCTTA GTCTTGAATC
TTGAACTTAA TATTCCTACA AAATACATAA GGAGAATGAC
ACTGGGTGTG ACTAATGGCC TACTTAGCCT GGAATGTGGT
ACTTTTGGTG GCATGAAGAG ACATTCCTTG GGAAGACATG
ATGTCACCCT TAGAAGGAAG GGAACATTCC CCAGAGTATC
CCTGATGCCC TATGAATAAC ATGGTCTGGC TTAGGGTAGA
GGCCGCTAGT AGAACAGGCT CTGTTTAGAG TATTCCTTTT
ACACAAAAAG ACACATAGAA AGTACAGGAG AGCTAGTCTG
GGCGTGGTGG CTCATGCCTG TAATTTCAGC ACTTTGGGAG
GCCAAGATGG GAGGATCACT TGAGCCTAGG GGTTCAAGAC
CAGCCCAGAC AACATAGCAA GACCCTCGTCT CTATTAAAAA
CAATTATTTA AAAAGAAAG TACAGGAGAA TGGACTGAAT
```

-continued

```
ATGGAAACAC TCTGCAGTCT CCCTGGAAGT TGCTTTGGGG

AGGAAATACT GATAGCCTCA TAACTTTGCA TTCATCCCTT

CCTCTTAAAA TTAGAGCACA GAATGCCGTT GACTATTTCA

CCTTTCCTTT GTCATTTGAA TTAAAGGTAA ATGGACGTTG

AAAGTGTGTT TTTGACTTAA AGGTCTAAGG AGGAAGAGTG

AGCCCATTGC TAAAGTACAT AAGCTTTCCC TTTACTCAAT

TCTGTGTCTA CTTGGAAAGG TGAATGAGGC TAGGGCAAGG

TTCTCTTA
```

NPY-DLX6 Enhancer Site 1 Human Chromosome 7

```
                                    (SEQ ID NO: 58)
GCAATTTCCC AGAGGCAGGA TTTAGGAACT CTGAGTCATA

AGGCCCATTA TTGTGCAAAT TTCTACAACA AAGCAAAATG

AATTTATAAA CATCCTATTG AAGCTCTAGG AAAAGTAAGC

AAGAAAGTTT TTAGCAAGTG AGGAATAGTA CATGGAAATT

AGTAATGCAG ACTCACTGTT ATTAATTGAA GGTATGTCAA

ATGTCATTTA TTTCTTTTTT TTTTTTTTTT ACCTTTATGT

CTCAAGTGGG
```

NPY-DLX6 Enhancer Site 2 Human Chromosome 7

```
                                    (SEQ ID NO: 59)
GCATGCTGAA TAATTTATTC AAATCTTTCT TCTAGTTTCT

GAATTTCTCT TCAGTGGGTC CTTGAGCCCT TACTACCTCA

GTGTAGTAAG TGTACCCATC TATCTTTTGT GTTCTGCTTC

CCTGTGGAAA CTCCATATAA CTTGGATTGT GGGAATGATC

CTTCAGAGCA GCTTTGTATT TATATTTGCC AAGTATGCCA

GGGGAATCAC CAACCATCT
```

SST-Dlx6 Regulator Enhancer Site 1 Human

```
                                    (SEQ ID NO: 60)
AAATGTCTCT TTCTCCTATG GACAAAGTTA CTGTAAGAAA

CAATAAAACA AGAAAAAAAC CTTACAAACT CTCCAGTTTA

TATTCTTCAC AAGCTATGTG AAGCTATTGC ACATGTTTGT

GTGTGTGTGT GTGTGTGTGT GTGTATCATT ACATCAGGCA

ATGTGGAAAA AAAA
```

Chromatin Immunoprecipitation (ChIP)

For ChIP experiments whole ganglionic eminences were dissected from 10 Evf2$^{+/+}$ and 10 Evf2$^{TS/TS}$ E13.5 embryos. Tissues were pooled for each genotype, triturated by pipetting, and filtered through a cell-strainer capped 5 ml polystyrene round-bottom tube (BD Falcon) to make single-cell suspensions. Duplicate ChIP experiments were performed to determine reproducibility, generating libraries as described below.

Native Chromatin

Native ChIP protocol has been described in detail previously (Brind'Amour et al. 2015), and detailed for E13.5 GE cells as follows. Cells from the single cell suspension described above were split into 1×10$^6$ cell aliquots, and pelleted through centrifugation at 1000×g for 10 min. Cell pellets were flash frozen in liquid nitrogen, and stored at −80° C. Nuclei were isolated using EZ Nuclei Isolation Lysis Buffer (N3408, SIGMA). Chromatin was digested in 2 U/μl Micrococcal nuclease (M0247S, NEB) at 37° C. for 7 min. The reaction was quenched with EDTA (10 mM final concentration). Triton X-100 and Sodium Deoxycholate were added (0.1% final concentration). Samples were incubated on ice for >15 minutes. Immunoprecipitation buffer (20 mM Tris-HCl pH 8.0, 2 mM EDTA, 150 mM NaCl, 0.1% Triton X-100, 1× Protease inhibitor cocktail, 1 mM PMSF) was added to a final volume of 200 μl and the samples were rotated at 4° C. for 1 hour. The chromatin was pre-cleared by rotating at 4° C. with 15 μl of Protein G-Agarose beads for 1 hour. After centrifugation to pellet the beads, the supernatant was further pre-cleared by rotating at 4° C. with 15 μl rabbit IgG conjugated Protein G-Agarose beads for 1 hour. The pre-cleared chromatin was incubated with rabbit IgG (1 μg), or antibodies targeting histone modifications (1 μl) at 4° C. for 1-2 hours with rotation. 15 μl of Protein G-Agarose beads blocked with 1% BSA in 1×PBS were added to each sample and incubated at 4° C. overnight with rotation. The beads were pelleted by centrifugation and washed twice with 200 μl Low Salt Wash buffer (20 mM Tris-HCl pH 8.0, 2 mM EDTA, 150 mM NaCl, 1% Triton X-100, 0.1% SDS) and twice with 200 μl High Salt Wash buffer (20 mM Tris-HCl pH 8.0, 2 mM EDTA, 500 mM NaCl, 1% Triton X-100, 0.1% SDS). Immunoprecipitated DNA was eluted in 100 μl of ChIP elution buffer (100 mM NaHCO3, 1% SDS) at 65° C. for 1-1.5 hour. The DNA was purified using phenol chloroform extraction and ethanol precipitated. The pellet was resuspended in 10 mM Tris-HCl pH 8.5. The DNA was incubated with 20 mg of RNAse A at 55° C. for 1 hour. 40 mg Proteinase K were added and incubated at 55° C. for 1 hour. The immunoprecipitated DNA was purified using the Qiaquick PCR Purification Kit.

Antibodies: ChIP antibodies targeting histone modifications are Encode verified: H3K4me3 (Abcam ab8580), H3K4me1 (Abcam ab8895), HeK27me3 (Active Motif 39155).

Cross-Linked Chromatin

For anti-DLX and anti-H3K27ac ChIP cells were fixed in 1% paraformaldehyde for 10 min then lysed in SDS lysis buffer (1% SDS, 50 mM Tris-HCl pH 8, 10 mM EDTA) with protease inhibitors (11836153001, Roche). The lysates were sonicated with a Bioruptor Pico (Diagenode) for 10 cycles (30 sec On, 30 sec Off). The lysates were then centrifuged to pellet cellular debris and the supernatant collected for ChIP. 25 μg of chromatin were diluted 1:10 in RIPA Buffer (10 mM Tris pH 7.6, 1 mM EDTA, 0.1% SDS, 0.1% Sodium Deoxycholate, 1% Triton X-100) with protease inhibitors (B14002, Biotool). The chromatin was pre-cleared by rotating at 4° C. with 50 μl of Protein G-Agarose beads (11719416001, Roche) for 1 hour. After centrifugation to pellet the beads, the supernatant was further pre-cleared by rotating at 4° C. with 50 μl rabbit IgG conjugated Protein G-Agarose beads for 1 hour. The pre-cleared chromatin was incubated with rabbit IgG (2.5 μg), previously validated anti-pan-DLX (2.5 (Feng et al. 2006; Bond et al. 2009; Cajigas et al. 2015)) or anti-H3K27ac (1 Abcam Ab4729) at 4° C. for 4 hours with rotation. 50 μl of Protein G-Agarose beads blocked with 1% BSA in 1×PBS were added to each sample and incubated at 4° C. overnight with rotation. Beads were pelleted by centrifugation and washed twice with Low Salt Buffer (20 mM Tris-HCl pH 8.1, 2 mM EDTA, 150 mM NaCl, 0.1% SDS, 1% Triton X-100), three times with High Salt Buffer (20 mM Tris-HCl pH 8.1, 2 mM EDTA, 500 mM NaCl, 0.1% SDS, 1% Triton X-100), four times with LiCl buffer (0.25M LiCl, 10 mM Tris-HCl pH 8.1, 1 mM EDTA, 1% sodium deoxycholate and 1% NP-40), twice with 0.1% Tween-20 in 1×PBS, and once with TE buffer (10 mM Tris-HCl pH 8.1 and 1 mM EDTA). Immunoprecipitated DNA was eluted from the beads by incubation with 200 µl of elution buffer (50 mM Tris-HCl pH 8, 10 mM EDTA, 1% SDS) at 65° C. for 1 hour. The beads were removed by centrifugation and DNA crosslinking was reversed at 65° C. for 4 hours. The DNA was incubated with 20 mg of RNAse A at 55° C. for 1 hour. 40 mg Proteinase K (3115879001, Roche) were added and incubated at 55° C. for 1 hour. The Immunoprecipitated DNA was purified using the Qiaquick PCR Purification Kit (Qiagen).

ChIP-Seq Library Preparation, Sequencing and Analysis

Quantity of ChIP'd DNA was determined using Picogreen Reagent (Quant-iT™ PicoGreen dsDNA Assay Kit, Thermo Fisher P11496) and a fluorometer instrument. 150 ng to 1 ug of DNA was prepared into Illumina libraries, according to manufacturer's instructions, using the TruSeq Nano DNA Library Prep Kit (Illumina, FC-121-4003). Resulting libraries were deep sequenced, using the Illumina HiSeq2500 system in Rapid Run mode, obtaining between 10M and 15M of 100-bp length, single-end reads per library.

ChIP-Seq Read Alignment

Raw sequencing reads for all the individual ChIP-seq datasets were aligned using bwa (Li and Durbin 2009) (version 0.7.12) mapper with the following settings 'aln-t 8 samse'. Applicant allowed two mismatches relative to the reference and only retained the unique alignments with Phred quality score greater than 30 as done in the previous study (Marinov et al. 2014). The datasets were mapped against mm9 version of the mouse genome.

ChIP-Seq Data Analysis

Quality Assessment

ChIP-seq quality assessment was carried out using the strategy described by ENCODE ChIP-seq data analysis guidelines (Landt et al. 2012). Cross-correlation analysis was performed using SPP package (Kharchenko et al. 2008) using the parameter '-s=—100:5:600'. The analysis is essential to assess the NSC (Normalized Strand Correlation) and RSC (Relative Strand Correlation) values as recommended by ENCODE (Landt et al. 2012). As per the guideline, all of our selected ChIP-seq datasets are above NSC value (>1.05) and RSC value (>0.8) threshold, and subsequent QC scores equal to or above 1 (Landt et al. 2012; Marinov et al. 2014).

Peak Calling and Differential ChIP-Seq Analysis

After quality assessment, Applicant used "irreproducible discovery rate" (IDR) frame-work to call the peaks against their respective input ChIP libraries using MACS2 program (Feng et al. 2011) as described in the ENCODE guidelines (Landt et al. 2012). MACS2 peak calling was performed using the following settings '-p 1e-3-to-large-nomodel-shift-size' while rest of the parameters were set to their default mode. The final conservative set of peaks for all the samples were called across technical replicates with an IDR threshold of 0.01.

Differential ChIP-Seq Analysis

Differential ChIP-seq analysis between two conditions was performed using MACS2 program (Feng et al. 2011) by treating one of the samples as the control for the other. The peak identification by MACS2 was carried out using the same parameter settings as previously described in ChIP-seq data analysis part. The cross-correlation analysis step (Kharchenko et al. 2008) was also performed on the respective datasets to determine the 'shiftsize' parameter essential for peak identification by MACS2.

Chromosome Conformation Capture Using Dlx5/6UCE as Bait (4Cseq)

Whole ganglionic eminences (GE's) were dissected from 10 Evf2$^{+/+}$ and 10 Evf2$^{TS/TS}$ E13.5 embryos (schematic in Fig S2, GE=LGE+MGE+CGE). Tissues were pooled for each genotype, triturated by pipetting, and filtered through a cell-strainer capped 5 ml polystyrene round-bottom tube (BD Falcon) to make single-cell suspensions. Cells were fixed in 2% paraformaldehyde/10% Fetal Bovine Serum (FBS) at room temperature for 10 min with rotation. 125 mM glycine was used to quench the formaldehyde. The 4C method used has been described in detail (van de Werken et al. 2012). EcoRI was used for the primary restriction digestion and DpnII was used for the secondary restriction digestion.

The following steps were performed to generate the 4C library for sequencing. First, overhangs were added to the 4C template using PCR amplification with primers containing the bait sequence.

Primers:

```
Dlx5/6UCE Forward:
                                       (SEQ ID NO: 48)
5'TCGTCGGCAGCGTCAGATGTGTATAAGAGACAGATGCCAAACCACTGT

GAGTGTA3'

Dlx5/6UCE Reverse:
                                       (SEQ ID NO: 49)
5'GTCTCGTGGGCTCGGAGATGTGTATAAGAGACAGGTCCCCAATGTCTG

CTTCAA 3'.
```

PCR reaction: 200 ng 4C template, 0.2 mM dNTPs, 35 pmol Primer Dlx5/6UCE-Fwd, 35 pmol Primer Dlx5/6UCE-Rev, 1.75 U Expand Long Template Enzyme Mix (Roche), 1× Buffer I. PCR cycles: 94° C.—2 min, 94° C.—10 sec, 55° C.—1 min, 68° C.—3 min, 29 cycles, 68° C.—5 min. The PCR product was purified using the High Pure PCR Product Purification Kit (Roche). Then, the 4C DNA containing the overhangs was used as template for a second PCR that adds index sequences and Illumina sequencing adapters to generate the 4C library for sequencing. PCR reaction (50 µl): 225 ng DNA template, 0.5 mM dNTPs, 5 µl Nextera XT Index1 primer (N7XX, Illumina), 5 µl Nextera Index 2 primer (S5XX, Illumina), 3.5 U Expand Long Template Enzyme Mix (Roche), 1× Buffer I. PCR cycles: 94° C.—5 min, 94° C.—10 sec, 55° C.—30 sec, 68° C.—1 min, 8 cycles, 68° C.—7 min. The PCR product was purified using the High Pure PCR Product Purification Kit (Roche).

4Cseq Reads Mapping 4C sequencing reads for all the samples were aligned on a reduced mm9 version of mouse genome using bowtie2 alignment program (Langmead and Salzberg 2012). The reduced genome consists of only EcoR1 (+/−50 base-pair) cut-sites. These EcoR1 sites were selected based on the presence of a second restriction enzyme cut-site i.e. DpnII, within its +/−500 base-pairs. Applicant trimmed the 5' end of the raw reads to remove the bait sequence before mapping on to the reduced genome. Applicant allowed two mismatches outside the EcoR1 sequence in the reduced genome during mapping and only retained chromosome 6 specific unique alignments with Phred quality score greater than 30.

4Cseq Differential Data Analysis 4C reads mapped at the EcoR1 restriction site resolution on chromosome 6, were further filtered based on their reproducibility in each pair of replicates. An EcoR1 cut-site was deemed reproducible if the two replicates in a given condition (Evf2$^{+/+}$ and Evf2$^{TS/TS}$) have either both non-zero counts or both zero counts. By applying this criteria, Applicant retained a total of 997 reproducible EcoR1 restriction cut-sites across the replicates of the two conditions. Applicant then performed a DESeq2 (Love et al. 2014) based differential contact count analysis on these sites to obtain condition specific significantly higher (p-adjusted value≤0.05 and a log 2 fold change≥2 for Evf2$^{+/+}$ or ≤−2 for Evf2$^{TS/TS}$) and conserved (p-adjusted value>0.05) 4C interaction sites.

Histone Lysine Methylation (ChIP-Seq) Determination at Dlx5/6UCE Interaction Sites (4Cseq)

To interrogate the interplay between changes in chromatin contacts and changes in local chromatin landscape (e.g., histone modifications), Applicant computed ChIP-seq signal density of three different histone marks (H3K4me3, H3K4me1 and H3K27me3) near each reproducible EcoR1 cut-site. Using "bedtools intersect" (Quinlan and Hall 2010) in both Evf2$^{+/+}$ and Evf2$^{TS/TS}$ conditions, surrounding regions of each cut-site were scanned from +/−1 kb to +/−10 kb at every 125 base-pair interval to gather average ChIP-seq signal for each mark. For each window size, the distributions of sequencing depth normalized ChIP-seq read counts from each condition were compared against again other. Depending on whether the same or different sets of 4C sites are being compared between the two conditions, either a paired (FIG. 4G, H, I) or an unpaired (FIG. 4F) T-test was performed for window sizes of +/−2 kb, 6 kb and 10 kb to test the difference in histone modifications between the two conditions.

Human/Mouse specific Dlx5/6UCE—Gene Interaction and Conservation Analysis

Applicant has used the preprocessed hiclib (*bitbucket.org/mirnylab/hiclib) normalized human cortex Hi-C data (Won et al. 2016) (GSE77565; ftp.ncbi.nih.gov/geo/series/GSE77nnn/GSE77565:suppl/GSE77565_FBD_IC-heatmap-chr-10k.hdfs.gz) at 10 kb resolution to first extract all the Evf2 (chr7:96,594,838-96,643,377 in hg19) interacting genic regions (gene+/−500 Kb) from human chromosome 7. At 10 kb resolution the human Evf2 region is distributed within five Hi-C bins (9660 to 9664), and any of the Evf2 bin with non-zero normalized interaction count with a genic region was considered for further processing in the downstream analysis. Applicant also extracted the Evf2$^{+/+}$ and Evf2$^{TS/TS}$ 4C interacting genic regions from mouse chromosome 6 in the similar manner. In the next step, Applicant used "liftOver" (Kent et al. 2002) tool to get the list of conserved Evf2 interacting genic regions among human cortex (Hi-C), mouse-Evf2$^{+/+}$ (4C) and mouse-Evf2$^{TS/TS}$ (4C) conditions.

Circular Visualization, Density, Histone Peak Plots and Gene Ontology Analysis

Circular visualization of integrated 4C and histone mark data were generated using circos software package (Krzywinski et al. 2009). The density plots were generated using R "smoothScatter" and "bkde2D" package (Wand 1994). Wash U Epigenome Browser (Zhou et al. 2011) was used to plot the histone peaks and their signal intensities. Gene ontology analysis of Evf2$^{+/+}$, Evf2$^{TS/TS}$, (+), (−) and (I) Dlx5/6UCE interacting sites were performed using AmiGO2 browser. An adjusted p-value threshold of 0.05 was used to filter out significant ontology enrichments of each gene set (Gene Ontology 2015).

Self-Organizing Maps

SOMs were generated in the Matlab neural network toolbox (NNT) using three training iterations to optimally cluster gene-distance data and visualization: www.mathworks.com/help/nnet/gs/cluster-data-with-a-self-organizing-map.html). The NNT provides algorithms and applications to create and visualize neural networks, including methods for clustering data www.mathworks.com/help/nnet/index.html.

Fluorescent In Situ Hybridization (FISH) of E13.5 GE Nuclei

DNA FISH

The DNA FISH method was adapted from a detailed lab protocol provided by Dr. Jerold Chun (Scripps, LaJolla, Calif.) (Westra et al. 2008). Single cell suspensions from whole GE's were made as described above. Cell pellets were gently resuspended in 500 μl Nuclear Extraction Buffer (0.32 M sucrose, 5 mM $CaCl_2$, 3 mM Mg $(Ac)_2$, 0.1 mM EDTA, 20 mM Tris-HCl pH 8.0, 0.1% TritonX-100) and incubated on ice for 10 min. Cells were centrifuged at 100×g for 2.5 min at 4° C. and the supernatant was removed. Cells were washed gently with ice-cold 1×PBS with 2 mM EGTA. Cells were centrifuged at 100×g for 2.5 min at 4° C. The supernatant was removed and cells were gently resuspended in 500 μl of ice-cold fixative (3 Methanol: 1 Glacial Acetic Acid). The cells were fixed for 10 min on ice. 5 μl of cells in fixative were transferred to Superfrost Plus microscope slides (Fisher Scientific) and allowed to air dry. The slides were transferred to a slide holder, vacuum-sealed and stored at −80° C.

Slides were incubated with 100 μg/mL RNase at 37° C. for 30 min. Cells were washed twice with 2×SSC (0.30 M NaCl buffer. 0.030 M trisodium citrate) for 2 min, treated with 50 μg/mL pepsin in 0.01 M HCl at 37° C. for 7 min, and washed twice with 2×SSC for 2 min. Cells were fixed in 1% paraformaldehyde for 10 min at room temperature and washed 3 times with 2×SSC for 5 min. The slides were dehydrated by incubation for 2 min in 70%, 80% and 100% ethanol. 200 μl denaturation solution (70 formamide in 2×SSC) was added and the slides were incubated at 85C° C. for 10 min. Slides were dehydrated in ice-cold 70%, 80% and 100% ethanol for 2 min and allowed to air dry. 150 μl pre-hybridization buffer (50% formamide, 0.1% SDS, 300 ng/ml Salmon Sperm DNA, 2×SSC) were added and the slides were incubated overnight at 37° C.

DNA FISH probes were generated by nick translation using the FISH Tag DNA Kit (Thermo Fisher Scientific) following manufacturer's instructions. The templates for the nick translation reactions were obtained from the BACPAC Resources Center (Children's Hospital Oakland Research Institute): Dlx5/6 region: WI1-1693G2, Umad1 region: WI11946E1, Akr1b8 region: RP23-120B14. DNA probes in hybridization buffer (50% formamide, 10% dextran sulfate, 0.1% SDS, 300 ng/ml Salmon Sperm DNA, 2×SSC) were denatured in the presence of 2 μg Mouse Hybloc DNA (Applied Genetics Laboratories) at 80° C. for 7 min and re-annealed at 37° C. for 1 hour. Slides were incubated for 5 min in 2×SSC with 50% formamide, 2 min in 4×SSC with 0.1% Tween-20 and 2 min in 2×SSC at 45° C. The slides were dehydrated in ethanol and denatured as described above. 10 μl of FISH probe solution were added, the coverslips were sealed with rubber cement and the slides were incubated overnight at 37° C. Slides were incubated in 2×SSC with 50% formamide for 10 min (3 times), in 2×SSC for 10 min and in 2×SSC with 0.1% NP40 for 5 min at 45° C. The slides were rinsed with 1×PBS, incubated with 5 mg/ml DAPI for 5 min, rinsed again and mounted using SlowFade Gold antifade reagent (Thermo Fisher Scientific).

Combined RNA and DNA FISH

Slides containing cell nuclei were prepared as described above. Slides were incubated with 50 μg/mL pepsin in 0.01 M HCl at 37° C. for 7 min, and washed twice with 2×SSC. Cells were fixed in 4% paraformaldehyde for 5 min at room temperature and washed 3 times with 2×SSC for 5 min. The slides were incubated in 1×PBS with 1% hydrogen peroxide for 30 min at room temperature and rinsed twice with 2×SSC. The slides were dehydrated by incubation for 2 min in 70%, 80% and 100% ethanol. 200 μl denaturation solution (70% formamide in 2×SSC) were added and the slides were incubated at 85° C. for 10 min. Slides were dehydrated in ice-cold 70%, 80% and 100% ethanol for 2 min and allowed to air dry. 150 μl pre-hybridization buffer (50% formamide, 0.1% SDS, 300 ng/ml Salmon Sperm DNA, 2×SSC) were added and the slides were incubated overnight at 37° C.

DNA FISH probes were generated as described above. The digoxigenin labeled RNA probe was generated as described previously (Feng et al. 2006). DNA probes and RNA probe in hybridization buffer (50% formamide, 10% dextran sulfate, 0.1% SDS, 300 ng/ml Salmon Sperm DNA, 2×SSC) were denatured in the presence of 2 μg Mouse Hybloc DNA (Applied Genetics Laboratories) at 80° C. for 7 min and re-annealed at 37° C. for 1 hour. Slides were incubated for 5 min in 2×SSC with 50% formamide, 2 min in 4×SSC with 0.1% Tween-20 and 2 min in 2×SSC at 45° C. The slides were dehydrated in ethanol and denatured as described above. 10 μl of FISH probe solution was added, and coverslips were sealed with rubber cement and the slides were incubated overnight at 37° C.

Slides were incubated in 2×SSC with 50% formamide for 10 min (3 times), in 2×SSC for 10 min and in 2×SSC with 0.1% NP40 for 5 min at 45° C. The slides were rinsed with 1×PBS and incubated in 1% blocking solution (Tyramide Signal Amplification Kit, Thermo Fisher Scientific) for 1 hour. Mouse monoclonal anti-Digoxigenin (Roche) was diluted 1:400 in blocking reagent, added to the slides and incubated at 4° C. overnight. Slides were washed 3 times in 1×PBS for 3 min at room temperature, incubated with 1:100 HRP-goat anti-mouse IgG in blocking solution for 1 hour and tyramide labeled according to manufacturer's instructions (TSA Kit, Thermo Fisher Scientific). The slides were washed 3 times with 1×PBS for 3 min, incubated with 5 mg/ml DAPI for 5 min, rinsed with 1×PBS and mounted using SlowFade Gold antifade reagent (Thermo Fisher Scientific).

Confocal Microscopy

Cells were visualized using a Zeiss Laser Scanning Microscope 880 and a 100× immersion oil objective. Z-stacks of 0.3 μm intervals were taken using the Zen 2.1 software. To measure interprobe distances, a line was traced from the center of one probe to the center of the adjacent probe. Distances were measured only between probes on the same z-slice.

Sequences

SEQ ID NO: 1 (Akr1b10) human protein (LOCUS CAG46600 316 aa linear PRI 26-JUL-2016)

DEFINITION AKR1B10, partial [Homo sapiens].

ACCESSION CAG46600

VERSION CAG46600.1 GI:49456559

SOURCE Homo sapiens (human)

ORGANISM Homo sapiens

```
matfvelstk akmpivglgt wksplgkvke avkvaidagy
rhidcayvyq nehevgeaiq ekiqekavkr edlfivsklw
ptfferplvr kafektlkdl klsyldvyli hwpqgfksgd
dlfpkddkgn aiggkatfld aweameelvd eglvkalgvs
nfshfqiekl lnkpglkykp vtnqvechpy ltqekliqyc
hskgitvtay splgspdrpw akpedpslle dpkikeiaak
hkktaaqvli rfhiqrnviv ipksvtpari veniqvfdfk
lsdeematil sfnrnwracn vlqsshledy pfdaey
```

SEQ ID NO: 2 (Akr1b10 human) DNA
```
atggccacgt ttgtggagct cagtaccaaa gccaagatgc
ccattgtggg cctgggcact tggaagtctc ctcttggcaa
agtgaaagaa gcagtgaagg tggccattga tgcaggatat
cggcacattg actgtgccta tgtctatcag aatgaacatg
aagtggggga agccatccaa gagaagatcc aagagaaggc
tgtgaagcgg gaggacctgt tcatcgtcag caagttgtgg
cccactttct ttgagagacc ccttgtgagg aaagctttg
agaagaccct caaggacctg aagctgagct atctggacgt
ctatcttatt cactggccac agggattcaa gtctggggat
gaccttttcc ccaaagatga taaaggtaat gccatcggtg
gaaaagcaac gttcttggat gcctgggagg ccatggagga
gctggtggat gaggggctgg tgaaagccct tggggtctcc
aatttcagcc acttccagat cgagaagctc ttgaacaaac
ctggactgaa atataaacca gtgactaacc aggttgagtg
tcacccatac ctcacacagg agaaactgat ccagtactgc
cactccaagg gcatcaccgt tacggcctac agcccctgg
gctctccgga tagacctttgg gccaagccag aagaccttc
cctgctggag gatcccaaga ttaaggagat tgctgcaaag
cacaaaaaa ccgcagccca ggttctgatc cgtttccata
tccagaggaa tgtgattgtc atccccaagt ctgtgacacc
agcacgcatt gttgagaaca ttcaggtctt tgactttaaa
ttgagtgatg aggagatggc aaccatactc agcttcaaca
gaaactggag ggcctgtaac gtgttgcaat cctctcattt
ggaagactat cccttcgatg cagaatat
```

SEQ ID NO: 3 (Akr1b8) mouse (NM_008012)
MATFVELSTKAKMPIVGLGTWKSPPNQVKEAVKAAIDAGYRHIDCAYAYC NENEVGEAIQEKIKEKAVQREDLFIVSKLWPTCFEKKLLKEAFQKTLTDL KLDYLDLYLIHWPQGLQPGKELFPKDDQGRILTSKTTFLEAWEGMEELVD QGLVKALGVSNFNHFQIERLLNKPGLKHKPVTNQVECHPYLTQEKLIQYC HSKGISVTAYSPLGSPDRPSAKPEDPSLLEDPKIKEIAAKHEKTSAQVLI RFHIQRNVVVIPKSVTPSRIQENIQVFDFQLSDEEMATILSFNRNWRACL LPETVNMEEYPYDAEY"

SEQ ID NO: 4 Akr1b8 mouse cDNA
Mouse Akr1b8 cDNA from origene
```
ATGGCCACGTTCGTGGAACTCAGTACCAAAGCCAAGATGCCCATTGTGGG
CCTGGGCACCTGGAAGTCTCCCCCCAAACCAAGTCAAAGAAGCTGTGAAGG
CGGCCATTGACGCTGGGTATCGCCATATCGACTGCGCGTATGCCTATTGC
AACGAGAATGAGGTGGGAGAAGCCATCCAAGAGAAGATCAAAGAGAAGGC
TGTGCAGCGGGAGGACCTCTTCATTGTCAGCAAGCTGTGGCCCACCTGCT
TTGAGAAGAAACTGCTAAAGGAAGCCTTTCAGAAGACCCTCACGGATCTG
AAGCTGGACTATTTGGACCTCTATCTTATTCACTGGCCACAGGGACTTCA
GCCAGGAAAGGAGTTATTCCCAAAGATGACCAAGGCAGAATCCTCACCA
GTAAGCAACATTCTTGGAAGCCTGGGAGGGCATGGAGGAACTGGTGGAC
CAGGGGCTGGTGAAAGCTCTGGGCGTCTCCAACTTCAACCACTTCCAGAT
TGAAAGGCTCCTGAACAAGCCTGGACTAAAACATAAGCCAGTGACCAACC
AGGTTGAGTGTCATCCTTACCTCACCCAGGAAAACTGATCCAGTACTGT
CACTCGAAGGGCATCTCTGTCACTGCCTACAGTCCCTGGGCTCCCCAGA
CAGGCCTAGCGCCAAGCCAGAGGACCCTTCACTATTAGAGGACCCCAAA
TTAAAGAGATTGCCGCCAAGCACAAGAAAACCTCAGCCCAGGTTCTGATT
CGGTTTCACATCCAGAGGAACGTGGTGGTGATCCCGAAGTCTGTGACGCC
ATCACGTATACAGGAGAACATTCAGGTCTTTGATTTCCAGTTGAGTGACG
AGGAGATGGCCACTATCCTTAGCTTCAACAGAAACTGGAGGGCCTGCCTG
CTGCCTGAGACAGTAAACATGGAAGAATATCCCTATGATGCAGAATACTG
A
``` mouse Dlx6 mRNA seq: (SEQ ID NO: 51)
```
gtgaaagaaa cccgggagaa ggctttctcc agcccccaaa
gttttgatga tgaccatgac tacgatggct gacggcttgg
aaggcagga ctcgtccaaa tccgccttca tggagttcgg
gcagcagcaa cagcagcagc agcaacaaca gcagcagcaa
cagcagcagc agcagcagca acagcagccg ccgccgccgc
caccgccgcc gccgccgcag ccgcactcgc
agcagacctc cccggccatg gcaggcgcac attaccctct
gcactgcttg cactcggccg cggcggcggc ggcggcggcc
```

| Sequences |
|---|
| ggctcccacc atcaccacca ccagcaccac caccacggct<br>cgccctacgc gtcgagcgga ggcaactcct acaaccaccg<br>atcgctcgcc gcctaccct acatgagcca ctcgcagcac<br>agcccttacc tccagtccta ccacaacagc agcgcggccg<br>cccagacgcg cggggacgac acagatcaac aaaaaacgac<br>agtgatcgaa aacggggaaa tcaggttcaa cggaaagggg<br>aaaaagattc ggaagcctcg gaccatttat tccagcctgc<br>agctccaggc tttaaaccat cgctttcagc agactcaata<br>cctggccctt cccgagagag ccgaactggc tgcttcctta<br>ggactgacac aaacacaggt gaagatatgg tttcagaata<br>agcgctctaa gtttaagaaa ttgctgaagc agggtagtaa<br>cccacacgag agtgaccccc tcccgggttc agcagccctg<br>tcaccacgat caccagcct gcctccagtg tgggactttt<br>ctgcctctgc caagggcgtc agtatgcctc ccaacagcta<br>catgccgggg tattcacact ggtattcctc accacaccag<br>gacaccatgc agagaccaca gatgatgtga cttctctgag<br>tgaacgccta cggagcttct gaaggagaca ttctccaccg<br>gcagaagaat ctgcacaaac atggcagcat ttttacttgt<br>ttaatgagtt taagacatta catgataaaa aacaaagatt t |
| human Dlx6 mRNA seq: (SEQ ID NO: 52)<br>atgatgacca tgactacgat ggctgacggc ttggaaggcc<br>aggactcgtc caaatccgcc ttcatggagt tcgggcagca<br>gcagcagcag cagcagcaac agcagcagca gcagcagcag<br>caacagcaac agccgccgcc ccgccgccgc ccgccgccgc<br>agccgcactc gcagcagagc tccccggcca tggcaggcgc<br>gcactaccct ctgcactgcc tgcactcggc ggcggcggcg<br>gcagcgggcg gctcgcacca ccaccaccac caccagcacc<br>accaccacgg ctcgcctac gcgtcggggc gagggaactc<br>ctacaaccac cgctcgctcg ccgcctaccc ctacatgagc<br>cactcgcagc acagccctta cctccagtcc taccacaaca<br>gcagcgcagc cgcccagacg cgaggggacg acacagatca<br>acaaaaaact acagtgattg aaaacgggga aatcaggttc<br>aatgggaaag ggaaaaagat tcggaagcct cggaccattt<br>attccagcct gcagctccag gctttaaacc atcgctttca<br>gcagacacag tatctggccc ttccagagag agccgaactg<br>gcagcttcct taggactgac acaaacacag gtgaagatat<br>ggtttcagaa caaacgctct aagtttaaga aactgctgaa<br>gcagggcagt aatcctcatg agagcgaccc cctccaggc<br>tcggcggccc tgtcgccacg ctcgccagcg ctgcctccag<br>tctgggacgt ttctgcctcg gccaaggtg tcagtatgcc<br>ccccaacagc tacatgcctg gctattctca ctggtactcc<br>tctccacacc aggacacgat gcagagacca cagatgatgt<br>gagttgccca agggaacacc ctagggaaac gtctgaacaa<br>ggaaaagagg atccggaacc tgcttgtatc tgcgaaaagg<br>agccaaagga gcaggcttag gagagctcat aagtgtggca<br>agaagccgac taggctcatt ctctctccct ctctctctct<br>ctccctctcc tttctttta cttcttcctt tcctccattc<br>cttcttttct tccttttcct ttctaccttt ctttttcttt<br>tgcctttcac ctttttttctc atttaccttc tctcttgagc<br>aacgtcagta attgatcttg catctcagag agagagaaag<br>agcatgtgtg agagagaaac tggtttctat gccagcactc<br>ctgaaacccc ttactgtaag gatatttct cttacccctt<br>gggatccagg ctctgagtct cttctctttg ggagtatcca<br>tcaaaatgac ttttttaaa aacagatttt cccccaacca<br>gaagaatctg cacaaacttg gcagcgtttt tacttgttta<br>atgagtttaa gacattacat ggtgaaagag aagcattttg<br>gactcctgca ttttatta tcattcccag actgacgaga<br>aaaagaaaat tcctcacata acagcccttc tctaaagaaa<br>aaggaaaaag tggctgtaag attagaacat tgctacaaag<br>ggaatgctgc atgttttatc aaaatgcaat gaccaggaat<br>gatggttgat taaaaaaaa caaaacaaaa accactcttt<br>ccccacccca cccccccaaa ccctgaactg gaatcaggaa<br>agacggagga aacaatcaaa atcaccattc tattgctttg<br>acaccttac taggtgaatt ggtggcattc acaaagctaa<br>tagggacgtt tatatcaaga aacatttctg tatatattgt<br>tgaatttag ttgtacatat acttttgtatg tttttgtctt<br>ctttcatata tggagtaaaa gccacaaaac gctgaaaaaa<br>aaaaaaaaa aa // |
| mouse Evf2 (Dlx6os1) long non-coding RNA<br>(SEQ ID NO: 53)<br>gcttcaaatt ggatggcact gcagctggag gctttgttca<br>gaattgatcc tggggagcta cgaacccaaa gtttcacagt<br>aggaagggg aaaaagaaa agaaaacatt tttcctaatg<br>taacaatgcg aatgctagaa aatgacaaga ctgatcggtt<br>ttaaaccatt ctgaagactg actgagcgtg gaagttgctc |

| Sequences |
|---|
| aacaaaaaag ggaacgggga tattgaacca gagagaaacc<br>tacgcccaga agaacatgtc cctggattgc tttcccactg<br>ctgtggagtg tcttgaacac tggtccctgg acaccaactt<br>caagaagact tcatggatgg ctgtccagtc ttatgagcca<br>cagtttcccc tctactttt cttcactcca gcgaggctct<br>tatcagggtc agatcagaga tgaaccagct ggacgacaga<br>ttggagcgct gacctcttag agtgctaaca gtgaacagtg<br>tggggtcaga tctatagaaa gataataata agaaaacacc<br>ctatatgcaa gggagaggga tggttcataa tttcttaaag<br>attgaaatca aggaacaatc aaaatataga agaatgtgga<br>cgtgttttgc tgcaggactt ctgttrtgtc cccattggaa<br>tatgtattat ggtattcctg ttggatcagg actcagggc<br>aaggctaagc attccagtgg tcctcctact tagctcttgt<br>cctttcgtaa gaaacaccaa ctcattagtc tctatattac<br>ttctctgtac tgtagatctg cattcttgat ctgagagata<br>ttggcaatga cactcttgta tgataaagct caatgataag<br>agtacttcaa accccccttga acttttttgtt tatacatcaa<br>gtggtgacat tgtgtattga gctaattaga tcaatggagt<br>cacagggtga tactgaactc ttttaaaata tttggctgaa<br>acatgacatt gtagttattt gtagaagaga acattatgga<br>atatgaaaaa catcacagaa cacagaacta gcagcagaaa<br>ctagcagcag gtagacattt ttccttttcc atagagcttt<br>caaccaaatg tctctgtaga aaatagtggc tatcgtgtat<br>atatatagcc acatagatgt ccttgagtgt accctgtagt<br>cagtgggaa gttcctactg ccacagtcat ggccatggct<br>1201 atgttctcta agcctacatt ttataaacac tctgtgaatc<br>ttgactactt ttcttagca agcattgcaa agtcctggga<br>tgtcagagaa gtgcctgggg ttggcagggt ttctagagag<br>gaaattgtta atgatttga accagaaaac aaacagggga<br>tggggttcag aaccaacaat taccctatt ctatgtagga<br>aaccacaaca tgaaatatgc tgggcatgga aactttgata<br>ccttggtttt tcattctttt taaaaattaa tactaaagag<br>ctatgcgact gtaggcaagc cattcccat ccctgtgaa<br>tatctcccag atgactttaa atccttcta gttctgaaag<br>gcttttaaca tcagggccca ggctccagtg ccagtttca<br>aaataccctc ccatttgatg ttaggttaca taaacattgt<br>tcttttttttg ggagggtctc atttttcaac atttaaaac<br>acacatcagg ttctctggta ttaaaaagat gccatcctg<br>agtccctac tatctgtgct gcctgccttt cctcctgttc<br>tttccttatt cccatcccta ttgaacttgt gctatgcagt<br>atgcatcagg tatgtgttag ctttggggat acatgataga<br>taaactggac acacagggtc<br>1861 ttcccattct cttctggaat tttctttgga gggagcctct<br>tgtatctaga cagaccgtgc tgtggtaccc cagaggtaac<br>cacctacagg cttcactctg cctaagcaat tttgctgtgc<br>actaagatac acattcaagt aacttttagat taccacaata<br>acttttctcca ggtatgagga aaagagataa tttacttctg<br>agatgtgtat aggatagccc tccatcctgg gaagaacagt<br>2101 gactactcca tgcatcccga ccttgcccag ggaaagctaa<br>tgtttctctg tgttatccct gtgacttgcc acttctttaa<br>aaaggaatgg gcaaacaata aacgacaaa aatgttgtct<br>gacctcattg gaaatccttt taagaattaa tccttctat<br>ctccttcatt atcacaaat ctattgaata cttatctctg<br>agtccagggc atatttata atacataaaa caatggaatt<br>tcaaaattgg agcactgaca tacaatattg gttttgagta<br>tattatttat agggaatgac tttagacatt gcaatttatg<br>acttaactga taaaatggat gactcttgac ttttcaatat<br>cattttcagt tcagtcgagg aatagctttcc tccaggtaat<br>gtctatactt tcctatgact aagggctcta actatctctg<br>ttgcttttct ttatgtaggc atatgttagt attttattac<br>tatatgacaa atgtattaaa gaaagcatga aattaatgag<br>ataaactttt cagataggag tttagaaaat caagggggca<br>agataaaata atgaaaatc aacttaaata attaacatat<br>tccagatata ttggaataaa tgtttattgt acccatttgg<br>ttttgtcttg ggtatttat ttcttatctc actgattttt<br>tatcttttcc tattagcttt tattgtcttt tttgatttt<br>gttgttgcgt ttctccattt tatttttctt gttgatgttg<br>tttgtttgtt tgtttgtttg<br>2881 tatagaga aagaacagaa ggttggttgg atagggaggt<br>ggggaagatc tatctggatg gagttgggag gagggaaaat<br>acacgatcga aatatttat gtgatgggca gggcatagtg<br>gtacatgtct ttaatctcag cactcgtagg gcagaggcag<br>gtggatctct atgactggga ggctagcctg atatacaaag<br>tgagaccaga acataggct gcctcaaaaa ctttatatat<br>atattaaaaa tgtttgcttt ttgagacagt cacagataac<br>caaaactgat cttgtaatga tgtaaacatg tccagctaat<br>tttcaaatat tgtagggcag cattctctcc ttttgtgcaca |

```
                    Sequences
cgtggagtca gcaaatccat ataattctaa ccattctggt
gaaaaggaga acactcggcc aagcatctca cacttccaag
tgtgaagcct tgtttgaaag ctccgagtat ctaaatagta
gccctgtgaa aggtaaattt atgaatggtc tggtgtgttc
ttattccagc cattgaccttt aaagcaactt atatatgttt
tctttatcct tcaagagaaa agaaaaatca tatttttcca
agcaattaaa attcttctgc ttcaggtagg aagaaggaat
taggagttat gtctccttgt atataattgc aagtttcatt
tttcttgttt taatgattga cagaaaactg ataaactgag
acatctcctt attagggttg aatgtactct cttggtggcc
ccattgctaa tttgtttgac tattttccat gatttcttac
tctgtaatgg aaaggtttat taaatatgag ggttgcaaag
ctttctgaat actaatgaac ttatttgcca aaatttaaat
gttcttcttg tcagtgaatg cctgtctcac ttaacaggca
ccaaattgaa taatgaagaa aattagactc tatcgtaccc
tcaagagaaa tcgcgtgtga attgtaatag aaaattgagg
gagaaaaggg tcatattgta gcaataacac tagataattt
ggatttttat aaaaaaggat gaacttaggg aagctcaggt
catttcaaag aaacacacat ttggttaatt catgcaaaac
gctggtttcc cctcaaccca ggtggtctat acctatcgcc
agtttacaga aaaaggaagc caggtggatg gaaaacgtgt
gccaagtttc tgtgcttaca atccactaaa ctcattctca
tatgaggact ttatatacct gtgatggagt gggaaaatca
ataacctgga aaaaatgagt accattttcc aaagaagttc
aataaagaga tggaatttgg gaaactgctg cagttcttcc
tataagc // human Evf2 (Dlx6 AS1) long non-coding RNA
(SEQ ID NO: 54)
atttcacacc tggatgtgct cactcaacca agaatataga
gaaagagctt ctgccctgag actcagaaaa atattctcct
gtgctttggt tcagtataga tttctaaacc ctgatcattg
cttaagagat attcactgag gacagagtct tgctctattg
cccaggctgc aactggtgtg atctcggctc actacaacct
ctgcctcctg ggtcaagcg attctcctgc ctcaagctcc
caagtagctg ggattacaag catgcaccac catgcctggc
taattttttgt attttttagtg gagacggggt ttcgccacat
tggccagggt ggtcttgaac tcctgacctc aagtgatcca
cctgccttgg cctcccaaag tgctgggatt ataagcatga
gccactgcac ccagccttat actgaacttt caatgggttc
aattccacta ggagcataaa ggccactgca tatgagttgt
ggaaagaaga gattagaaga aggaagaact tgagatgagt
tcctccctttc aacattctgt ctcctcctac ctagcatctt
cttttcatta gtctttctag aatgtccatc tgattttggc
cattgcggag agagaagctg agcttttaaag gagtagagac
ttcaaaggcg taggagcttc aaaattcttg tttcttcatg
tttgatcacc cttctaaacc tgtcttctgt tccttctgct
attattttttt cttagagcat aggaaaggggg agcttttaaa
ttaatactta aagcatggaa aaaaagaact tgagaagaaa
gtaaaacaag ggagatgagg ctagtaaagt aaggaaaatg
aagaggaaga ggaggaaggg ttagcttcta aattccaagt
caaattgata tggaacaggc aagccgcttg tcttacttaa
acttcagaaa aggatctgct gaaacttgat agaaatggaa
agggaaatcc ttggggtggg gaacctccaa acattagtaa
tgatattgaa caactcaaag tattgaggaa atctgcaggc
tacatgcctg aagattaccc atgcagatag accaaaagga
ttagaattat ctgttgatat tagtaatatt tattgacatc
tagctagtat tggtaatttt aagatttttga ttaatttcctt
tggtaatagc tatgatatat tttatagaca agaattatat
ctataggctt gctatcatag gctcatttaa tcagcattaa
tttagtctac tgatattttg cacatttgaa tcattcactt
atgctaggta actcattgca aaataaaaag atgattcctg
tatgtatggc agctatacat taaggaggag tctaccagaa
tatgaaaaag tcagctgacc taaatattgc tgagacaaag
gaaaacccac tcccttggag gagcatgacc ttttcctgta
attcttccca ctgctgttgt tgagctcctt ggatcctggc
tcctggacac catcatcaag aagactttat ggatgggctg
tccacccact gagagaagag gagcatcagc tacagtttct
ctctagattg ccttcttcat tttgagtaat gactgtcagc
agggtcagat taaacacaaa acaactggac aattgcttgg
aggactaaac tataagggca ctaacatgtc aatagtaggc
taacacatcc atggaaaata tatttaccag ctcttctctc
agggaggatt ctgtgtgggg ttggaagtaa tgatttgtta
aattccttag gggtagaaag tagggcataa tcagaatata
gaggaatatg ctgtttgact tcagggtttc tgttttttctt
actaggatat ataaaacagg gactctagct agattgttta
```
```
tgaccacaga gggtaggctg agtgctccca tgatcttcct
gcttggttct tgcccataca gaggtcagcc tttcctctaa
taaagattga acaagtagtg gtctgaggga //
```

This Example demonstrates the novel pathway to directly increase the level of serotonin receptor gene expression in neurons, providing a novel agent for treating neurological disorders and stress-induced conditions. Applicant has found that Evf2 long non-coding RNA modulates serotonin receptor expression by decreasing the expression of a specific enzyme, Akr1b8, in developing interneurons. Mice lacking Evf2 exhibit changes in behavior, including behavioral despair, learning and seizure susceptibility. Compositions and methods of treating neurological disorders and stress-induced conditions are contemplated by treating a subject with Akr1b8/B10 or an agonist thereof. Methods and compositions for treating neurological disorders and stress-induced conditions by treating a subject with small molecule effectors or metabolites of the mevalonate pathway are also contemplated.

For example, a method of treating a neurological disorder or stress-induced condition in a subject, the method comprising the steps of: administering an effective amount of at least one aldo-keto reductase family 1, member b10 (Akr1b10), aldo-keto reductase family 1, member B8 (Akr1b8), an agonist of Akr1b10, or an agonist of Akr1b8 in order to alleviate, reduce or inhibit one or more symptoms of the neurological disorder or stress induced condition in the subject.

Each publication, patent, and patent publication cited in this disclosure is incorporated in reference herein in its entirety. The present invention is not intended to be limited to the foregoing examples, but encompasses all such modifications and variations as come within the scope of the appended claims.

REFERENCES

Anderson, E., Devenney, P. S., Hill, R. E., and Lettice, L. A. (2014). Mapping the Shh long-range regulatory domain. Development 141, 3934-3943.

Anderson, S. A., Eisenstat, D. D., Shi, L., and Rubenstein, J. L. (1997). Interneuron migration from basal forebrain to neocortex: dependence on Dlx genes. Science 278, 474-476.

Andrey, G., Montavon, T., Mascrez, B., Gonzalez, F., Noordermeer, D., Leleu, M., Trono, D., Spitz, F., and Duboule, D. (2013). A switch between topological domains underlies HoxD genes collinearity in mouse limbs. Science 340, 1234167.

Berghoff, E. G., Clark, M. F., Chen, S., Cajigas, I., Leib, D. E., and Kohtz, J. D. (2013). Evf2 (Dlx6as) lncRNA regulates ultraconserved enhancer methylation and the differential transcriptional control of adjacent genes. Development 140, 4407-4416.

Bond, A. M., Vangompel, M. J., Sametsky, E. A., Clark, M. F., Savage, J. C., Disterhoft, J. F., and Kohtz, J. D. (2009). Balanced gene regulation by an embryonic brain ncRNA is critical for adult hippocampal GABA circuitry. Nat Neurosci 12, 1020-1027.

Brockdorff, N. (2011). Chromosome silencing mechanisms in X-chromosome inactivation: unknown unknowns. Development 138, 5057-5065.

Cajigas, I., Leib, D. E., Cochrane, J., Luo, H., Swyter, K. R., Chen, S., Clark, B. S., Thompson, J., Yates, J. R., Kingston, R. E., et al. (2015). Evf2 lncRNA/BRG1/DLX1 interactions reveal RNA-dependent inhibition of chromatin remodeling. Development 142, 2641-2652.

Cho, K. K., Hoch, R., Lee, A. T., Patel, T., Rubenstein, J. L., and Sohal, V. S. (2015). Gamma rhythms link prefrontal interneuron dysfunction with cognitive inflexibility in Dlx5/6(+/−) mice. Neuron 85, 1332-1343.

Cobos, I., Calcagnotto, M. E., Vilaythong, A. J., Thwin, M. T., Noebels, J. L., Baraban, S. C., and Rubenstein, J. L. (2005). Mice lacking Dlx1 show subtype-specific loss of interneurons, reduced inhibition and epilepsy. Nature neuroscience 8, 1059-1068. de Laat, W., and Duboule, D. (2013). Topology of mammalian developmental enhancers and their regulatory landscapes. Nature 502, 499-506.

De Marco Garcia, N. V., Karayannis, T., and Fishell, G. (2011). Neuronal activity is required for the development of specific cortical interneuron subtypes. Nature 472, 351-355.

DeFelipe, J., Lopez-Cruz, P. L., Benavides-Piccione, R., Bielza, C., Larranaga, P., Anderson, S., Burkhalter, A., Cauli, B., Fairen, A., Feldmeyer, D., et al. (2013). New insights into the classification and nomenclature of cortical GABAergic interneurons. Nature reviews Neuroscience 14, 202-216.

Dekker, J. (2016). Mapping the 3D genome: Aiming for consilience. Nat Rev Mol Cell Biol 17, 741-742.

Endo, S., Matsunaga, T., Ohta, C., Soda, M., Kanamori, A., Kitade, Y., Ohno, S., Tajima, K., El-Kabbani, O., and Hara, A. (2011). Roles of rat and human aldo-keto reductases in metabolism of farnesol and geranylgeraniol. Chem Biol Interact 191, 261-268.

Feng, J., Bi, C., Clark, B. S., Mady, R., Shah, P., and Kohtz, J. D. (2006). The Evf-2 noncoding RNA is transcribed from the Dlx-5/6 ultraconserved region and functions as a Dlx-2 transcriptional coactivator. Genes Dev 20, 1470-1484.

Gallego, O., Ruiz, F. X., Ardevol, A., Dominguez, M., Alvarez, R., de Lera, A. R., Rovira, C., Farres, J., Fita, I., and Pares, X. (2007). Structural basis for the high all-trans-retinaldehyde reductase activity of the tumor marker AKR1B10. Proceedings of the National Academy of Sciences of the United States of America 104, 20764-20769.

Gelman, D. M., and Marin, O. (2010). Generation of interneuron diversity in the mouse cerebral cortex. The European journal of neuroscience 31, 2136-2141.

Giorgetti, L., Lajoie, B. R., Carter, A. C., Attia, M., Zhan, Y., Xu, J., Chen, C. J., Kaplan, N., Chang, H. Y., Heard, E., et al. (2016). Structural organization of the inactive X chromosome in the mouse. Nature 535, 575-579.

Hug, C. B., Grimaldi, A. G., Kruse, K., and Vaquerizas, J. M. (2017). Chromatin Architecture Emerges during Zygotic Genome Activation Independent of Transcription. Cell 169, 216-228 e219.

Kmita, M., and Duboule, D. (2003). Organizing axes in time and space; 25 years of colinear tinkering. Science 301, 331-333.

Kohtz, J. D., Baker, D. P., Corte, G., and Fishell, G. (1998). Regionalization within the mammalian telencephalon is mediated by changes in responsiveness to Sonic Hedgehog. Development 125, 5079-5089.

Lee, S., Kruglikov, I., Huang, Z. J., Fishell, G., and Rudy, B. (2013). A disinhibitory circuit mediates motor integration in the somatosensory cortex. Nature neuroscience 16, 1662-1670.

Lettice, L. A., Heaney, S. J., Purdie, L. A., Li, L., de Beer, P., Oostra, B. A., Goode, D., Elgar, G., Hill, R. E., and de Graaff, E. (2003). A long-range Shh enhancer regulates expression in the developing limb and fin and is associated with preaxial polydactyly. Hum Mol Genet 12, 1725-1735.

Letzkus, J. J., Wolff, S. B., Meyer, E. M., Tovote, P., Courtin, J., Herry, C., and Luthi, A. (2011). A disinhibitory microcircuit for associative fear learning in the auditory cortex. Nature 480, 331-335.

Liu, S. J., Nowakowski, T. J., Pollen, A. A., Lui, J. H., Horlbeck, M. A., Attenello, F. J., He, D., Weissman, J. S., Kriegstein, A. R., Diaz, A. A., et al. (2016). Single-cell analysis of long non-coding RNAs in the developing human neocortex. Genome biology 17, 67.

Long, J. E., Garel, S., Alvarez-Dolado, M., Yoshikawa, K., Osumi, N., Alvarez-Buylla, A., and Rubenstein, J. L. (2007). Dlx-dependent and -independent regulation of olfactory bulb interneuron differentiation. The Journal of neuroscience: the official journal of the Society for Neuroscience 27, 3230-3243.

Merlo, G. R., Paleari, L., Mantero, S., Genova, F., Beverdam, A., Palmisano, G. L., Barbieri, O., and Levi, G. (2002). Mouse model of split hand/foot malformation type I. Genesis 33, 97-101.

Nagano, T., Lubling, Y., Varnai, C., Dudley, C., Leung, W., Baran, Y., Mendelson Cohen, N., Wingett, S., Fraser, P., and Tanay, A. (2017). Cell-cycle dynamics of chromosomal organization at single-cell resolution. Nature 547, 61-67.

Nery, S., Fishell, G., and Corbin, J. G. (2002). The caudal ganglionic eminence is a source of distinct cortical and subcortical cell populations. Nature neuroscience 5, 1279-1287.

Noordermeer, D., Leleu, M., Splinter, E., Rougemont, J., De Laat, W., and Duboule, D. (2011). The dynamic architecture of Hox gene clusters. Science 334, 222-225.

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385.

Penning, T. M. (2015). The aldo-keto reductases (AKRs): Overview. Chemico-biological interactions 234, 236-246.

Phillips-Cremins, J. E., Sauna, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295.

Pi, H. J., Hangya, B., Kvitsiani, D., Sanders, J. I., Huang, Z. J., and Kepecs, A. (2013). Cortical interneurons that specialize in disinhibitory control. Nature 503, 521-524.

Price, M., Lemaistre, M., Pischetola, M., Di Lauro, R., and Duboule, D. (1991). A mouse gene related to Distal-less shows a restricted expression in the developing forebrain. Nature 351, 748-751.

Redrup, L., Branco, M. R., Perdeaux, E. R., Krueger, C., Lewis, A., Santos, F., Nagano, T., Cobb, B. S., Fraser, P., and Reik, W. (2009). The long noncoding RNA Kcnq1ot1 organises a lineage-specific nuclear domain for epigenetic gene silencing. Development 136, 525-530.

Rudy, B., Fishell, G., Lee, S., and Hjerling-Leffler, J. (2011). Three groups of interneurons account for nearly 100% of neocortical GABAergic neurons. Developmental neurobiology 71, 45-61.

Sanyal, A., Lajoie, B. R., Jain, G., and Dekker, J. (2012). The long-range interaction landscape of gene promoters. Nature 489, 109-113.

Stevens, T. J., Lando, D., Basu, S., Atkinson, L. P., Cao, Y., Lee, S. F., Leeb, M., Wohlfahrt, K. J., Boucher, W., O'Shaughnessy-Kirwan, A., et al. (2017). 3D structures of individual mammalian genomes studied by single-cell Hi-C. Nature 544, 59-64.

van de Werken, H. J., de Vree, P. J., Splinter, E., Holwerda, S. J., Klous, P., de Wit, E., and de Laat, W. (2012). 4C technology: protocols and data analysis. Methods Enzymol 513, 89-112.

Waclaw, R. R., Ehrman, L. A., Pierani, A., and Campbell, K. (2010). Developmental origin of the neuronal subtypes that comprise the amygdalar fear circuit in the mouse. The Journal of neuroscience: the official journal of the Society for Neuroscience 30, 6944-6953.

Wang, Y., Dye, C. A., Sohal, V., Long, J. E., Estrada, R. C., Rortocil, T., Lufkin, T., Deisseroth, K., Baraban, S. C., and Rubenstein, J. L. (2010). Dlx5 and Dlx6 regulate the development of parvalbumin-expressing cortical interneurons. J Neurosci 30, 5334-5345.

Wichterle, H., Turnbull, D. H., Nery, S., Fishell, G., and Alvarez-Buylla, A. (2001). In utero fate mapping reveals distinct migratory pathways and fates of neurons born in the mammalian basal forebrain. Development 128, 3759-3771.

Williamson, I., Lettice, L. A., Hill, R. E., and Bickmore, W. A. (2016). Shh and ZRS enhancer colocalisation is specific to the zone of polarising activity. Development 143, 2994-3001.

Won, H., de la Torre-Ubieta, L., Stein, J. L., Parikshak, N. N., Huang, J., Opland, C. K., Gandal, M. J., Sutton, G. J., Hormozdiari, F., Lu, D., et al. (2016). Chromosome conformation elucidates regulatory relationships in developing human brain. Nature 538, 523-527.

Xu, Q., Guo, L., Moore, H., Waclaw, R. R., Campbell, K., and Anderson, S. A. (2010). Sonic hedgehog signaling confers ventral telencephalic progenitors with distinct cortical interneuron fates. Neuron 65, 328-340.

Zerucha, T., Stuhmer, T., Hatch, G., Park, B. K., Long, Q., Yu, G., Gambarotta, A., Schultz, J. R., Rubenstein, J. L., and Ekker, M. (2000). A highly conserved enhancer in the Dlx5/Dlx6 intergenic region is the site of cross-regulatory interactions between Dlx genes in the embryonic forebrain. The Journal of neuroscience: the official journal of the Society for Neuroscience 20, 709-721.

Berghoff E G, Clark M F, Chen S, Cajigas I, Leib D E, Kohtz J D. 2013. Evf2 (Dlx6as) lncRNA regulates ultraconserved enhancer methylation and the differential transcriptional control of adjacent genes. *Development* 140: 4407-4416.

Bond A M, Vangompel M J, Sametsky E A, Clark M F, Savage J C, Disterhoft J F, Kohtz J D. 2009. Balanced gene regulation by an embryonic brain ncRNA is critical for adult hippocampal GABA circuitry. *Nat Neurosci* 12: 1020-1027.

Brind'Amour J, Liu S, Hudson M, Chen C, Karimi M M, Lorincz M C. 2015. An ultra-low-input native ChIP-seq protocol for genome-wide profiling of rare cell populations. *Nature communications* 6: 6033.

Cajigas I, Leib D E, Cochrane J, Luo H, Swyter K R, Chen S, Clark B S, Thompson J, Yates J R, Kingston R E et al. 2015. Evf2 lncRNA/BRG1/DLX1 interactions reveal RNA-dependent inhibition of chromatin remodeling. *Development* 142: 2641-2652.

Feng J, Bi C, Clark B S, Mady R, Shah P, Kohtz J D. 2006. The Evf-2 noncoding RNA is transcribed from the Dlx-5/6 ultraconserved region and functions as a Dlx-2 transcriptional coactivator. *Genes Dev* 20: 1470-1484.

Feng J, Liu T, Zhang Y. 2011. Using MACS to identify peaks from ChIP-Seq data. *Current protocols in bioinformatics/editoral board, Andreas D Baxevanis [et al]* Chapter 2: Unit 2 14.

Flandin P, Zhao Y, Vogt D, Jeong J, Long J, Potter G, Westphal H, Rubenstein J L. 2011. Lhx6 and Lhx8 coordinately induce neuronal expression of Shh that controls the generation of interneuron progenitors. *Neuron* 70: 939-950.

Gelman D M, Marin O. 2010. Generation of interneuron diversity in the mouse cerebral cortex. *The European journal of neuroscience* 31: 2136-2141.

Gene Ontology C. 2015. Gene Ontology Consortium: going forward. *Nucleic Acids Res* 43: D1049-1056.

Kent W J, Sugnet C W, Furey T S, Roskin K M, Pringle T H, Zahler A M, Haussler D. 2002. The human genome browser at UCSC. *Genome Res* 12: 996-1006.

Kharchenko P V, Tolstorukov M Y, Park P J. 2008. Design and analysis of ChIP-seq experiments for DNA-binding proteins. *Nature biotechnology* 26: 1351-1359.

Krzywinski M, Schein J, Birol I, Connors J, Gascoyne R, Horsman D, Jones S J, Marra M A. 2009. Circos: an information aesthetic for comparative genomics. *Genome Res* 19: 1639-1645.

Landt S G, Marinov G K, Kundaje A, Kheradpour P, Pauli F, Batzoglou S, Bernstein B E, Bickel P, Brown J B, Cayting P et al. 2012. ChIP-seq guidelines and practices of the ENCODE and modENCODE consortia. *Genome research* 22: 1813-1831.

Langmead B, Salzberg S L. 2012. Fast gapped-read alignment with Bowtie 2. *Nat Methods* 9: 357-359.

Li H, Durbin R. 2009. Fast and accurate short read alignment with Burrows-Wheeler transform. *Bioinformatics* 25: 1754-1760.

Liu P, Jenkins N A, Copeland N G. 2003. A highly efficient recombineering-based method for generating conditional knockout mutations. *Genome research* 13: 476-484.

Love M I, Huber W, Anders S. 2014. Moderated estimation of fold change and dispersion for RNA-seq data with DESeq2. *Genome Biol* 15: 550.

Marinov G K, Kundaje A, Park P J, Wold B J. 2014. Large-scale quality analysis of published ChIP-seq data. G3 4: 209-223.

Merlo G R, Paleari L, Mantero S, Genova F, Beverdam A, Palmisano G L, Barbieri O, Levi G. 2002. Mouse model of split hand/foot malformation type I. *Genesis* 33: 97-101.

Quinlan A R, Hall I M. 2010. BEDTools: a flexible suite of utilities for comparing genomic features. *Bioinformatics* 26: 841-842.

Soriano P. 1999. Generalized lacZ expression with the ROSA26 Cre reporter strain. *Nature genetics* 21: 70-71.

van de Werken H J, de Vree P J, Splinter E, Holwerda S J, Klous P, de Wit E, de Laat W. 2012. 4C technology: protocols and data analysis. *Methods Enzymol* 513: 89-112.

Wand M P. 1994. Fast Computation of Multivariate Kernel Estimators. *Journal of Computational and Graphical Statistics* 3: 433-445.

Westra J W, Peterson S E, Yung Y C, Mutoh T, Banal S, Chun J. 2008. Aneuploid mosaicism in the developing and adult cerebellar cortex. *J Comp Neurol* 507: 1944-1951.

Won H, de la Torre-Ubieta L, Stein J L, Parikshak N N, Huang J, Opland C K, Gandal M J, Sutton G J, Hormozdiari F, Lu D et al. 2016. Chromosome conformation elucidates regulatory relationships in developing human brain. *Nature* 538: 523-527.

Zhou X, Maricque B, Xie M, Li D, Sundaram V, Martin E A, Koebbe B C, Nielsen C, Hirst M, Farnham P et al. 2011. The Human Epigenome Browser at Washington University. *Nat Methods* 8: 989-990.

---

The invention claimed is:

1. A method of increasing expression of 5-hydroxytryptamine receptor 3A (5Htr3a) in at least one interneuron in a subject having a developmental neurological disorder or mood disorder treated with serotonin regulation, the method comprising:
contacting the at least one interneuron with an effective amount of at least one of aldo-keto reductase family 1, member B8 (Akr1B8), an expression vector encoding Akr1B8, aldo-keto reductase family 1, member B10 (Akr1B10), or an expression vector encoding Akr1B10, wherein the at least one interneuron exhibits an increase expression of 5Htr3a.

2. The method of claim 1, wherein the increased expression of 5Htr3a increases the level of serotonin signaling by the interneuron.

3. The method of claim 1, wherein the interneuron is a human neuron.

4. The method of claim 1, wherein the interneuron is contacted in vivo.

5. The method according to claim 4, wherein the interneuron is within a patient having a developmental neurological disorder or stress-induced condition.

6. The method of claim 4, wherein the interneuron is within a patient having a mood disorder.

* * * * *

SEQUENCE LISTING

```
<160> NUMBER OF SEQ ID NOS: 60

<210> SEQ ID NO 1
<211> LENGTH: 316
<212> TYPE: PRT
<213> ORGANISM: Homo sapiens

<400> SEQUENCE: 1

Met Ala Thr Phe Val Glu Leu Ser Thr Lys Ala Lys Met Pro Ile Val
1               5                   10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
        35                  40                  45

Tyr Gln Asn Glu His Glu Val Gly Glu Ala Ile Gln Glu Lys Ile Gln
    50                  55                  60

Glu Lys Ala Val Lys Arg Glu Asp Leu Phe Ile Val Ser Lys Leu Trp
65                  70                  75                  80

Pro Thr Phe Phe Glu Arg Pro Leu Val Arg Lys Ala Phe Glu Lys Thr
                85                  90                  95

Leu Lys Asp Leu Lys Leu Ser Tyr Leu Asp Val Tyr Leu Ile His Trp
            100                 105                 110

Pro Gln Gly Phe Lys Ser Gly Asp Asp Leu Phe Pro Lys Asp Asp Lys
        115                 120                 125

Gly Asn Ala Ile Gly Gly Lys Ala Thr Phe Leu Asp Ala Trp Glu Ala
    130                 135                 140

Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
                165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
        195                 200                 205

Ala Tyr Ser Pro Leu Gly Ser Pro Asp Arg Pro Trp Ala Lys Pro Glu
    210                 215                 220

Asp Pro Ser Leu Leu Glu Asp Pro Lys Ile Lys Glu Ile Ala Ala Lys
225                 230                 235                 240

His Lys Lys Thr Ala Ala Gln Val Leu Ile Arg Phe His Ile Gln Arg
                245                 250                 255

Asn Val Ile Val Ile Pro Lys Ser Val Thr Pro Ala Arg Ile Val Glu
            260                 265                 270

Asn Ile Gln Val Phe Asp Phe Lys Leu Ser Asp Glu Met Ala Thr
        275                 280                 285

Ile Leu Ser Phe Asn Arg Asn Trp Arg Ala Cys Asn Val Leu Gln Ser
    290                 295                 300

Ser His Leu Glu Asp Tyr Pro Phe Asp Ala Glu Tyr
```

```
305                 310                 315
```

<210> SEQ ID NO 2
<211> LENGTH: 948
<212> TYPE: DNA
<213> ORGANISM: Homo sapiens

<400> SEQUENCE: 2

```
atggccacgt tgtgtggagct cagtaccaaa gccaagatgc ccattgtggg cctgggcact    60
tggaagtctc ctcttggcaa agtgaaagaa gcagtgaagg tggccattga tgcaggatat   120
cggcacattg actgtgccta tgtctatcag aatgaacatg aagtggggga agccatccaa   180
gagaagatcc aagagaaggc tgtgaagcgg gaggacctgt tcatcgtcag caagttgtgg   240
cccactttct tgagagacc ccttgtgagg aaagcctttg agaagaccct caaggacctg   300
aagctgagct atctggacgt ctatcttatt cactggccac agggattcaa gtctggggat   360 gacctttttcc ccaaagatga taaaggtaat gccatcggtg aaaagcaac gttcttggat   420 gcctgggagg ccatggagga ctggtggat gaggggctgg tgaaagccct tggggtctcc   480
aatttcagcc acttccagat cgagaagctc ttgaacaaac ctggactgaa atataaacca   540
gtgactaacc aggttgagtg tcacccatac ctcacacagg agaaactgat ccagtactgc   600
cactccaagg gcatcaccgt tacggcctac agcccctgg gctctccgga tagaccttgg   660
gccaagccag aagacccttc cctgctggag gatcccaaga ttaaggagat tgctgcaaag   720
cacaaaaaaa ccgcagccca ggttctgatc cgtttccata tccagaggaa tgtgattgtc   780
atccccaagt ctgtgacacc agcacgcatt gttgagaaca ttcaggtctt tgactttaaa   840
ttgagtgatg aggagatggc aaccatactc agcttcaaca gaaactggag ggcctgtaac   900
gtgttgcaat cctctcattt ggaagactat cccttcgatg cagaatat               948
```

<210> SEQ ID NO 3
<211> LENGTH: 316
<212> TYPE: PRT
<213> ORGANISM: Mus musculus

<400> SEQUENCE: 3

```
Met Ala Thr Phe Val Glu Leu Ser Thr Lys Ala Lys Met Pro Ile Val
1               5                   10                  15

Gly Leu Gly Thr Trp Lys Ser Pro Pro Asn Gln Val Lys Glu Ala Val
            20                  25                  30

Lys Ala Ala Ile Asp Ala Gly Tyr Arg His Ile Asp Cys Ala Tyr Ala
        35                  40                  45

Tyr Cys Asn Glu Asn Glu Val Gly Glu Ala Ile Gln Glu Lys Ile Lys
    50                  55                  60

Glu Lys Ala Val Gln Arg Glu Asp Leu Phe Ile Val Ser Lys Leu Trp
65                  70                  75                  80

Pro Thr Cys Phe Glu Lys Lys Leu Leu Lys Glu Ala Phe Gln Lys Thr
                85                  90                  95

Leu Thr Asp Leu Lys Leu Asp Tyr Leu Asp Leu Tyr Leu Ile His Trp
            100                 105                 110

Pro Gln Gly Leu Gln Pro Gly Lys Glu Leu Phe Pro Lys Asp Asp Gln
        115                 120                 125

Gly Arg Ile Leu Thr Ser Lys Thr Thr Phe Leu Glu Ala Trp Glu Gly
    130                 135                 140

Met Glu Glu Leu Val Asp Gln Gly Leu Val Lys Ala Leu Gly Val Ser
145                 150                 155                 160
```

```
Asn Phe Asn His Phe Gln Ile Glu Arg Leu Leu Asn Lys Pro Gly Leu
                165                 170                 175
Lys His Lys Pro Val Thr Asn Gln Val Glu Cys His Pro Tyr Leu Thr
            180                 185                 190
Gln Glu Lys Leu Ile Gln Tyr Cys His Ser Lys Gly Ile Ser Val Thr
        195                 200                 205
Ala Tyr Ser Pro Leu Gly Ser Pro Asp Arg Pro Ser Ala Lys Pro Glu
    210                 215                 220
Asp Pro Ser Leu Leu Glu Asp Pro Lys Ile Lys Glu Ile Ala Ala Lys
225                 230                 235                 240
His Glu Lys Thr Ser Ala Gln Val Leu Ile Arg Phe His Ile Gln Arg
                245                 250                 255
Asn Val Val Ile Pro Lys Ser Val Thr Pro Ser Arg Ile Gln Glu
                260                 265                 270
Asn Ile Gln Val Phe Asp Phe Gln Leu Ser Asp Glu Glu Met Ala Thr
            275                 280                 285
Ile Leu Ser Phe Asn Arg Asn Trp Arg Ala Cys Leu Leu Pro Glu Thr
        290                 295                 300
Val Asn Met Glu Glu Tyr Pro Tyr Asp Ala Glu Tyr
305                 310                 315

<210> SEQ ID NO 4
<211> LENGTH: 951
<212> TYPE: DNA
<213> ORGANISM: Mus musculus

<400> SEQUENCE: 4
atggccacgt tcgtggaact cagtaccaaa gccaagatgc ccattgtggg cctgggcacc      60
tggaagtctc ccccaaacca gtcaaagaa gctgtgaagg cggccattga cgctgggtat     120
cgccatatcg actgcgcgta tgcctattgc aacgagaatg aggtgggaga agccatccaa     180
gagaagatca agagaaggc tgtgcagcgg gaggacctct tcattgtcag caagctgtgg     240
cccacctgct ttgagaagaa actgctaaag gaagccttc agaagaccct cacggatctg     300
aagctggact atttggacct ctatcttatt cactggccac agggacttca gccaggaaag     360
gagttattcc ccaaagatga ccaaggcaga atcctcacca gtaagacaac attcttggaa     420
gcctgggagg catggagga actggtggac caggggctgg tgaaagctct gggcgtctcc     480
aacttcaacc acttccagat tgaaaggctc ctgaacaagc ctggactaaa acataagcca     540
gtgaccaacc aggttgagtg tcatccttac ctcacccagg aaaaactgat ccagtactgt     600
cactcgaagg gcatctctgt cactgcctac agtcccctgg gctccccaga caggcctagc     660
gccaagccag aggacccttc actattagag daccccaaaa ttaaagagat tgccgccaag     720
cacaagaaaa cctcagccca ggttctgatt cggtttcaca tccagaggaa cgtggtggtg     780
atcccgaagt ctgtgacgcc atcacgtata caggagaaca ttcaggtctt tgatttccag     840
ttgagtgacg aggagatggc cactatcctt agcttcaaca gaaactggag ggcctgcctg     900
ctgcctgaga cagtaaacat ggaagaatat ccctatgatg cagaatactg a              951

<210> SEQ ID NO 5
<211> LENGTH: 21
<212> TYPE: DNA
<213> ORGANISM: Artificial Sequence
<220> FEATURE:
<223> OTHER INFORMATION: synthetic
```

```
<400> SEQUENCE: 5
agaggaaugu gauugucaut t                                      21

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
augacaauca cauuccucug g                                      21

<210> SEQ ID NO 7
<211> LENGTH: 27
<212> TYPE: DNA
<213> ORGANISM: Artificial Sequence
<220> FEATURE:
<223> OTHER INFORMATION: synthetic

<400> SEQUENCE: 7
agagctatgc gactgtaggc aagccat                                27

<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
gcatggaaac tttgatacct tggt                                   24

<210> SEQ ID NO 9
<211> LENGTH: 27
<212> TYPE: DNA
<213> ORGANISM: Artificial Sequence
<220> FEATURE:
<223> OTHER INFORMATION: synthetic

<400> SEQUENCE: 9
gcctttcaga actagaaggg atttaaa                                27

<210> SEQ ID NO 10
<211> LENGTH: 24
<212> TYPE: DNA
<213> ORGANISM: Artificial Sequence
<220> FEATURE:
<223> OTHER INFORMATION: synthetic

<400> SEQUENCE: 10
ctccctccgc tcagtataga tttc                                   24

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
cctccccggt gaatatctct t                                      21

<210> SEQ ID NO 12
<211> LENGTH: 21
```

```
<212> TYPE: DNA
<213> ORGANISM: Artificial Sequence
<220> FEATURE:
<223> OTHER INFORMATION: synthetic

<400> SEQUENCE: 12
cacaggcacc cttgagtaag t                                              21

<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
cccccagtct tgggctactg                                                20

<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
ctcagcactg tccaacctgt a                                              21

<210> SEQ ID NO 15
<211> LENGTH: 22
<212> TYPE: DNA
<213> ORGANISM: Artificial Sequence
<220> FEATURE:
<223> OTHER INFORMATION: synthetic

<400> SEQUENCE: 15
tgatgtggag gaggtacaca ag                                             22

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
gtttgacagc tgatggcacc                                                20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
cacactggag aacggaccat                                                20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
```
cctgcctgac atcctgctat                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
ggagatgtcc gttcgcttct                                              20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
cgtccgggtc tctccgtcgc                                              20

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
gccgttcacc tgtgtccaac tggc                                         24

<210> SEQ ID NO 22
<211> LENGTH: 19
<212> TYPE: DNA
<213> ORGANISM: Artificial Sequence
<220> FEATURE:
<223> OTHER INFORMATION: synthetic

<400> SEQUENCE: 22
gcgagcacag cttctttgc                                               19

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
tcgtcatcca tggcgaact                                               19

<210> SEQ ID NO 24
<211> LENGTH: 28
<212> TYPE: DNA
<213> ORGANISM: Artificial Sequence
<220> FEATURE:
<223> OTHER INFORMATION: synthetic

<400> SEQUENCE: 24
gaattatagg aaaacacaat caaacagg                                     28

<210> SEQ ID NO 25
<211> LENGTH: 24
<212> TYPE: DNA
<213> ORGANISM: Artificial Sequence

```
<220> FEATURE:
<223> OTHER INFORMATION: synthetic

<400> SEQUENCE: 25
caggaggaat tcttttctg attg                                                    24

<210> SEQ ID NO 26
<211> LENGTH: 476
<212> TYPE: DNA
<213> ORGANISM: Artificial Sequence
<220> FEATURE:
<223> OTHER INFORMATION: synthetic

<400> SEQUENCE: 26
gaattatagg aaaacacaat caaacaggtg aagaaaagga acaaaaccat ccaggatcta     60
aaaatggaac tagaaacaat aaagaaataa caaagcaaga caaccctgga gttagaaaac    120
ctaggaaaga agtcaggagt catagatgca agcatcacga acagaataca agagatagag    180
ggaatctcag gtgcagaaga taccatgaa agcactgaca caacagtgaa agaagacaca     240
gaaaacaaaa aattcctaac ccaaaacatc caggaaatcc aggatacaat gagaaaacca    300
aacctaagga taacaggtat agaagagagc aaagattccc aacttaaagg gccagtaaat    360
atcttcaaca aaattataga gaaaacttc cctaacctaa agaaaaagat gcccatgaac      420
atacaagaag cctacagaac tccaaataga cgcaatcaga aagaaattc ctcctg          476

<210> SEQ ID NO 27
<211> LENGTH: 27
<212> TYPE: DNA
<213> ORGANISM: Artificial Sequence
<220> FEATURE:
<223> OTHER INFORMATION: synthetic

<400> SEQUENCE: 27
ctcttcacag caatgaaacc ctaagac                                                27

<210> SEQ ID NO 28
<211> LENGTH: 29
<212> TYPE: DNA
<213> ORGANISM: Artificial Sequence
<220> FEATURE:
<223> OTHER INFORMATION: synthetic

<400> SEQUENCE: 28
gctggtcatg ttttgactct attaattgg                                              29

<210> SEQ ID NO 29
<211> LENGTH: 776
<212> TYPE: DNA
<213> ORGANISM: Artificial Sequence
<220> FEATURE:
<223> OTHER INFORMATION: synthetic

<400> SEQUENCE: 29
ctcttcacag caatgaaacc ctaagacact gtttttggga tggccagtct gcactatctg     60
caattcttta cctagtctgt caatacaaag accgaaattt aagagacaca ttccatggcc    120
aagaatatct tcaatataaa gaatcagaa ttaaattatc aaggacttct acctctagcc      180
atgatggact cttatacatc actataactg tgcaagagat acagatcctg tcactgccgg    240
ccaccttaca gcaggtagag aaggaacggc atcatgatat gataagccta acagcatctt    300
agaatttctg gctgagaagc ggctctgaga agggaagtgc acaggaacag ggctcgagca    360
```

```
cttttcatag agtctccctg agtgtgtgct gattccccat tgtgaaaccg aggaaaagtg      420
cccatggaat ctagaaaaag gcaactgcta tcacagcact gaactggacg gtgtctctaa      480
aggctcacaa agggctggga gacggagagg cggcaagctt cctaactggc atccaaagcc      540
ttcggcagtc agctcagaag aatcatactg aagggctaag ttagactcaa aggaaagcta      600
ctatacccac ccaaataaac tttacaaatg agttgtaaaa tgatcatgta ctcagagtaa      660
ctgcttcctc atgtaagatg taacacttca aggaaaact caaaagccag gctttgtgct      720
cacactgaat tagaaacgtg ggcaaaccca attaatagag tcaaaacatg accagc         776
```

<210> SEQ ID NO 30
<211> LENGTH: 28
<212> TYPE: DNA
<213> ORGANISM: Artificial Sequence
<220> FEATURE:
<223> OTHER INFORMATION: synthetic

<400> SEQUENCE: 30

```
cacaaccatc tgtaatgaga tctgatgc                                          28
```

<210> SEQ ID NO 31
<211> LENGTH: 23
<212> TYPE: DNA
<213> ORGANISM: Artificial Sequence
<220> FEATURE:
<223> OTHER INFORMATION: synthetic

<400> SEQUENCE: 31

```
gatcagtgag tttgaggcca gcc                                               23
```

<210> SEQ ID NO 32
<211> LENGTH: 364
<212> TYPE: DNA
<213> ORGANISM: Artificial Sequence
<220> FEATURE:
<223> OTHER INFORMATION: synthetic

<400> SEQUENCE: 32

```
cacaaccatc tgtaatgaga tctgatgctt cttctggggt gtctgaagac agctccagtg      60
tacttacata tataataaat aaataaatct taaaaaaaaa taaataaatt tcagcatcct     120
aagagcactg ctacccttc ctgaggatct gggttcaagt cagctgtact gtgaatcctc      180
tggattctga gcactgcatg catgcgctgc acggacatta cagacataca ttcaggcaaa     240
tgctcataca cagaaaataa aagtagatga aatagttctt gatattttt tcttgagcct      300 ttttttttt tttttgaga gggtctcaac catatcagcc tggctggcct caaactcact      360
gatc                                                                   364
```

<210> SEQ ID NO 33
<211> LENGTH: 19
<212> TYPE: DNA
<213> ORGANISM: Artificial Sequence
<220> FEATURE:
<223> OTHER INFORMATION: synthetic

<400> SEQUENCE: 33

```
atcagccgat tctgggcaa                                                    19
```

<210> SEQ ID NO 34
<211> LENGTH: 16
<212> TYPE: DNA
<213> ORGANISM: Artificial Sequence

```
<220> FEATURE:
<223> OTHER INFORMATION: synthetic

<400> SEQUENCE: 34
gccgggaggt ctgcca                                                      16

<210> SEQ ID NO 35
<211> LENGTH: 1062
<212> TYPE: DNA
<213> ORGANISM: Artificial Sequence
<220> FEATURE:
<223> OTHER INFORMATION: synthetic

<400> SEQUENCE: 35
aggtgcagcg atcagccgat tctgggcaaa gccagcgcta acccgccaga gctccgagga      60
tcgatggtgc aacacacccc ttgttcccag agaccccgc cgagacttgc ataggacttt     120
ggcaaacttg ggaaagcaac ttttccccag gagtcaggtg cctggaagaa agggaacaga    180
actaagaaag ggggaaagcg aaagagcctg gggaaaggag aagtccgag cgggctggac     240 gccgctgcta ggccggcccg gcagcgcaac ccccccaggg gagaaaagga tgcacaaaag    300
cctggaggcg agtggtggga ggccaaatga gaagagatct ctgggtcctc caccttccac    360
ccaagatcac gatccccggg aagtcaccag cagggtcccc ggcctcccgc accagctgcc    420
ggcgtgcccg agtcaaacac gctgggagcg tggcggggag gaggcgagct ggttgcagcg    480
gtgcgctcct gtgcattccg gtggggtccg caggctggca ggatcgtgcg catttcgagc    540
gcgtgcggga gcgtgcgagg ggctgggcaa gcttgcagcg cgccagggtg ggaaagacat    600
cccgaatgca tcaggtgcag agccgggaac ccaccgtgcg cggccgggag cgcacagcga    660
gctcccgctc caccggccgt tcccaccgag agccgaggag gactcggagc gccagagtct    720
ctccgaagcg tccctctctc cttaaaagag ggcatcaagt ccaatcaaaa aagaagaaa     780 aaatcccac cacgtttttct ctaaagaaaa caaaacccga tcggatacca gtccctcc     840 acccgacccc caggttcact ccttgcttcc tccgggtcta gctccccagc tcgccagcga    900
ataaacacaa ataaataaga cacaatccta tctcacgcca agcgcaccgg tccgcataca    960
tatgagcacc cacaggctct ctgctcctcc gccagccctt gcctgtacaa agacacccag   1020
tccccgacta cacgcgcccg cagccctggc agacctcccg gc                      1062

<210> SEQ ID NO 36
<211> LENGTH: 14
<212> TYPE: DNA
<213> ORGANISM: Artificial Sequence
<220> FEATURE:
<223> OTHER INFORMATION: synthetic

<400> SEQUENCE: 36
gctgctgccc cggc                                                       14

<210> SEQ ID NO 37
<211> LENGTH: 26
<212> TYPE: DNA
<213> ORGANISM: Artificial Sequence
<220> FEATURE:
<223> OTHER INFORMATION: synthetic

<400> SEQUENCE: 37
acggattctc tttctctgat ttgagg                                          26

<210> SEQ ID NO 38
```

<211> LENGTH: 1667
<212> TYPE: DNA
<213> ORGANISM: Artificial Sequence
<220> FEATURE:
<223> OTHER INFORMATION: synthetic

<400> SEQUENCE: 38

```
gctgctgccc cggcggcagc ggctgctgct cgttggctag gtggagaggg caaaaggttg      60
caaaggaaga ggagccgcag aggacctggc agtccccaag gggtcagaag gatgagtggg     120
agaagcggtt cccactttag ccccaggttt tttcatttcc actgggcatg cggtgtatcc     180
cgcgccccta actccccaa ctccagtact caagagcgca gttttgtccc gttttttatt     240
atttgcacca gttcagtgtg tggcttctag cttttcactt tttctcagga ttcggatcgc     300
atcctccctt accctagctt taaatgggtc gtttcccaag tcccaaacca ggcctctgat     360
gcctgaccac aggagttcgc cggatttggc cagataaatc taaaggggcc agtagaaatc     420
tggtaggagg cagcacctcg attttgctat ctagattgtt gcacactgag atgcgaaggc     480
ctgagtagta atactttctc actcctaatc tcgggcatcc tccccgcccg cacgccccc     540
cccatcttcc ccggcccag gaacctggat ggaaagttct gaagattctg cgcctaactc     600
agctctgcct tcaggagcta ctggaagctt ggaagagcgc tgggccgctc cagagtactt     660
tcttccctca gcggctggac cattttaaag ggcgtacttg agatgacaaa ccgtagggta     720
gaaagaccaa aggaaaaaaa atattccttc tacccgcgga aagcaccgtc tcctcctttg     780
cacacgaagc taggcaggga attgaggttg gagggttctt ttctgagcac tggcctccgg     840
ccaaagcccc agcgcagtgt tattgggggt gtggtggaga gcgccaccca ggggtctcag     900
aaaagtcacc cacacagccc cacccctccag tcctaaggta ttagttccag gcttcagttt     960
aggggtgctg tgttcttggc ttaccgcgga tctcccacag gacccacaga atcgtatctt    1020
gattccccag gagctaaagg agaaggaaag tgggcggtga atggagacaa aaaaacccac    1080
gaagaccagg tggcagagct tacacaagat ctgcacgggg gtctgctaac gtggtggtca    1140
tttataataa caaggcatcc taacaattga cactcccagg tctcagatta gcagtgggag    1200
agagaagtcc gcagaaccga gcactgggaa gcaaaggaag aaaactacaa ttgagttacc    1260
ctctcatagg cagtgtcatg tgggtgagac aaggcgaaac ccccctaccc cagtcagttg    1320
gtatacaaca aaaacaccct tgtgtaaagg ctacctgatt cttttcaagtt aaggcgaacc    1380
ctctgtaaga agtaggggat ttgaggacgt taagaaggaa ctgccatcta taaagaaagc    1440
aagagtggat gagcagaagg gaacaggaaa aacacacacc cccctgccgt gaatgcctgg    1500
ccatgggaat ggagcattga gcttgttgag ttcctgtcta aagaaggctt gctatctagg    1560
gtccacatcc acctaccacc ctctctccag cagtcaccgg agaggcacac gattaacctc    1620
tgatcctatt ctaccattaa tcctcaaatc agagaaagag aatccgt                  1667
```

<210> SEQ ID NO 39
<211> LENGTH: 22
<212> TYPE: DNA
<213> ORGANISM: Artificial Sequence
<220> FEATURE:
<223> OTHER INFORMATION: synthetic

<400> SEQUENCE: 39

```
ctcaatctcg gcattgaata ga                                               22
```

<210> SEQ ID NO 40
<211> LENGTH: 26

```
<212> TYPE: DNA
<213> ORGANISM: Artificial Sequence
<220> FEATURE:
<223> OTHER INFORMATION: synthetic

<400> SEQUENCE: 40
catgataccg tgaagattta agtttg                                          26

<210> SEQ ID NO 41
<211> LENGTH: 535
<212> TYPE: DNA
<213> ORGANISM: Artificial Sequence
<220> FEATURE:
<223> OTHER INFORMATION: synthetic

<400> SEQUENCE: 41
ctcaatctcg gcattgaata gaaattatcc caaacagttc ttattaaata tccaggttat      60
tctgggcctt cgtgagcatg gcaatttcct caaagcagga tttagaaaat ctgagtcata     120
agacccattt ttgtgcaaat ttctccaaca agaaaaatg catttataaa caccccattg      180
aagctgcagg aagagtaagc aaaagggttg ttagtgaatg agcgatagta catgcatatc     240
ggcaacaaag agcccggtta ttaaccaagg tgtgtgaaat gccattaaca tgttttgatt     300
tgatggatct ttaatattat attttatgaa tagaaaaact actcagaaaa attccattag     360
gccacttcca ttttaattat tttagcttct cagatgtgaa tttctttgtt gttggatgtc     420
tgagggattt aacctccctg atggacagag aatgctgtag tgacacagtg accaatgcca     480
gctgttctga ggccacatcc tacatctgac aaacttaaat cttcacggta tcatg          535

<210> SEQ ID NO 42
<211> LENGTH: 21
<212> TYPE: DNA
<213> ORGANISM: Artificial Sequence
<220> FEATURE:
<223> OTHER INFORMATION: synthetic

<400> SEQUENCE: 42
ttgagttcct gtcctggctt t                                               21

<210> SEQ ID NO 43
<211> LENGTH: 26
<212> TYPE: DNA
<213> ORGANISM: Artificial Sequence
<220> FEATURE:
<223> OTHER INFORMATION: synthetic

<400> SEQUENCE: 43
aaaagtcatg tcttcaaaaa caaaca                                          26

<210> SEQ ID NO 44
<211> LENGTH: 360
<212> TYPE: DNA
<213> ORGANISM: Artificial Sequence
<220> FEATURE:
<223> OTHER INFORMATION: synthetic

<400> SEQUENCE: 44
ttgagttcct gtcctggctt tctttagtga taaacagcta tgtggaagtg taagctgaac      60 aaacccttt ctccccaatc tgcttttggg taatggtgtt tcaccacaga aaccccaagg     120
aagacatgca ataccctgat aatttattca aatacatctc ctagcctcta actttccctt     180
aaatttttcc ttgagtctct gtaacctcac tgtgtggcat cttctttcac attgtgtgtg     240
```

```
tgtgtgtgtg tgaattctac ataactttat taaagaattt atacttatac ttgttaagta      300
tatcaaagga atttccaacc agtagtatct aatttgtttg tttttgaaga catgacttttt     360

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
gagctcccag ggactaaacc                                                   20

<210> SEQ ID NO 46
<211> LENGTH: 24
<212> TYPE: DNA
<213> ORGANISM: Artificial Sequence
<220> FEATURE:
<223> OTHER INFORMATION: synthetic

<400> SEQUENCE: 46
cagtgttctc tggaattttc attg                                              24

<210> SEQ ID NO 47
<211> LENGTH: 548
<212> TYPE: DNA
<213> ORGANISM: Artificial Sequence
<220> FEATURE:
<223> OTHER INFORMATION: synthetic

<400> SEQUENCE: 47
gagctcccag ggactaaacc accaatcaaa tggagagacc catggctcca gctacatatg       60
tagaagagga tggccttgtc agacatcaat gggaggagag gtccttggtt ctgtgaaggc      120
tgtatgcccc cagtgtacag gaatgccagg gccgagaagt gggagtggtt gggttggtga     180
gcaaggggga gggggggtaa ggaatagggg gttttcagag ggaaaaccag gaaaggggat      240
aacatttgaa atgtaaataa agaaaatatc taattaaaaa cttgtttttt tttttttta      300 aaaaagagtc agcgtaaatg gcctcttctc ccatacatct acaaacaaaa tcactactag      360
gaacaattac acaggacatt tataatcaat ctctctagct tatattctca aggcagcctg     420
tgaggctact gaatcaataa ggttttttttt taatatttta tcaggcaata tataagtgag     480
atattataga tactttatct attaggtaga taatatttct tgatcaatga aaattccaga    540
gaacactg                                                               548

<210> SEQ ID NO 48
<211> LENGTH: 55
<212> TYPE: DNA
<213> ORGANISM: Artificial Sequence
<220> FEATURE:
<223> OTHER INFORMATION: synthetic

<400> SEQUENCE: 48
tcgtcggcag cgtcagatgt gtataagaga cagatgccaa accactgtga gtgta            55

<210> SEQ ID NO 49
<211> LENGTH: 54
<212> TYPE: DNA
<213> ORGANISM: Artificial Sequence
<220> FEATURE:
<223> OTHER INFORMATION: synthetic

<400> SEQUENCE: 49
```

```
gtctcgtggg ctcggagatg tgtataagag acaggtcccc aatgtctgct tcaa        54
```

<210> SEQ ID NO 50
<211> LENGTH: 624
<212> TYPE: DNA
<213> ORGANISM: Mus musculus

<400> SEQUENCE: 50

```
tcttaagtct gaggctcaca gacccttatt tcacaggtca aaggtcaaag gtcaaccagt    60
caacggtatt ctgaggaagt gctggcacaa agatgagccc actggagagt tcctctacaa   120
agccaacttc cggggaaatg gaggctatgt atactaccca gcccagcctc ctacattttc   180
tgcaggtttg gtgtctgtcc acttccttgg tttgttttgt tttgtttttt tgttttgac    240
acaagattta caaccctgac tcaccttgaa ctcactctgt agcccaggct ggctccaggc   300
tcatgatccc cctgcctcgg cctctcgaat gccaggatca caacatgtac taacatgctc   360
agcccctgc atggagcttc atgggaaaga aaacctttga acgatgagtg ctaccgcaga   420
cctccaccct aaaccaaagc aagttcttca gatgcccga ggacacttga tgaatgttcc   480
ctaccttcta aaggtgacat tagatcttcc cagagaatgt ttcttaatgt cagcagccgt   540
gtcatattcc aagagggtc attagtcact ccttgtgtca ttgtgctata catcactcaa   600
gactaagctg tttccatgtt cctc                                          624
```

<210> SEQ ID NO 51
<211> LENGTH: 1071
<212> TYPE: DNA
<213> ORGANISM: Mus musculus

<400> SEQUENCE: 51

```
gtgaaagaaa cccgggagaa ggctttctcc agccccaaa gttttgatga tgaccatgac    60
tacgatggct gacggcttgg aaggccagga ctcgtccaaa tccgccttca tggagttcgg   120
gcagcagcaa cagcagcagc agcaacaaca gcagcagcaa cagcagcagc agcagcagca   180
acagcagccg ccgccgccgc caccgccgcc gccgccgcag ccgcactcgc agcagacctc   240
cccggccatg gcaggcgcac attaccctct gcactgcttg cactcggccg cggcggcggc   300
ggcggcggcc ggctcccacc atcaccacca ccagcaccac caccacggct cgccctacgc   360
gtcgagcgga ggcaactcct acaaccaccg atcgctcgcc gcctaccct acatgagcca   420
ctcgcagcac agcccttacc tccagtccta ccacaacagc agcgcggccg cccagacgcg   480
cggggacgac acagatcaac aaaaaacgac agtgatcgaa acggggaaa tcaggttcaa   540
cggaaagggg aaaagattc ggaagcctcg gaccatttat tccagcctgc agctccaggc   600
tttaaaccat cgctttcagc agactcaata cctggcccct cccagagag ccgaactggc   660
tgcttcctta ggactgacac aaacacaggt gaagatatgg tttcagaata gcgctctaa   720
gtttaagaaa ttgctgaagc agggtagtaa cccacgagag agtgaccccc tccgggttc   780
agcagccctg tcaccacgat caccagccct gcctccagtg tgggacgttt ctgcctctgc   840
caagggcgtc agtatgcctc ccaacagcta catgccgggg tattcacact ggtattcctc   900
accacaccag gacaccatgc agagaccaca gatgatgtga cttctctgag tgaacgccta   960
cggagcttct gaaggagca ttctccaccg gcagaagaat ctgcacaaac atggcagcat  1020
ttttacttgt ttaatgagtt taagacatta catgataaaa aacaaagatt t           1071
```

<210> SEQ ID NO 52

<211> LENGTH: 1892
<212> TYPE: DNA
<213> ORGANISM: Homo sapiens

<400> SEQUENCE: 52

```
atgatgacca tgactacgat ggctgacggc ttggaaggcc aggactcgtc caaatccgcc      60
ttcatggagt tcgggcagca gcagcagcag cagcagcaac agcagcagca gcagcagcag     120
caacagcaac agccgccgcc gccgccgccg ccgccgccgc agccgcactc gcagcagagc     180
tccccggcca tggcaggcgc gcactaccct ctgcactgcc tgcactcggc ggcggcggcg     240
gcagcggccg gctcgcacca ccaccaccac caccagcacc accaccacgg ctcgccctac     300
gcgtcgggcg agggaactc ctacaaccac cgctcgctcg ccgcctaccc ctacatgagc     360
cactcgcagc acagccctta cctccagtcc taccacaaca gcagcgcagc cgcccagacg     420
cgaggggacg acacagatca acaaaaaact acagtgattg aaaacgggga aatcaggttc     480
aatggaaaag ggaaaaagat tcggaagcct cggaccattt attccagcct gcagctccag     540
gctttaaacc atcgctttca gcagacacag tatctggccc ttccagagag agccgaactg     600
gcagcttcct taggactgac acaaacacag gtgaagatat ggtttcagaa caaacgctct     660
aagtttaaga aactgctgaa gcagggcagt aatcctcatg agcgacccc cctccagggc     720
tcggcggccc tgtcgccacg ctcgccagcg ctgcctccag tctgggacgt ttctgcctcg     780
gccaagggtg tcagtatgcc ccccaacagc tacatgcctg ctattctca ctggtactcc     840
tctccacacc aggacacgat gcagagacca cagatgatgt gagttgccca agggaacacc     900
ctagggaaac gtctgaacaa ggaaaagagg atccgggacc tgcttgtatc tgcgaaaagg     960
agccaaagga gcaggcttag gagagctcat aagtgtggca agaagccgac taggctcatt    1020
ctctctccct ctctctctct ctccctctcc tttcttttta cttcttcctt tcctccattc    1080
cttctttctt tccttttcct ttctaccttt cttttctttt tgcctttcac ctttttctc    1140
atttaccttc tctcttgagc aacgtcagta attgatcttg catctcagag agagagaaag    1200
agcatgtgtg agagagaaac tggtttctat gccagcactc ctgaaacccc ttactgtaag    1260
gatatttct cttaccccctt gggatccagg ctctgagtct cttctctttg ggagtatcca    1320
tcaaaatgac ttttttttaaa aacagatttt ccccaacca gaagaatctg cacaaacttg    1380
gcagcgtttt tacttgtta atgagtttaa gacattacat ggtgaaagag aagcattttg    1440
gactcctgca tttttattta ccattcccag actgacgaga aaagaaaat tcctcacata    1500
acagcccttc tctaaagaaa aggaaaaag tggctgtaag attagaacat tgctacaaag    1560
ggaatgctgc atgttttatc aaaatgcaat gaccaggaat gatggttgat taaaaaaaaa    1620
caaaacaaaa accactcttt ccccaccccca ccccccaaa ccctgaactg gaatcaggaa    1680
agacggagga aacaatcaaa atcaccattc tattgctttg acacctttac taggtgaatt    1740
ggtggcattc acaaagctaa tagggacgtt tatatcaaga acatttctg tatatattgt    1800
tgaattttag ttgtacatat actttgtatg tttttgtctt ctttcatata tggagtaaaa    1860
gccacaaaac gctgaaaaaa aaaaaaaaaa aa                                  1892
```

<210> SEQ ID NO 53
<211> LENGTH: 4247
<212> TYPE: DNA
<213> ORGANISM: Mus musculus

<400> SEQUENCE: 53

```
gcttcaaatt ggatggcact gcagctggag gctttgttca gaattgatcc tggggagcta      60
```

```
cgaacccaaa gtttcacagt aggaaggggg aaaaaagaaa agaaaacatt tttcctaatg      120
taacaatgcg aatgctagaa aatgacaaga ctgatcggtt ttaaaccatt ctgaagactg      180
actgagcgtg gaagttgctc aacaaaaaag ggaacgggga tattgaacca gagagaaacc      240
tacgcccaga agaacatgtc cctggattgc tttcccactg ctgtggagtg tcttgaacac      300
tggtccctgg acaccaactt caagaagact tcatggatgg ctgtccagtc ttatgagcca      360
cagtttcccc tctacatttt cttcactcca gcgaggctct tatcagggtc agatcagaga      420
tgaaccagct ggacgacaga ttggagcgct gacctcttag agtgctaaca gtgaacagtg      480
tggggtcaga tctatagaaa gataataata agaaaacacc ctatatgcaa gggagagggA      540
tggttcataa tttcttaaag attgaaatca aggaacaatc aaaatataga agaatgtgga      600
cgtgttttgc tgcaggactt ctgttttgtc cccattggaa tatgtattat ggtattcctg      660
ttggatcagg actcagggGC aaggctaagc attccagtgg tcctcctact tagctcttgt      720
cctttcgtaa gaaacaccaa ctcattagtc tctatattac ttctctgtac tgtagatctg      780
cattcttgat ctgagagata ttggcaatga cactcttgta tgataaagct caatgataag      840
agtacttcaa acccccttga actttttgtt tatacatcaa gtggtgacat tgtgtattga      900
gctaattaga tcaatggagt cacagggtga tactgaactc ttttaaaata tttggctgaa      960
acatgacatt gtagttattt gtagaagaga acattatgga atatgaaaaa catcacagaa      1020
cacagaacta gcagcagaaa ctagcagcag gtagacattt ttccttttcc atagagcttt      1080
caaccaaatg tctctgtaga aaatagtggc tatcgtgtat atatatagcc acatagatgt      1140
ccttgagtgt accctgtagt cagtgggaga gttcctactg ccacagtcat ggccatggct      1200
atgttctcta agcctacatt ttataaacac tctgtgaatc ttgactactt ttctttagca      1260
agcattgcaa agtcctggga tgtcagagaa gtgcctgggg ttggcagggt ttctagagag      1320
gaaattgtta aatgatttga accagaaaac aaacagggga tggggttcag aaccaacaat      1380
tacctctatt ctatgtagga aaccacaaca tgaaatatgc tgggcatgga aactttgata      1440
ccttggtttt tcattctttt taaaaattaa tactaaagag ctatgcgact gtaggcaagc      1500
catttcccat cccctgtgaa tatctcccag atgactttaa atcccttcta gttctgaaag      1560
gcttttaaca tcagggccca ggctccagtg gccagtttca aaataccctc ccttttgatg      1620
ttaggttaca taaacattgt tcttttttag ggagggtctc ttttatcaac ttttaaaaac      1680
acacatcagg ttctctggta ttaaaaagat gccatctctg agtcccctac tatctgtgct      1740
gcctgccttt cctcctgttc tttccttatt cccatcccta ttgaacttgt gctatgcagt      1800
atgcatcagg tatgtgttag ctttggggat acatgataga taaactggac acacagggtc      1860
ttcccattct cttctggaat tttctttgga gggagcctct tgtatctaga cagaccgtgc      1920
tgtggtaccc cagaggtaac cacctacagg cttcactctg cctaagcaat tttgctgtgc      1980
actaagatac acattcaagt aactttagat taccacaata actttctcca ggtatgagga      2040
aaagagataa tttacttctg agatgtgtat aggatagccc tccatcctgg gaagaacagt      2100
gactactccc tgcatcccga ccttgcccag ggaaagctaa tgtttctctg tgttatccct      2160
gtgacttgcc acttctttaa aaaggaatgg gcaaacaata aacagacaaa aatgttgtct      2220
gacctcattg gaaatccttt taagaattaa tccttctat ctccttcatt atcaacaaat       2280
ctattgaata cttatctctg agtccagggc atatttttata atacataaaa caatggaatt    2340
tcaaaattgg agcactgaca tacaatattg gttttgagta ttttttattat agggaatgac    2400
```

| | |
|---|---|
| tttagacatt gcaatttatg acttaactga taaaatggat gactcttgac tttcaatttt | 2460 |
| cattttcagt tcagtcgagg aatagcttcc tccaggtaat gtctatactt tcctatgact | 2520 |
| aagggctcta actatctctg ttgcttttct ttatgtaggc atatgttagt atttatttc | 2580 |
| tatatgacaa atgtattaaa gaaagcatga aattaatgag ataaactttt cagataggag | 2640 |
| tttagaaaat caaggggcca agataaataa atgaaaaatc aacttaaata attaacatat | 2700 |
| tccagatata ttggaataaa tgtttattgt acccttttgg ttttgtcttg ggttatttt | 2760 |
| ttcttatctc actgattttt ttttcttttcc tttttagctt ttttgtcttt tttgattttt | 2820 |
| gttgttgcgt ttctccttt tttttttctt gttgatgttg tttgtttgtt tgtttgtttg | 2880 |
| tttttgaga aagaacagaa ggttggttgg atagggaggt ggggaagatc tatctggatg | 2940 |
| gagttgggag gagggaaat acacgatcaa aatatatttt gtgatgggca gggcatagtg | 3000 |
| gtacatgtct ttaatctcag cactctggag gcagaggcag gtggatctct atgagatgga | 3060 |
| ggctagcctg atatacaaag tgagaccaga acatagggct gcctcaaaaa ctttatatat | 3120 |
| atattaaaaa tgtttgctttt ttgagacagt cacagataac caaaactgat cttgtaatga | 3180 |
| tgtaaacatg tccagctaat tttcaaatat tgtagggcag catttctccc tttgtgcaca | 3240 |
| cgtggagtca gcaaatccat ataattctaa ccattctggt gaaaaggaga acactcggcc | 3300 |
| aagcatctca cacttccaag tgtgaagcct tgtttgaaag ctccgagtat ctaaatagta | 3360 |
| gccctgtgaa aggtaaattt atgaatggtc tggtgtgttc ttattccagc cattgacctt | 3420 |
| aaagcaactt atatatgttt tctttatcct tcaagagaaa agaaaaatca tattttttcca | 3480 |
| agcaattaaa attcttctgc ttcaggtagg aagaaggaat taggagttat gtctccttgt | 3540 |
| atataattgc aagtttcatt tttcttgttt taatgattga cagaaaactg ataaactgag | 3600 |
| acatctcctt attaggggttg aatgtactct cttggtggcc ccattgctaa tttgtttgac | 3660 |
| tattttccat gatttcttac tctgtaatgg aaaggtttat taaatatgag ggttgcaaag | 3720 |
| ctttctgaat actaatgaac ttatttgcca aaatttaaat gttcttcttg tcagtgaatg | 3780 |
| cctgtctcac ttaacaggca ccaaattgaa taatgaagaa aattagactc tatcgtaccc | 3840 |
| tcaagagaaa tcgcgtgtga attgtaatag aaaattgagg gagaaaaggg tcatattgta | 3900 |
| gcaataacac tagataattt ggattatttt aaaaaaggat gaacttaggg aagctcaggt | 3960 |
| cttttcaaag aaacacacat ttggttaatt catgcaaaac gctggtttcc cctcaaccca | 4020 |
| ggtggtctat acctatcgcc agtttacaga aaaaggaagc caggtggatg gaaaacgtgt | 4080 |
| gccaagtttc tgtgcttaca atccactaaa ctcattctca tatgaggact ttatatacct | 4140 |
| gtgatggagt gggaaaatca ataacctgga aaaatgagt accattttcc aaagaagttc | 4200 |
| aataaagaga tggaatttgg gaaactgctg cagttcttcc tataagc | 4247 |

<210> SEQ ID NO 54
<211> LENGTH: 1990
<212> TYPE: DNA
<213> ORGANISM: Homo sapiens

<400> SEQUENCE: 54

| | |
|---|---|
| atttcacacc tggatgtgct cactcaacca agaatataga gaaagagctt ctgccctgag | 60 |
| actcagaaaa atattctcct gtgctttggt tcagtataga tttctaaacc ctgatcattg | 120 |
| cttaagagat attcactgag gacagagtct tgctctattg cccaggctgc aactggtgtg | 180 |
| atctcggctc actacaacct ctgcctcctg ggttcaagcg attctcctgc ctcaagctcc | 240 |
| caagtagctg ggattacaag catgcaccac catgcctggc taatttttgt attttagtg | 300 |

```
gagacggggt tcgccacat tggccagggt ggtcttgaac tcctgacctc aagtgatcca      360
cctgccttgg cctcccaaag tgctgggatt ataagcatga ccactgcac ccagccttat      420 actgaacttt caatgggttc aattccacta ggagcataaa ggccactgca tatgagttgt      480
ggaaagaaga gattagaaga aggaagaact tgagatgagt tcctcccttc aacattctgt      540
ctcctcctac ctagcatctt ctttctttta gtctttctag aatgtccatc tgttttggc       600 cattgcggag agagaagctg agcttttaaag gagtaggagc ttcaaaggcg taggagcttc      660
aaaattcttg tttcttcatg tttgatcacc cttctaaacc tgtcttctgt tccttctgct      720
attctttttt cttagagcat aggaaagggg agcttttaaa ttaatactta aagcatggaa      780
aaaaagaact tgagaagaaa gtaaaacaag ggagatgagg ctagtaaagt aaggaaaatg      840
aagaggaaga ggaggaaggg ttagcttcta aattccaagt caaattgata tggaacaggc      900
aagccgcttg tcttacttaa acttcagaaa aggatctgct gaaacttgat agaaatggaa      960
agggaaatcc ttggggtggg gaacctccaa acattagtaa tgatattgaa caactcaaag     1020
tattgaggaa atctgcaggc tacatgcctg aagattaccc atgcagatag accaaaagga     1080
ttagaattat ctgttgatat tagtaatatt tattgacatc tagctagtat tggtaatttt     1140 aagtttaga ttaatttctt tggtaatagc tatgatatat tttatagaca agaattatat     1200
ctataggctt gctatcatag gctcttttaa tcagcattaa tttagtctac tgattttag     1260 cacatttgaa tcattcactt atgctaggta actcattgca aaataaaaag atgattcctg     1320
tatgtatggc agctatacat taaggaggag tctaccagaa tatgaaaaag tcagctgacc     1380
taaatattgc tgagacaaag gaaaacccac tcccttggag gagcatgacc ttttcctgta     1440
attcttccca ctgctgttgt tgagctcctt ggatcctggc tcctggacac catcatcaag     1500
aagactttat ggatgggctg tccacccact gagagaagag gagcatcagc tacagtttct     1560
ctctagattg ccttcttcat tttgagtaat gactgtcagc agggtcagat taaacacaaa     1620
acaactggac aattgcttgg aggactaaac tataagggca ctaacatgtc aatagtaggc     1680
taacacatcc atggaaaata tatttaccag ctcttctctc agggaggatt ctgtgtgggg     1740
ttggaagtaa tgatttgtta aattccttag gggtagaaag tagggcataa tcagaatata     1800
gaggaatatg ctgtttgact tcagggtttc tgttttttctt actaggatat ataaaacagg     1860
gactctagct agattgttta tgaccacaga gggtaggctg agtgctccca tgatcttcct     1920
gcttggttct tgcccataca gaggtcagcc tttcctctaa taaagattga acaagtagtg     1980
gtctgaggga                                                            1990
```

<210> SEQ ID NO 55
<211> LENGTH: 993
<212> TYPE: DNA
<213> ORGANISM: Homo sapiens

<400> SEQUENCE: 55

```
aggctttgta ccgccagggg ctggcggagc aacagagccc gtgggtgctc ttatgtatgc       60
ggaccggtgc gcgggcgcaa gataaggttg tggtttattt atttgtgtgt ttattcgccg      120
gccggctggg aagctagaat cggaggagct gacgagtaga tctgggggcg gaggggagca      180
ggactgggac tgcttacgtt ttgtttctct ttgagaaaac gtggtgggct ttttcttgat      240
tggacttgat ccccacccc cttttgcagg ggagggaggg aagctccaga gggtctgcag      300
cgctgcgggc cctcctcggc tctcggcggg accggcggtg acaccggagc tcgccgtgcg      360
```

| | |
|---|---|
| ctcccggccg ctctcggtgg gtgccggtct ctgcacctga tgcgttcggg atgcctttcc | 420 |
| caccctggcg cgcccgccgc tagctcgcac agcgcctcgc acactcccgc acgcgcttga | 480 |
| aatgcgcacg gtcccgccgg cccgcggaac cacccggacg cacggagcgc tccgcaccga | 540 |
| ctcgctcgcc gcctccccga gacgctcgca ccgtgcttgg gccgggcgcg ctggccgctg | 600 |
| gcgccgctgg ccagaggcct gggacccagc cggtcgctcc caggggtca cggccctggg | 660 |
| tcggagaggg agggcgggca gacccccttct cgcctttcct cccacaactc gctgcggggc | 720 |
| ttttgtgctt ccccttcgcc gcggggcggg tccgcctccc ctgccgctct cgccgcggag | 780 |
| tccagcccgc ccggactgtc gccgttcctc ccgtctctt tcgctttccc tcgtccctag | 840 |
| ctcagctctc cttctttcag gagtctagct cctcgggaaa agttgcttcc ccaagtttgc | 900 |
| tgaagtcgtc tccaagtctc ggtggggtc gctgggaact gggggggtgt gagagcgcgg | 960 |
| tcgatccccg gagctcgggc gggttatcgc cgg | 993 |

<210> SEQ ID NO 56
<211> LENGTH: 1712
<212> TYPE: DNA
<213> ORGANISM: Homo sapiens

<400> SEQUENCE: 56

| | |
|---|---|
| ggggttaatt gtgtgcttct cctgctactg cactgaggag aggctggtag gtggatgtgg | 60 |
| acagcaaagc ggaaacctcc agcaggcact atctaggcag aagctcaaca agtgtagtga | 120 |
| ttctttcttc tgtttccctg gtgaggcacc aggagggtct tttctcctct ccttacatcc | 180 |
| ctccactctt gctctccttg cagcccagtt cttttcctaac tttctttaaa tcccttccct | 240 |
| ctaacagggt gtatagacct tagttagaaa acaggtagt ctctaaatgg gattgctctt | 300 |
| tattgttaat gaaatgaata cccagggact gggcttcccc tccgcttgcc ctgggtttga | 360 |
| tgtggttgta tcccgtgcta tcagaggagc ccttccttca ctcaagtgtg ttcccctgcc | 420 |
| cagctctctc cgcagactcc tgctgggctg agctttccct gctcttaaga gtcaggagtg | 480 |
| gctcttgctg ggatggaatg acccgtcttt ggggctgcct catgagcggc tcttgtgaac | 540 |
| ccggatcagt tccgatgtgt aaactctacc gcctggcctt cagcgaacag atacagattt | 600 |
| ctgccaccttt ccatgaccct acagttcatg ggactgggtc tggggcagtg ccagaggcac | 660 |
| gcatggaggt gtgattctag gtgagtcctg cggaaaacct ctggcccacc cgtgagtcac | 720 |
| ggacagaaca tgcagactca ggccttggtg acataagctc cgcattgcta aaaccgcgtg | 780 |
| acctcgaggg ctgactggcc tgagaaccct ggatggcgct ctcggccacc cccacctccc | 840 |
| acccccaacct cctgggcttc ggtcagaatc cacagcccgt gcccgaagag cgcttcccgc | 900 |
| ctctggcacc ctaccttcgc tcagctccag ggaaaagggg agagggcagc tttctgcagt | 960 |
| cagaggaaga gtacattttc tttggctgct ctaccctctg aagtagggcg ccagctgaa | 1020 |
| ggaggacaca cttttgaggg gcccagaggt tgtccaagct tccccctgcc ccctgaagac | 1080 |
| tgtgcactga gctgggcgca gttctcggga actgtttcca cccagattgc tgggggggcgg | 1140 |
| gggggtagga tgagggcaga gccgagaggc tgtccaaggt ttgggagaga gaaaagtttc | 1200 |
| tcccaggact cgaccttggc ctccagcaat cgcgacagct aaaaacgggt gtctcgcttc | 1260 |
| gacaatagat ccccgcggac cttctggcac ctggttcact agcgcccgcg aactctgcct | 1320 |
| cgggagactt attgaaatcc ggatgctcaa gccggggagc gcgcagtaac caggaggatg | 1380 |
| agagggccgg gtttgggcta ggaaagcggc cttttaaaac agatgtcagg gggactgcag | 1440 |
| ccccgagcca tgagaaaaaa gttaaaggcg agatgacacg cactgaattg gggcaaacat | 1500 |

| | |
|---|---|
| tggaagagga gacaaaactg cgtgcttgag caccggggtg cggggagggg gggacaaaac | 1560 |
| ccgtatccag tgcaaattaa aatcttggga gtaggtgggg gctgctgcgc gcccttcacc | 1620 |
| ctcagttccc ctattaagga ttctgagtcc ccatgcactc ctgtcctctg gctccttcct | 1680 |
| tcctctccgc tcggccggtg agaggcggcc gc | 1712 |

<210> SEQ ID NO 57
<211> LENGTH: 808
<212> TYPE: DNA
<213> ORGANISM: Homo sapiens

<400> SEQUENCE: 57

| | |
|---|---|
| aagacagaga taaagacata gttcttgccc ccacagagtg tatagtctta aggaacttat | 60 |
| aaatggctta gtcttgaatc ttgaacttaa tattcctaca aaatacataa ggagaatgac | 120 |
| actgggtgtg actaatggcc tacttagcct ggaatgtggt acttttggtg gcatgaagag | 180 |
| acattccttg gaagacatg atgtcaccct tagaaggaag ggaacattcc ccagagtatc | 240 |
| cctgatgccc tatgaataac atggtctggc ttagggtaga ggccgctagt agaacaggct | 300 |
| ctgtttagag tattccttt acacaaaaag acacatagaa agtacaggag agctagtctg | 360 |
| ggcgtggtgg ctcatgcctg taatttcagc actttgggag gccaagatgg gaggatcact | 420 |
| tgagcctagg ggttcaagac cagcccgac aacatagcaa gacctcgtct ctattaaaaa | 480 |
| caattattta aaaagaaag tacaggagaa tggactgaat atggaaacac tctgcagtct | 540 |
| ccctggaagt tgctttgggg aggaaatact gatagcctca taactttgca ttcatccctt | 600 |
| cctcttaaaa ttagagcaca gaatgccgtt gactatttca cctttccttt gtcatttgaa | 660 |
| ttaaaggtaa atggacgttg aaagtgtgtt tttgacttaa aggtctaagg aggaagagtg | 720 |
| agcccattgc taaagtacat aagctttccc tttactcaat tctgtgtcta cttggaaagg | 780 |
| tgaatgaggc tagggcaagg ttctctta | 808 |

<210> SEQ ID NO 58
<211> LENGTH: 250
<212> TYPE: DNA
<213> ORGANISM: Homo sapiens

<400> SEQUENCE: 58

| | |
|---|---|
| gcaatttccc agaggcagga tttaggaact ctgagtcata aggcccatta ttgtgcaaat | 60 |
| ttctacaaca aagcaaaatg aatttataaa catcctattg aagctctagg aaaagtaagc | 120 |
| aagaaagttt ttagcaagtg aggaatagta catggaaatt agtaatgcag actcactgtt | 180 |
| attaattgaa ggtatgtcaa atgtcattta tttcttttt ttttttttt accttatgt | 240 |
| ctcaagtggg | 250 |

<210> SEQ ID NO 59
<211> LENGTH: 219
<212> TYPE: DNA
<213> ORGANISM: Homo sapiens

<400> SEQUENCE: 59

| | |
|---|---|
| gcatgctgaa taatttattc aaatctttct tctagtttct gaatttctct tcagtgggtc | 60 |
| cttgagccct tactacctca gtgtagtaag tgtacccatc tatcttttgt gttctgcttc | 120 |
| cctgtggaaa ctccatataa cttggattgt gggaatgatc cttcagagca gctttgtatt | 180 |
| tatatttgcc aagtatgcca ggggaatcac caaccatct | 219 |

```
<210> SEQ ID NO 60
<211> LENGTH: 174
<212> TYPE: DNA
<213> ORGANISM: Homo sapiens

<400> SEQUENCE: 60
aaatgtctct ttctcctatg gacaaagtta ctgtaagaaa caataaaaca agaaaaaaac      60
cttacaaact ctccagttta tattcttcac aagctatgtg aagctattgc acatgtttgt     120
gtgtgtgtgt gtgtgtgtgt gtgtatcatt acatcaggca atgtggaaaa aaaa          174
```